(12) United States Patent
Halcomb et al.

(10) Patent No.: US 9,161,934 B2
(45) Date of Patent: Oct. 20, 2015

(54) DERIVATIVES OF PURINE OR DEAZAPURINE USEFUL FOR THE TREATMENT OF (INTER ALIA) VIRAL INFECTIONS

(71) Applicant: Gilead Sciences, Inc., Foster City, CA (US)

(72) Inventors: Randall L. Halcomb, Foster City, CA (US); Paul A. Roethle, San Francisco, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/595,072

(22) Filed: Jan. 12, 2015

(65) Prior Publication Data

US 2015/0126509 A1    May 7, 2015

Related U.S. Application Data

(63) Continuation of application No. 14/006,649, filed as application No. PCT/US2010/052802 on Oct. 15, 2010, now Pat. No. 8,962,652.

(60) Provisional application No. 61/366,790, filed on Jul. 22, 2010, provisional application No. 61/254,103, filed on Oct. 22, 2009.

(51) Int. Cl.
| | |
|---|---|
| *A61K 31/522* | (2006.01) |
| *A61K 31/437* | (2006.01) |
| *C07D 473/16* | (2006.01) |
| *C07D 473/18* | (2006.01) |
| *C07D 473/24* | (2006.01) |
| *C07D 473/34* | (2006.01) |
| *A61K 31/5377* | (2006.01) |
| *C07D 471/04* | (2006.01) |

(52) U.S. Cl.
CPC ............. *A61K 31/437* (2013.01); *A61K 31/522* (2013.01); *A61K 31/5377* (2013.01); *C07D 471/04* (2013.01); *C07D 473/16* (2013.01); *C07D 473/18* (2013.01); *C07D 473/24* (2013.01); *C07D 473/34* (2013.01)

(58) Field of Classification Search
CPC .................................................. A61K 31/522
See application file for complete search history.

(56) References Cited

U.S. PATENT DOCUMENTS

| | | | |
|---|---|---|---|
| 6,028,076 A | 2/2000 | Hirota et al. |
| 6,329,381 B1 | 12/2001 | Kurimoto et al. |
| 6,376,501 B1 | 4/2002 | Isobe et al. |
| 6,552,192 B1 | 4/2003 | Hanuset et al. |
| 7,157,465 B2 | 1/2007 | Isobe et al. |
| 7,521,454 B2 | 4/2009 | Isobe et al. |
| 7,592,326 B2 | 9/2009 | Karaolis |
| 7,642,350 B2 | 1/2010 | Pryde |
| 8,067,411 B2 | 11/2011 | Bonnert et al. |
| 8,067,426 B2 | 11/2011 | Biggadike et al. |
| 8,138,172 B2 | 3/2012 | Cook et al. |
| 8,507,507 B2 | 8/2013 | Halcomb et al. |
| 2004/0116362 A1 | 6/2004 | Sartorelli et al. |
| 2004/0132748 A1 | 7/2004 | Isobe et al. |
| 2005/0043239 A1 | 2/2005 | Douangpanya et al. |
| 2006/0052403 A1 | 3/2006 | Isobe et al. |
| 2006/0269936 A1 | 11/2006 | Vlach et al. |
| 2007/0190071 A1 | 8/2007 | Kurimoto et al. |
| 2007/0197478 A1 | 8/2007 | Jones et al. |
| 2008/0008682 A1 | 1/2008 | Chong et al. |
| 2008/0269240 A1 | 10/2008 | Hashimoto et al. |
| 2008/0300244 A1 | 12/2008 | Bonnert et al. |
| 2009/0047249 A1 | 2/2009 | Graupe et al. |
| 2009/0082332 A1 | 3/2009 | Abbot et al. |
| 2009/0099216 A1 | 4/2009 | Millichip et al. |
| 2009/0105212 A1 | 4/2009 | Isobe et al. |
| 2009/0118263 A1 | 5/2009 | Hashimoto et al. |
| 2009/0131458 A1 | 5/2009 | Lazarides et al. |
| 2009/0143400 A1 | 6/2009 | McInally et al. |
| 2009/0182005 A1 | 7/2009 | Maus et al. |
| 2009/0192153 A1 | 7/2009 | Hashimoto et al. |
| 2009/0202484 A1 | 8/2009 | Chong et al. |
| 2009/0209524 A1 | 8/2009 | Bennett et al. |
| 2009/0209620 A1 | 8/2009 | Wang et al. |
| 2009/0221551 A1 | 9/2009 | Kshirsagar et al. |
| 2009/0221556 A1 | 9/2009 | Kshirsagar et al. |
| 2009/0221631 A1 | 9/2009 | Jones et al. |
| 2009/0298821 A1 | 12/2009 | Kshirsagar et al. |
| 2009/0324551 A1 | 12/2009 | Carson et al. |
| 2009/0325877 A1 | 12/2009 | Grunt et al. |
| 2010/0075995 A1 | 3/2010 | Biggadike et al. |

(Continued)

FOREIGN PATENT DOCUMENTS

| | | |
|---|---|---|
| CN | 101203519 A | 6/2008 |
| EP | 1035123 B1 | 8/2003 |
| EP | 1147108 B1 | 8/2003 |
| EP | 1550662 A1 | 7/2005 |
| EP | 2132209 A1 | 12/2009 |
| EP | 2133353 A1 | 12/2009 |
| EP | 2138497 A1 | 12/2009 |
| JP | 07-330770 A | 12/1995 |
| JP | 1995330770 A | 6/1997 |
| JP | 11-180982 A | 7/1999 |

(Continued)

OTHER PUBLICATIONS

Hirota, et al., "Discovery of 8-Hydroxyadenines as a Novel Type of Interferon Inducer," *Journal of Medical Chemistry*, vol. 45, pp. 5419-5422 (2002).

(Continued)

*Primary Examiner* — Bruck Kifle
(74) *Attorney, Agent, or Firm* — Kilpatrick Townsend & Stockton LLP

(57) ABSTRACT

The present application includes novel modulators of TLRs, compositions containing such compounds, therapeutic methods that include the administration of such compounds.

12 Claims, No Drawings

(56) References Cited

U.S. PATENT DOCUMENTS

| | | | |
|---|---|---|---|
| 2010/0087443 A1 | 4/2010 | Bonnert et al. |
| 2010/0093998 A1 | 4/2010 | Isobe et al. |
| 2010/0099870 A1 | 4/2010 | Isobe et al. |
| 2010/0120799 A1 | 5/2010 | Lazarides et al. |
| 2010/0130491 A1 | 5/2010 | Bonnert et al. |
| 2010/0152230 A1 | 6/2010 | Dellaria, Jr. et al. |
| 2010/0210598 A1 | 8/2010 | Carson et al. |
| 2011/0028715 A1 | 2/2011 | Isobe et al. |
| 2011/0293654 A1 | 12/2011 | Griesgraber et al. |
| 2011/0295004 A1 | 12/2011 | Qian et al. |
| 2012/0035193 A1 | 2/2012 | Biggadike et al. |

FOREIGN PATENT DOCUMENTS

| | | |
|---|---|---|
| JP | 11-193282 A | 7/1999 |
| JP | 2000-159767 A | 6/2000 |
| JP | 1999180982 A | 1/2001 |
| JP | 1999193282 A | 1/2001 |
| JP | 2004-115416 A | 4/2004 |
| JP | 2004-137157 A | 5/2004 |
| JP | 2005-089334 A | 4/2005 |
| WO | 98/01448 A1 | 1/1998 |
| WO | 99/28321 A1 | 6/1999 |
| WO | 99/32122 A1 | 7/1999 |
| WO | 99/32477 A1 | 7/1999 |
| WO | 00/43394 A1 | 7/2000 |
| WO | 02/062767 A1 | 8/2002 |
| WO | 02/085905 A1 | 10/2002 |
| WO | 2004/029054 A1 | 4/2004 |
| WO | 2004/094372 A2 | 11/2004 |
| WO | 2004/106293 A2 | 12/2004 |
| WO | 2005/016348 A1 | 2/2005 |
| WO | 2005/016349 A1 | 2/2005 |
| WO | 2005/038056 A1 | 4/2005 |
| WO | 2005/039504 A2 | 5/2005 |
| WO | 2005/063264 A1 | 7/2005 |
| WO | 2005/067901 A2 | 7/2005 |
| WO | 2005/072088 A2 | 8/2005 |
| WO | 2005/079419 A2 | 9/2005 |
| WO | 2005/079506 A2 | 9/2005 |
| WO | 2005/087255 A2 | 9/2005 |
| WO | 2005/092892 A1 | 10/2005 |
| WO | 2005/092893 A1 | 10/2005 |
| WO | 2005/112935 A1 | 12/2005 |
| WO | 2005/117889 A1 | 12/2005 |
| WO | 2005/120511 A1 | 12/2005 |
| WO | 2006/089106 A2 | 8/2006 |
| WO | 2006/117670 A1 | 11/2006 |
| WO | 2007/024707 A2 | 3/2007 |
| WO | 2007/031726 A1 | 3/2007 |
| WO | 2007/034173 A1 | 3/2007 |
| WO | 2007/034817 A1 | 3/2007 |
| WO | 2007/034881 A1 | 3/2007 |
| WO | 2007/034882 A1 | 3/2007 |
| WO | 2007/034916 A1 | 3/2007 |
| WO | 2007/034917 A1 | 3/2007 |
| WO | 2007/089334 A2 | 8/2007 |
| WO | 2007/093901 A1 | 8/2007 |
| WO | 2007/119815 A1 | 10/2007 |
| WO | 2007/142755 A2 | 12/2007 |
| WO | 2008/004948 A1 | 1/2008 |
| WO | 2008/036747 A2 | 3/2008 |
| WO | 2008/071976 A1 | 6/2008 |
| WO | 2008/101867 A1 | 8/2008 |
| WO | 2008/114006 A1 | 9/2008 |
| WO | 2008/114008 A1 | 9/2008 |
| WO | 2008/114817 A1 | 9/2008 |
| WO | 2008/114819 A1 | 9/2008 |
| WO | 2008/115319 A2 | 9/2008 |
| WO | 2008/135791 A1 | 11/2008 |
| WO | 2009/019553 A2 | 2/2009 |
| WO | 2009/067081 A1 | 5/2009 |
| WO | 2009/078798 A1 | 6/2009 |
| WO | 2009/089900 A1 | 7/2009 |
| WO | 2009/118296 A2 | 10/2009 |
| WO | 2009/144009 A1 | 12/2009 |
| WO | 2010/017131 A2 | 2/2010 |
| WO | 2010/018130 A1 | 2/2010 |
| WO | 2010/018131 A1 | 2/2010 |
| WO | 2010/018132 A1 | 2/2010 |
| WO | 2010/018133 A1 | 2/2010 |
| WO | 2010/018134 A1 | 2/2010 |
| WO | 2010/048520 A1 | 4/2010 |
| WO | 2010/093436 A2 | 8/2010 |
| WO | 2010/133882 A1 | 11/2010 |
| WO | 2010/133885 A1 | 11/2010 |
| WO | 2011/017611 A1 | 2/2011 |
| WO | 2011/068233 A1 | 6/2011 |
| WO | 2011/098451 A1 | 8/2011 |
| WO | 2011/098452 A1 | 8/2011 |
| WO | 2011/136247 A1 | 11/2011 |

OTHER PUBLICATIONS

Hirota, et al., "Synthesis and Biological Evaluation of 2,8-Disubstituted 9-Benzyladenines: Discovery of 8-Mercaptoadenines as Potent Interferon-Inducers," *Bioorganic & Medicinal Chemistry Letters*, vol. 11, pp. 2715-2722 (2003).

Isobe, et al., "Synthesis and Structure—Activity Relationships of 2-Substituted-8-hydroxyadenine Derivatives as Orally Available Interferon Inducers without Emetic Side Effects," *Bioorganic & Medicinal Chemistry*, vol. 11, pp. 3641-3647 (2003).

Isobe, et al., "Synthesis and Biological Evaluation of Novel 9-Substituted-8-Hydroxyadenine Derivatives as Potent Interferon Inducers," *Journal of Medical Chemistry6*, vol. 49(6), pp. 2088-2095 (2006).

"Jin, G. et al. (2006)""Synthesis and immunostimulatory activity of 8-substituted amino 9-benzyladenines as potent Toll-like receptor 7 agonists," *Bioorganic & Medicinal Chemistry Letters* 16:4559-4563.

Jones, et al., "Discovery of a highly potent series of TLR7 agonists," *Bioorganic & Medicinal Chemistry Letters*, vol. 21, pp. 5939-5943 (2011).

Juricova et al. (1995) "Synthesis of Base-Modified 'Abbreviated' NAD Analogues," *Coll of Czechoslovak Chemical Communications* 60 (2), 237-250.

Kurimoto, et al., "Synthesis and Structure—Activity Relationships of 2-Amino-8-hydroxyadenines as Orally Active Interferon Inducing Agents," *Bioorganic & Medicinal Chemistry Letters*, vol. 11, pp. 5501-5508 (2003).

Kurimoto, et al., "Synthesis and evaluation of 2-substituted 8-hydroxyadenines as potent interferon inducers with improved oral bioavailabilities," *Bioorganic & Medicinal Chemistry Letters*, vol. 12, pp. 1091-1099 (2004).

Kurimoto, et al., "Prodrugs of 9-Benzyl-8-hydroxy-2-(2-hydroxyethylthio)adenine: Potent Interferon Inducing Agents in Monkeys," *Chem Pharm Bull.*, vol. 52(4), pp. 466-469 (2004).

Kurimoto, et al., "Synthesis and Biological Evaluation of 8-Oxoadenine Derivatives as Toll-like Receptor 7 Agonists Introducing the Antedrug Concept," *Journal of Medical Chemistry*, vol. 53, pp. 2964-2972 (2010).

Tran, et al., "Design and optimisation of orally active TLR7 agonists for the treatment of hepatitis C virus infection," *Bioorganic & Medicinal Chemistry Letters*, vol. 21, pp. 2389-2393 (2011).

International Search Report for PCT/US2008/007955, mailed on Oct. 22, 2008.

International Search Report from PCT/US2010/052802, mailed Feb. 10, 2011, 3 pages.

Office Action in Chile Application No. 988-2012 dated May 30, 2013 with English translation and reporting letter.

Office Action in Chile Application No. 988-2012 with reporting letter dated Jan. 8, 2014.

Office Action in Chinese Application No. 201080047895.4 dated Jan. 3, 2014 with English translation.

Office Action in Colombia Patent Application No. 12-067.317 with reporting letter dated Jul. 11, 2013 with English translation.

Office Action in Eurasia Application No. 201290131 with reporting letter dated Jun. 28, 2013 with English translation.

Office Action in Mexico Application No. MX/a/2012/004706 dated May 16, 2013 with English translation and reporting letter.

Office Action in Thailand Application No. 1201001820 dated Apr. 30, 2013 with English translation.

DERIVATIVES OF PURINE OR DEAZAPURINE USEFUL FOR THE TREATMENT OF (INTER ALIA) VIRAL INFECTIONS

FIELD OF THE INVENTION

This application relates generally to biaryl purine and 3-deazapurine derivatives and pharmaceutical compositions which selectively modulate toll-like receptors (such as TLR-7), and methods of making and using such compounds.

BACKGROUND OF THE INVENTION

The innate immune system provides the body with a first line defense against invading pathogens. In an innate immune response, an invading pathogen is recognized by a germline-encoded receptor, the activation of which initiates a signaling cascade that leads to the induction of cytokine expression. Innate immune system receptors have broad specificity, recognizing molecular structures that are highly conserved among different pathogens. One family of these receptors is known as Toll-like receptors (TLRs), due to their homology with receptors that were first identified and named in *Drosophila*, and are present in cells such as macrophages, dendritic cells, and epithelial cells.

There are at least ten different TLRs in mammals. Ligands and corresponding signaling cascades have been identified for some of these receptors. For example, TLR-2 is activated by the lipoprotein of bacteria (e.g., *E. coli*.), TLR-3 is activated by double-stranded RNA, TLR-4 is activated by lipopolysaccharide (i.e., LPS or endotoxin) of Gram-negative bacteria (e.g., *Salmonella* and *E. coli* O157:H7), TLR-5 is activated by flagellin of motile bacteria (e.g., *Listeria*), TLR-7 recognizes and responds to imiquimod (and ssRNA) and TLR-9 is activated by unmethylated CpG sequences of pathogen DNA. The stimulation of each of these receptors leads to activation of the transcription factor NF-κB, and other signaling molecules that are involved in regulating the expression of cytokine genes, including those encoding tumor necrosis factor-alpha (TNF-α), interleukin-1 (IL-1), and certain chemokines. Agonists of TLR-7 are immunostimulants and induce the production of endogenous interferon-α in vivo.

There are a number of diseases, disorders, and conditions linked to TLRs such that therapies using a TLR agonist are believed promising, including but not limited to melanoma, non-small cell lung carcinoma, hepatocellular carcinoma, basal cell carcinoma, renal cell carcinoma, myeloma, allergic rhinitis, asthma, COPD, ulcerative colitis, hepatic fibrosis, and viral infections such as HBV, HCV, HPV, RSV, SARS, HIV, or influenza.

SUMMARY OF THE INVENTION

In accordance with the foregoing, in one aspect the present invention provides compounds of Formula I:

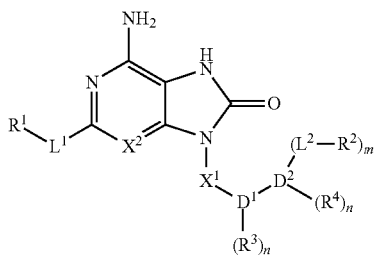

I or pharmaceutically acceptable salts thereof, wherein:
$L^1$ is —$NR^8$—, —O—, —S—, —$N(R^8)C(O)$—, —$S(O)_2$—, —S(O)—, or a covalent bond;
$R^1$ is H, alkyl, substituted alkyl, haloalkyl, alkenyl, substituted alkenyl, alkynyl, substituted alkynyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, substituted heterocyclylalkyl, aryl, substituted aryl, heteroaryl, substituted heteroaryl, arylalkyl, substituted arylalkyl, heteroarylalkyl, substituted heteroarylalkyl, carbocyclylalkenyl, substituted carbocyclylalkenyl, carbocyclylalkynyl, substituted carbocyclylalkynyl, heterocyclylalkenyl, substituted heterocyclylalkenyl, heterocyclylalkynyl, substituted heterocycloalkynyl, arylalkenyl, substituted arylalkenyl, arylalkynyl, substituted arylalkynyl, heteroarylalkenyl, substituted heteroarylalkenyl, heteroarylalkynyl, substituted heteroarylalkynyl, carbocyclylheteroalkyl, substituted carbocyclylheteroalkyl, heterocyclylheteroalkyl, substituted heterocyclylheteroalkyl, arylheteroalkyl, substituted arylheteroalkyl, heteroarylheteroalkyl, or substituted heteroarylheteroalkyl;
$X^2$ is N or C—$R^5$;
$R^5$ is H, halogen, alkyl, substituted alkyl, haloalkyl, alkoxy, substituted alkoxy, haloalkoxy, aminoalkyl, substituted aminoalkyl, alkenyl, substituted alkenyl, alkynyl, substituted alkynyl, heteroalkyl, substituted heteroalkyl, carbocyclyl, substituted carbocyclyl, carbocyclylalkyl, substituted carbocyclylalkyl, heterocyclyl, substituted heterocyclyl, aryl, substituted aryl, heteroaryl, substituted heteroaryl, heterocyclylalkyl, substituted heterocyclylalkyl, arylalkyl, substituted arylalkyl, heteroarylalkyl, substituted heteroarylalkyl, carbocyclylheteroalkyl, substituted carbocyclylheteroalkyl, heterocyclylheteroalkyl, substituted heterocyclylheteroalkyl, arylheteroalkyl, substituted arylheteroalkyl, heteroarylheteroalkyl, or substituted heteroarylheteroalkyl, cyano, azido, —C(O)H, —C(O)$R^8$, —S(O)$R^8$, —$S(O)_2R^8$, —$S(O)_2NR^8R^9$, —C(O)O$R^8$, or —C(O)$NR^9R^{10}$;
each non-hydrogen $R^5$ may optionally connect to $X^1$ to form an additional 5 to 8 membered carbocyclic or heterocyclic ring;
each non-hydrogen $R^5$ may optionally connect to $D^1$ to form an additional 5 to 8 membered carbocyclic or heterocyclic ring;
$X^1$ is alkylene, substituted alkylene, heteroalkylene, substituted heteroalkylene, alkenylene, substituted alkenylene, alkynylene, substituted alkynylene, carbocyclylene, substituted carbocyclylene, heterocyclylene, substituted heterocyclylene, —$NR^8$—, —O—, —C(O)—, —S(O)—, —$S(O)_2$—, or a covalent bond;
$D^1$ is aryl or heteroaryl;
$D^2$ is aryl or heteroaryl;
each $L^2$ is independently alkylene, substituted alkylene, heteroalkylene, substituted heteroalkylene, or a covalent bond;
each $R^2$ is independently —$NR^6R^7$;
m is 1 or 2;
each $R^3$ and $R^4$ is independently alkyl, substituted alkyl, alkenyl, substituted alkenyl, alkynyl, substituted alkynyl, halogen, haloalkyl, haloalkoxy, heteroalkyl, substituted heteroalkyl, =O, —O$R^8$, —S$R^8$, —$NR^9R^{10}$, =$NR^8$, =$NOR^8$, =$NNR^8R^9$, —CN, —OCN, —SCN, —N=C=O, —NCS, —NO, —$NO_2$, =$N_2$, —$N_3$, —$NR^8C(=O)R^9$, —$NR^8C(=O)OR^9$, —$NR^8C(=O)NR^9R^{10}$, —$C(=O)NR^9R^{10}$, —C(=O)O$R^8$, —OC(=O)$NR^9R^{10}$, —OC(=O)O$R^8$, —C(=O)$R^8$, —$S(=O)_2OR^8$, —$S(=O)_2R^8$, —OS$(=O)_2OR^8$, —$S(=O)_2NR^9R^{10}$, —$S(=O)R^8$, —$NR^8S(=O)_2R^9$, —$NR^8S(=O)_2NR^9R^{10}$, —$NR^8S(=O)_2OR^9$, —OS(O)$_2$NR$^9$R$^{10}$, —OP(=O)(OR$^8$)$_2$, —P(=O)(OR$^8$)$_2$, —P(O)(OR$^8$)(R$^9$), —P(O)R$^9$R$^{10}$, —OP(=O)R$^9$R$^{10}$, —C(=S)R$^8$, —C(=S)OR$^8$, —C(=O)SR$^8$, —C(=S)SR$^8$, —C(=S)NR$^9$R$^{10}$, —C(=NR$^8$)NR$^9$R$^{10}$, or —NR$^8$C(=NR$^8$)NR$^9$R$^{10}$;

each n is independently 0, 1, 2, 3, 4 or 5, depending on the size of the depicted ring D$^1$ and D$^2$, such that sufficient attachment points are present for each R$^3$ and R$^4$;

R$^6$ and R$^7$ are each independently H, alkyl, substituted alkyl, alkenyl, substituted alkenyl, alkynyl, substituted alkynyl, haloalkyl, heteroalkyl, substituted heteroalkyl, carbocyclyl, substituted carbocyclyl, carbocyclylalkyl, substituted carbocyclylalkyl, heterocyclyl, substituted heterocyclyl, aryl, substituted aryl, heteroaryl, substituted heteroaryl, heterocyclylalkyl, substituted heterocyclylalkyl, arylalkyl, substituted arylalkyl, heteroarylalkyl, substituted heteroarylalkyl, carbocyclylalkenyl, substituted carbocyclylalkenyl, carbocyclylalkynyl, substituted carbocyclylalkynyl, heterocyclylalkenyl, substituted heterocyclylalkenyl, heterocyclylalkynyl, substituted heteroalkynyl, arylalkenyl, substituted arylalkenyl, arylalkynyl, substituted arylalkynyl, heteroarylalkenyl, substituted heteroarylalkenyl, heteroarylalkynyl, substituted heteroarylalkynyl, carbocyclylheteroalkyl, substituted carbocyclylheteroalkyl, heterocyclylheteroalkyl, substituted heterocyclylheteroalkyl, arylheteroalkyl, substituted arylheteroalkyl, heteroarylheteroalkyl, or substituted heteroarylheteroalkyl, —C(O)H, —C(O)R$^8$, —S(O)R$^8$, —S(O)$_2$R$^8$, —C(O)OR$^8$, or —C(O)NR$^9$R$^{10}$, S(O)$_2$NR$^9$R$^{10}$; or R$^6$ and R$^7$, taken together with the nitrogen to which they are both attached, form a substituted or unsubstituted 3 to 8 membered heterocycle, which may contain one or more additional heteroatoms selected from N, O, S, or P; or R$^7$ taken together with L$^2$, and the N to which they are both attached, forms a substituted or unsubstituted 3 to 8 membered heterocycle which may contain one or more additional heteroatoms selected from N, O, S, or P; or R$^7$ taken together with D$^2$, L$^2$, and the N to which both R$^7$ and L$^2$ are attached forms a substituted or unsubstituted 5 to 15 membered heterocycle or heteroaryl which may contain one or more additional heteroatoms selected from N, O, S, or P;

R$^8$ is H, alkyl, substituted alkyl, haloalkyl, alkenyl, substituted alkenyl, alkynyl, substituted alkynyl, heteroalkyl, substituted heteroalkyl, carbocyclyl, substituted carbocyclyl, carbocyclylalkyl, substituted carbocyclylalkyl, heterocyclyl, substituted heterocyclyl, aryl, substituted aryl, heteroaryl, substituted heteroaryl, heterocyclylalkyl, substituted heterocyclylalkyl, arylalkyl, substituted arylalkyl, heteroarylalkyl, substituted heteroarylalkyl, carbocyclylalkenyl, substituted carbocyclylalkenyl, carbocyclylalkynyl, substituted carbocyclylalkynyl, heterocyclylalkenyl, substituted heterocyclylalkenyl, heterocyclylalkynyl, substituted heteroalkynyl, arylalkenyl, substituted arylalkenyl, arylalkynyl, substituted arylalkynyl, heteroarylalkenyl, substituted heteroarylalkenyl, heteroarylalkynyl, substituted heteroarylalkynyl, carbocyclylheteroalkyl, substituted carbocyclylheteroalkyl, heterocyclylheteroalkyl, substituted heterocyclylheteroalkyl, arylheteroalkyl, substituted arylheteroalkyl, heteroarylheteroalkyl, or substituted heteroarylheteroalkyl; and R$^9$ and R$^{10}$ are each independently H, alkyl, substituted alkyl, alkenyl, substituted alkenyl, alkynyl, substituted alkynyl, haloalkyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, substituted heterocyclylalkyl, aryl, substituted aryl, heteroaryl, substituted heteroaryl, heterocyclylalkyl, arylalkyl, substituted arylalkyl, heteroarylalkyl, substituted heteroarylalkyl, carbocyclylalkenyl, substituted carbocyclylalkenyl, carbocyclylalkynyl, substituted carbocyclylalkynyl, heterocyclylalkenyl, substituted heterocyclylalkenyl, heterocyclylalkynyl, substituted heterocyclylalkynyl, arylalkenyl, substituted arylalkenyl, arylalkynyl, substituted arylalkynyl, heteroarylalkenyl, substituted heteroarylalkenyl, heteroarylalkynyl, substituted heteroarylalkynyl, carbocyclylheteroalkyl, substituted carbocyclylheteroalkyl, heterocyclylheteroalkyl, substituted heterocyclylheteroalkyl, arylheteroalkyl, substituted arylheteroalkyl, heteroarylheteroalkyl, or substituted heteroarylheteroalkyl; or R$^9$ and R$^{10}$, taken together with the atom to which they are both attached, form a substituted or unsubstituted 3 to 8 membered heterocycle, which may contain one or more additional heteroatoms selected from N, O, S, or P.

Another aspect of the present invention includes a compound of the present invention and one or more pharmaceutically acceptable carrier or excipient. In a further embodiment, the composition further comprises one or more additional therapeutic agent.

Another aspect of the present invention includes a compound of the present invention in a method for treating a viral infection. In one embodiment, the treatment results in one or more of a reduction in viral load or clearance of viral RNA.

Another aspect of the present invention includes a compound of the present invention for use in the manufacture of a medicament for the treatment of a viral infection.

Another aspect of the present invention includes a compound of the present invention for the use in treating a viral infection.

In one embodiment, either such use or compound for treatment results in one or more of a reduction in viral load or clearance of RNA.

Another aspect of the present invention includes a compound of the present invention in a method for treating or preventing melanoma, non-small cell lung carcinoma, hepatocellular carcinoma, basal cell carcinoma, renal cell carcinoma, myeloma, allergic rhinitis, asthma, COPD, ulcerative colitis, hepatic fibrosis, HBV, HCV, HPV, RSV, SARS, HIV, or influenza.

Another aspect of the present invention includes a compound of the present invention for use in the manufacture of a medicament for the treatment or prevention of melanoma, non-small cell lung carcinoma, hepatocellular carcinoma, basal cell carcinoma, renal cell carcinoma, myeloma, allergic rhinitis, asthma, COPD, ulcerative colitis, hepatic fibrosis, HBV, HCV, HPV, RSV, SARS, HIV, or influenza.

While not wishing to be bound by theory, the inventors currently believe that the compounds of Formula I are agonists of TLR-7 and may also be agonists of other TLRs. Thus, compounds of the present invention can be used to treat or prevent diseases for which modulators of TLRs, and in particular TLR-7, exert a therapeutic effect. For example, such diseases include melanoma, non-small cell lung carcinoma, hepatocellular carcinoma, basal cell carcinoma, renal cell carcinoma, myeloma, allergic rhinitis, asthma, COPD, ulcerative colitis, hepatic fibrosis, HBV, HCV, HPV, RSV, SARS, HIV, and influenza.

As noted an aspect of the present invention includes a pharmaceutical composition comprising a compound of the present invention and one or more pharmaceutically acceptable carrier or excipient. The pharmaceutical composition of the present invention may further comprise one or more additional therapeutic agent. The one or more additional therapeutic agent may be, without limitation, selected from: interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, HCV NS4A inhibitors, HCV NS4B inhibitors, TLR-7 agonists, cyclophillin inhibitors, HCV IRES inhibitors, pharmacokinetic enhancers, and other drugs for treating HCV, or mixtures thereof.

As noted, an aspect of the present invention includes a method for treating a viral infection comprising administering a compound of the present invention. The compound is administered to a human subject in need thereof, such as a human being who is infected with a virus of the Flaviviridae family, such as hepatitis C virus. In one embodiment, the viral infection is acute or chronic HCV infection. In one embodiment, the treatment results in one or more of a reduction in viral load or clearance of RNA. As noted hereinabove, there are a number of diseases, disorders, and conditions linked to TLRs such that therapies using a TLR agonist are believed promising, including but not limited to melanoma, non-small cell lung carcinoma, hepatocellular carcinoma, basal cell carcinoma, renal cell carcinoma, myeloma, allergic rhinitis, asthma, COPD, ulcerative colitis, hepatic fibrosis, and viral infections such as HBV, HCV, HPV, RSV, SARS, HIV, or influenza As noted, an aspect of the present invention includes the use of a compound according to the present invention for the manufacture of a medicament for the treatment of a viral infection. Another aspect of the present invention includes a compound according to the present invention for the use in treating a viral infection. In one embodiment, the viral infection is acute or chronic HCV infection. In one embodiment, the treatment results in one or more of a reduction in viral load or clearance of RNA. In one embodiment, the viral infection is acute or chronic HBV infection. In one embodiment, the treatment results in one or more of a reduction in viral load or clearance of RNA.

The present invention includes combinations of aspects and embodiments, as well as preferences, as herein described throughout the present specification.

DETAILED DESCRIPTION

Reference will now be made in detail to certain claims of the invention, examples of which are illustrated in the accompanying structures and formulas. While the invention will be described in conjunction with the enumerated claims, it will be understood that they are not intended to limit the invention to those claims. On the contrary, the invention is intended to cover all alternatives, modifications, and equivalents, which may be included within the scope of the present invention as defined by the claims.

All documents referenced herein are each incorporated by reference in their entirety for all purposes.

DEFINITIONS

Unless stated otherwise, the following terms and phrases as used herein are intended to have the following meanings. The fact that a particular term or phrase is not specifically defined should not be correlated to indefiniteness or lacking clarity, but rather terms herein are used within their ordinary meaning. When trade names are used herein, applicants intend to independently include the tradename product and the active pharmaceutical ingredient(s) of the tradename product.

The term "treating", and grammatical equivalents thereof, when used in the context of treating a disease, means slowing or stopping the progression of a disease, or ameliorating at least one symptom of a disease, more preferably ameliorating more than one symptom of a disease. For example, treatment of a hepatitis C virus infection can include reducing the HCV viral load in an HCV infected human being, and/or reducing the severity of jaundice present in an HCV infected human being.

As used herein, "a compound of the invention" or "a compound of formula I" means a compound of formula I, including alternative forms thereof such as, solvated forms, hydrated forms, esterified forms, or physiologically functional derivatives thereof. Compounds of the invention also include tautomeric forms thereof, e.g., tautomeric "enols" as described herein. Similarly, with respect to isolatable intermediates, the phrase "a compound of formula (number)" means a compound of that formula and alternative forms thereof.

"Alkyl" is hydrocarbon containing normal, secondary, tertiary or cyclic carbon atoms. For example, an alkyl group can have 1 to 20 carbon atoms (i.e, $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —OtBu), and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like.

"Alkenyl" is a hydrocarbon containing normal, secondary, tertiary, or cyclic carbon atoms with at least one site of unsaturation, i.e. a carbon-carbon, sp2 double bond. For example, an alkenyl group can have 2 to 20 carbon atoms (i.e., $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of suitable alkenyl groups include, but are not limited to, vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkyne,), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1-ethylene (—CH($CH_3$)—), 1,2-ethylene (—$CH_2CH_2$—), 1,1-propylene (—CH($CH_2CH_3$)—), 1,2-propylene (—$CH_2$CH($CH_3$)—), 1,3-propylene (—$CH_2CH_2CH_2$—), 1,4-butylene (—$CH_2CH_2CH_2CH_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 2 to 20 carbon atoms, 2 to 10 carbon atoms, or 2 to 6 carbon atoms. Typical alkenylene radicals include, but are not limited to, 1,2-ethylene (—CH═CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 2 to 20 carbon atoms, 2 to 10 carbon atoms, or 2 to 6 carbon atoms. Typical alkynylene radicals include, but are not limited to, acetylene (—C≡C—), propargyl (—$CH_2$C≡C—), and 4-pentynyl (—$CH_2CH_2CH_2$C≡C—).

"Aminoalkyl" refers to an acyclic alkyl radical in which one of the hydrogen atoms bonded to a carbon atom, typically a terminal or sp3 carbon atom, is replaced with an amino radical.

"Amidoalkyl" refers to an acyclic alkyl radical in which one of the hydrogen atoms bonded to a carbon atom, typically a terminal or sp3 carbon atom, is replaced with a —$NR^aCOR^b$ group where $R^a$ is hydrogen or alkyl and $R^b$ is alkyl, substituted alkyl, aryl, or substituted aryl as defined herein, e.g., —$(CH_2)_2$—NHC(O)$CH_3$, —$(CH_2)_3$—NH—C(O)—$CH_3$, and the like.

"Aryl" means a monovalent aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl, and the like.

"Arylene" refers to an aryl as defined above having two monovalent radical centers derived by the removal of two hydrogen atoms from the same or two different carbon atoms of a parent aryl. Typical arylene radicals include, but are not limited to, phenylene.

"Arylalkyl" refers to an acyclic alkyl radical in which one of the hydrogen atoms bonded to a carbon atom, typically a terminal or sp3 carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or sp3 carbon atom, but also an sp2 carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 8 to 20 carbon atoms, e.g., the alkenyl moiety is 2 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or sp3 carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 8 to 20 carbon atoms, e.g., the alkynyl moiety is 2 to 6 carbon atoms and the aryl moiety is 6 to 14 carbon atoms.

"Halogen" refers to F, Cl, Br, or I.

As used herein, the term "haloalkoxy" refers to a group —$OR^a$, where $R^a$ is a haloalkyl group as herein defined. As non-limiting examples, haloalkoxy groups include —O($CH_2$)F, —O(CH)$F_2$, and —$OCF_3$.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, P, or S) the resulting heteroalkyl groups are, respectively, an alkoxy group (e.g., —$OCH_3$, etc.), an amine (e.g., —$NHCH_3$, —N($CH_3$)$_2$, and the like), or a thioalkyl group (e.g., —$SCH_3$). If a non-terminal carbon atom of the alkyl group which is not attached to the parent molecule is replaced with a heteroatom (e.g., O, N, P, or S) and the resulting heteroalkyl groups are, respectively, an alkyl ether (e.g., —$CH_2CH_2$—O—$CH_3$, etc.), an alkyl amine (e.g., —$CH_2NHCH_3$, —$CH_2$N($CH_3$)$_2$, and the like), or a thioalkyl ether (e.g., —$CH_2$—S—$CH_3$). If a terminal carbon atom of the alkyl group is replaced with a heteroatom (e.g., O, N, or S), the resulting heteroalkyl groups are, respectively, a hydroxyalkyl group (e.g., —$CH_2CH_2$—OH), an aminoalkyl group (e.g., —$CH_2NH_2$), or an alkyl thiol group (e.g., —$CH_2CH_2$—SH). A heteroalkyl group can have, for example, 1 to 20 carbon atoms, 1 to 10 carbon atoms, or 1 to 6 carbon atoms. A $C_1$-$C_6$ heteroalkyl group means a heteroalkyl group having 1 to 6 carbon atoms.

"Heterocycle" or "heterocyclyl" refers to a saturated or partially saturated cyclic group having from 1 to 14 carbon atoms and from 1 to 6 heteroatoms selected from N, S, P, or O, and includes single ring and multiple ring systems including, fused, bridged, and spiro ring systems. "Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and J. Am. Chem. Soc. (1960) 82:5566. In one embodiment, the carbon, nitrogen, phosphorous, or sulfur atom(s) of the heterocyclic group may be oxidized to provide for C(═O), N-oxide, phosphinane oxide, sulfinyl, or sulfonyl moieties.

As one example, substituted heterocyclyls include, for example, heterocyclic rings substituted with any of the substituents disclosed herein including oxo groups. A non-limiting example of a carbonyl substituted heterocyclyl is:

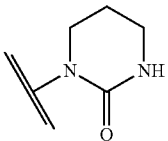

Examples of heterocycles include by way of example and not limitation dihydroypyridyl, tetrahydropyridyl (piperidyl), tetrahydrothiophenyl, sulfur oxidized tetrahydrothiophenyl, piperidinyl, 4-piperidonyl, pyrrolidinyl, azetidinyl, 2-pyrrolidonyl, tetrahydrofuranyl, decahydroquinolinyl, octahydroisoquinolinyl, pyranyl, morpholinyl, and bis-tetrahydrofuranyl:

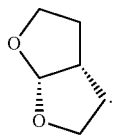

"Heterocyclylene" refers to a heterocyclyl, as defined herein, derived by replacing a hydrogen atom from a carbon atom or heteroatom of a heterocyclyl, with an open valence. Similarly, "heteroarylene" refers to an aromatic heterocyclylene.

"Heterocyclylalkyl" refers to an acyclic alkyl radical in which one of the hydrogen atoms bonded to a carbon atom, typically a terminal or sp3 carbon atom, is replaced with a heterocyclyl radical (i.e., a heterocyclyl-alkylene-moiety). Typical heterocyclyl alkyl groups include, but are not limited to heterocyclyl-$CH_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclylalkyl group comprises 2 to 20 carbon atoms and 1-6 heteroatoms, e.g., the alkyl portion of the heterocyclylalkyl group comprises 1 to 6 carbon atoms and the heterocyclyl moiety comprises 1 to 14 carbon atoms. Examples of heterocyclylalkyls include by way of example and not limitation 5-membered sulfur, oxygen, phosphorus, and/or nitrogen containing heterocycles such as pyrrolidiylmethyl, 2-tetrahydrofuranylylethan-1-yl, and the like, 6-membered sulfur, oxygen, and/or nitrogen containing heterocycles such as piperidinylmethyl, morpholinylmethyl, piperidinylethyl, teterahydropyranylethyl, and the like.

"Heterocyclylalkenyl" refers to an acyclic alkenyl radical in which one of the hydrogen atoms bonded to a carbon atom, typically a terminal or sp3 carbon atom, but also a sp2 carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclyl alkenyl group comprises 2 to 20 carbon atoms, e.g., the alkenyl portion of the heterocyclyl alkenyl group comprises 2 to 6 carbon atoms and the heterocyclyl moiety comprises 1 to 14 carbon atoms.

"Heterocyclylalkynyl" refers to an acyclic alkynyl radical in which one of the hydrogen atoms bonded to a carbon atom, typically a terminal or sp3 carbon atom, but also an sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclyl alkynyl group comprises 3 to 20 carbon atoms, e.g., the alkynyl portion of the heterocyclyl alkynyl group comprises 2 to 6 carbon atoms and the heterocyclyl moiety comprises 1 to 14 carbon atoms.

"Heteroaryl" refers to a monovalent aromatic heterocyclyl having at least one heteroatom in the ring. Thus, "heteroaryl" refers to an aromatic group of from 1 to 14 carbon atoms and 1 to 6 heteroatoms selected from oxygen, nitrogen, sulfur, or phosphorous. For multiple ring systems, by way of example, the term "heteroaryl" includes fused, bridged, and spiro ring systems having aromatic and non-aromatic rings. In one embodiment, the carbon, nitrogen, sulfur or phosphorus ring atom(s) of the heteroaryl group may be oxidized to provide for C(=O), N-oxide, sulfinyl, or sulfonyl moieties.

Examples of heteroaryls include by way of example and not limitation pyridyl, thiazolyl, pyrimidinyl, furanyl, thienyl, pyrrolyl, pyrazolyl, imidazolyl, tetrazolyl, benzofuranyl, thianaphthalenyl, indolyl, quinolinyl, isoquinolinyl, benzimidazolyl, tetrahydroquinolinyl, tetrahydroisoquinolinyl, 6H-1,2,5-thiadiazinyl, 2H,6H-1,5,2-dithiazinyl, thienyl, thianthrenyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

"Carbocycle" or "carbocyclyl" refers to a saturated, partially unsaturated or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo (4,5), (5,5), (5,6) or (6,6) system, or 9 or 10 ring atoms arranged as a bicyclo (5,6) or (6,6) system. Carbocycles include non-aromatic mono-, bi-, and poly-cyclic rings, whether fused, bridged, or spiro. Non-limiting examples of monocyclic carbocycles include cyclopropyl, cyclobutyl, cyclopentyl, 1-cyclopent-1-enyl, 1-cyclopent-2- enyl, 1-cyclopent-3-enyl, cyclohexyl, 1-cyclohex-1-enyl, 1-cyclohex-2-enyl, 1-cyclohex-3-enyl, and the like.

"Carbocyclylene" refers to a carbocyclyl or carbocycle as defined above having two monovalent radical centers derived by the removal of two hydrogen atoms from the same or two different carbon atoms of a parent carbocyclyl. Typical carbocyclylene radicals include, but are not limited to, phenylene.

"Arylheteroalkyl" refers to a heteroalkyl as defined herein, in which a hydrogen atom, which may be attached either to a carbon atom or a heteroatom, has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-S-aryl, -alkylene-S-alkylene-aryl, and the like. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —$CH_2$-pyridinyl, —$CH_2$-pyrrolyl, —$CH_2$-oxazolyl, —$CH_2$-indolyl, —$CH_2$-purinyl, —$CH_2$-furanyl, —$CH_2$-thienyl, —$CH_2$-benzofuranyl, —$CH_2$-benzothiophenyl, —$CH_2$-carbazolyl, —$CH_2$-thiazolyl, —$CH_2$-isoxazolyl, —$CH_2$-pyrazolyl, —$CH_2$-isothiazolyl, —$CH_2$-pyridazyl, —$CH_2$-pyrimidyl, —$CH_2$-pyrazyl, —$CH(CH_3)$-pyridinyl, —$CH(CH_3)$-pyrrolyl, —$CH(CH_3)$-oxazolyl, —$CH(CH_3)$-indolyl, —$CH(CH_3)$-isoindolyl, —$CH(CH_3)$-purinyl, —$CH(CH_3)$-furanyl, —$CH(CH_3)$-thienyl, —$CH(CH_3)$-benzofuranyl, —$CH(CH_3)$-benzothiophenyl, —$CH(CH_3)$-carbazolyl, —$CH(CH_3)$-imidazolyl, —$CH(CH_3)$-thiazolyl, —$CH(CH_3)$-isoxazolyl, —$CH(CH_3)$-pyrazolyl, —$CH(CH_3)$-isothiazolyl, —$CH(CH_3)$-quinolyl, —$CH(CH_3)$-isoquinolyl, —$CH(CH_3)$-pyridazyl, —$CH(CH_3)$-pyrimidyl, —$CH(CH_3)$-pyrazyl, and the like.

The term "optionally substituted" in reference to a particular moiety of the compound of the Formulae of the invention, for example an optionally substituted aryl group, refers to a moiety having 0, 1, or more substituents.

The term "substituted" in reference to alkyl, aryl, arylalkyl, carbocyclyl, heterocyclyl, and other groups used herein, for example, "substituted alkyl", "substituted aryl", "substituted arylalkyl", "substituted heterocyclyl", and "substituted carbocyclyl" means a group, alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —R, —O—, =O, —OR, —SR, —S—, —$NR_2$, —$N(+)R_3$, =NR, =NOR, =$NNR_2$, —$CX_3$, —$CRX_2$, —$CR_2X$, —CN, —OCN, —SCN, —N=C=O, —NCS, —NO, —$NO_2$, =$N_2$, —$N_3$, —NRC(=O)R, —NRC(=O)OR, —NRC(=O)NRR, —C(=O)NRR, —C(=O)OR, —OC(=O)NRR, —OC(=O)OR, —C(=O)R, —$S(=O)_2$OR, —$S(=O)_2$R, —$OS(=O)_2$OR, —$S(=O)_2$NRR, —S(=O)R, —$NRS(=O)_2$R, —$NRS(=O)_2$NRR, —$NRS(=O)_2$OR, —OP(=O)$(OR)_2$, —P(=O)$(OR)_2$, —P(O)(OR)(R), —OP(=O)$R_2$, —P(=O)$R_2$, —C(=S)R, —C(=S)OR, —C(=O)SR, —C(=S)SR, —C(=S)NRR, —C(=NR)NRR, —NRC(=NR)NRR, where each X is independently a halogen: F, Cl, Br, or I; and each R is independently H, alkyl, aryl, arylalkyl, a heterocycle, or a protecting group or prodrug moiety. Divalent groups may also be similarly substituted.

Those skilled in the art will recognize that when moieties such as "alkyl", "aryl", "heterocyclyl", etc. are substituted with one or more substituents, they could alternatively be referred to as "alkylene", "arylene", "heterocyclylene", etc. moieties (i.e., indicating that at least one of the hydrogen atoms of the parent "alkyl", "aryl", "heterocyclyl" moieties has been replaced with the indicated substituent(s)). When moieties such as "alkyl", "aryl", "heterocyclyl", etc. are referred to herein as "substituted" or are shown diagrammatically to be substituted (or optionally substituted, e.g., when the number of substituents ranges from zero to a positive integer), then the terms "alkyl", "aryl", "heterocyclyl", etc. are understood to be interchangeable with "alkylene", "arylene", "heterocyclylene", etc.

Further, those skilled in the art will recognize that when terms herein defined are used in combination, the resulting combined term is used according to the definition. For example, although a term such as "carbocyclylheteroalkyl" may not carry a specific definition herein should not be equated to a lack of clarity. Rather, such a term is used within the accepted meaning in the art to describe a carbocyclyl group linked via a heteroalkyl group. Other such terms are used consistently.

As will be appreciated by those skilled in the art, the compounds of the present invention are capable of existing in solvated or hydrated form. The scope of the present invention includes such forms. Again, as will be appreciated by those skilled in the art, the compounds may be capable of esterification. The scope of the present invention includes esters and other physiologically functional derivatives. The scope of the present invention also includes tautomeric forms, namely, tautomeric "enols" as herein described. In addition, the scope of the present invention includes prodrug forms of the compound herein described.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds of Formula I should be selected in order to provide a compound which is sufficiently stable to provide a pharmaceutically useful compound which can be formulated into an acceptably stable pharmaceutical composition. Compounds of Formula I which have such stability are contemplated as falling within the scope of the present invention.

As will be appreciated by those skilled in the art, the compounds of the present invention may contain one or more chiral centers. The scope of the present invention includes such forms. Again, as will be appreciated by those skilled in the art, the compound is capable of esterification or hydrolysis. The scope of the present invention includes esters and other physiologically functional derivatives. The scope of the present invention also includes tautomeric forms, namely, tautomeric "enols" as herein described. In addition, the scope of the present invention includes prodrug forms of the compound herein described.

The compounds of the present invention may crystallize in more than one form, a characteristic known as polymorphism, and such polymorphic forms ("polymorphs") are within the scope of the present invention. Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by the formulae of the present invention, as well as any wholly or partially equilibrated mixtures thereof. The present invention also includes the individual isomers of the compounds represented by the formulas above as mixtures with isomers thereof in which one or more chiral centers are inverted.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The present invention includes a salt or solvate of the compounds herein described, including combinations thereof such as a solvate of a salt. The compounds of the present invention may exist in solvated, for example hydrated, as well as unsolvated forms, and the present invention encompasses all such forms.

Typically, but not absolutely, the salts of the present invention are pharmaceutically acceptable salts. Salts encompassed within the term "pharmaceutically acceptable salts" refer to non-toxic salts of the compounds of this invention.

Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene and Peter G. M. Wuts (John Wiley & Sons, Inc., New York, 1999, ISBN 0-471-16019-9) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-Forming Protecting Groups

Ester-forming groups include: (1) phosphonate ester-forming groups, such as phosphonamidate esters, phosphorothioate esters, phosphonate esters, and phosphon-bis-amidates;

(2) carboxyl ester-forming groups, and (3) sulphur ester-forming groups, such as sulphonate, sulfate, and sulfinate.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti-infective activity of their own.

Compounds of Formula I

The definitions and substituents for various genus and subgenus of the present compounds are described and illustrated herein. It should be understood by one skilled in the art that any combination of the definitions and substituents described above should not result in an inoperable species or compound. "Inoperable species or compounds" means compound structures that violates relevant scientific principles (such as, for example, a carbon atom connecting to more than four covalent bonds) or compounds too unstable to permit isolation and formulation into pharmaceutically acceptable dosage forms.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 2 to about 11, but is ordinarily about 7 to 10.

While it is possible for the active ingredients to be administered alone it may be preferable to present them as pharmaceutical formulations. The formulations of the invention, both for veterinary and for human use, comprise at least one active ingredient, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 µm (including particle sizes in a range between 0.1 and 500 µm in increments such as 0.5 µm, 1 µm, 30 µm, 35 µm, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

The effective dose of an active ingredient depends at least on the nature of the condition being treated, toxicity, whether the compound is being used prophylactically (lower doses) or against an active disease or condition, the method of delivery, and the pharmaceutical formulation, and will be determined by the clinician using conventional dose escalation studies. The effective dose can be expected to be from about 0.0001 to about 1000 mg/kg body weight per day. For example, the daily candidate dose for an adult human of approximately 70 kg body weight will range from about 0.05 mg to about 100 mg, or between about 0.1 mg and about 25 mg, or between about 0.4 mg and about 4 mg, and may take the form of single or multiple doses.

In yet another embodiment, the present application discloses pharmaceutical compositions comprising a compound of Formula I or a pharmaceutically acceptable salt thereof, and a pharmaceutically acceptable carrier or exipient.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

In one embodiment, the compounds of the present invention are used in combination with an additional active therapeutic ingredient or agent.

In one embodiment, combinations of the compounds of Formula I, and additional active agents may be selected to treat patients with a viral infection, for example, HBV, HCV, or HIV infection.

Useful active therapeutic agents for HBV include reverse transcriptase inhibitors, such as lamivudine (Epivir®), adefovir (Hepsera®), tenofovir (Viread®), telbivudine (Tyzeka®), entecavir (Baraclude®), and Clevudine®. Other useful active therapeutic agents include immunomodulators, such as interferon alpha-2b (Intron A®), pegylated interferon alpha-2a (Pegasys®), interferon alpha 2a (Roferon®), interferon alpha N1, prednisone, predinisolone, Thymalfasin®, retinoic acid receptor agonists, 4-methylumbelliferone, Alamifovir®, Metacavir®, Albuferon®, agonists of TLRs (e.g., TLR-7 agonists), and cytokines.

With regard to treatment for HCV, non-limiting examples of suitable combinations include combinations of one or more compounds of the present invention with one or more interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophilin inhibitors, HCV IRES inhibitors, pharmacokinetic enhancers, and other drugs for treating HCV.

More specifically, one or more compounds of the present invention may be combined with one or more compounds selected from the group consisting of 1) interferons, e.g., pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha- 2b (Albuferon), IFN alpha XL, BLX-883 (Locteron), DA-3021, glycosylated interferon alpha-2b (AVI-005), PEG-Infergen, PEGylated interferon lambda (PEGylated IL-29), and belerofon, 2) ribavirin and its analogs, e.g., ribavirin (Rebetol, Copegus), and taribavirin (Viramidine), 3) HCV NS3 protease inhibitors, e.g., boceprevir (SCH-503034, SCH-7), telaprevir (VX-950), VX-813, TMC-435 (TMC435350), ABT-450, BI-201335, BI-1230, MK-7009, SCH-900518, VBY-376, VX-500, GS-9256, GS-9451, BMS-790052, BMS-605339, PHX-1766, AS-101, YH-5258, YH5530, YH5531, and ITMN-191 (R-7227), 4) alpha-glucosidase 1 inhibitors, e.g., celgosivir (MX-3253), Miglitol, and UT-231B, 5) hepatoprotectants, e.g., emericasan (IDN-6556), ME-3738, GS-9450 (LB-84451), silibilin, and MitoQ, 6) nucleoside or nucleotide inhibitors of HCV NS5B polymerase, e.g., R1626, R7128 (R4048), IDX184, IDX-102, PSI-7851, BCX-4678, valopicitabine (NM-283), and MK-0608, 7) non-nucleoside inhibitors of HCV NS5B polymerase, e.g., filibuvir (PF-868554), ABT-333, ABT-072, BI-207127, VCH-759, VCH-916, JTK-652, MK-3281, VBY-708, VCH-222, A848837, ANA-598, GL60667, GL59728, A-63890, A-48773, A-48547, BC-2329, VCH-796 (nesbuvir), GSK625433, BILN-1941, XTL-2125, and GS-9190, 8) HCV NS5A inhibitors, e.g., AZD-2836 (A-831), AZD-7295 (A-689), and BMS-790052, 9) TLR-7 agonists, e.g., imiquimod, 852A, GS-9524, ANA-773, ANA-975, AZD-8848 (DSP-3025), PF-04878691, and SM-360320, 10) cyclophillin inhibitors, e.g., DEBIO-025, SCY-635, and NIM811, 11) HCV IRES inhibitors, e.g., MCI-067, 12) pharmacokinetic enhancers, e.g., BAS-100, SPI-452, PF-4194477, TMC-41629, GS-9350, GS-9585, and roxythromycin, 13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, FK-788, and VX-497 (merimepodib).

In addition, the compounds of the invention may be employed in combination with other therapeutic agents for the treatment or prophylaxis of HIV or AIDS and/or one or more other diseases present in a human subject suffering from HIV or AIDS (e.g., bacterial and/or fungal infections, other viral infections such as hepatitis B or hepatitis C, or cancers such as Kaposi's sarcoma). The additional therapeutic agent(s) may be coformulated with one or more salts of the invention (e.g., coformulated in a tablet).

In one embodiment, non-limiting examples of suitable combinations include combinations of one or more compounds of the present invention with one or more HIV protease inhibitors, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, CCR8 inhibitors, RNase H inhibitors, maturation inhibitors, pharmacokinetic enhancers, and other drugs for treating HIV.

More specifically, one or more compounds of the present invention may be combined with one or more compounds selected from the group consisting of 1) HIV protease inhibitors, e.g., amprenavir (Agenerase), atazanavir (Reyataz), fosamprenavir (Lexiva), indinavir (Crixivan), lopinavir, ritonavir (norvir), nelfinavir (Viracept), saquinavir (Invirase), tipranavir (Aptivus), brecanavir, darunavir (Prezista), TMC-126, TMC-114, mozenavir (DMP-450), JE-2147 (AG1776), L-756423, R00334649, KNI-272, DPC-681, DPC-684, DG17, GS-8374, MK-8122 (PPL-100), DG35, and AG 1859, SPI-256, TMC 52390, PL-337, SM-322377, SM-309515, GRL-02031, CRS-074, CRS-075, KB-98, and A-790742, 2) HIV non-nucleoside inhibitors of reverse transcriptase, e.g., capravirine, emivirine, delaviridine (Rescriptor), efavirenz (Sustiva), nevirapine (Viramune), (+)-calanolide A, calanolide B, etravirine (Intelence), GW5634, DPC-083, DPC-961, DPC-963, MIV-150, MIV-160, MIV-170, dapivirine (TMC-120), rilpivirine (TMC-278), BILR 355 BS, VRX 840773, UK-453061, and RDEA806, RDEA 427, RDEA 640, IDX 899, ANX-201 (Thiovir), R-1206, LOC-dd, IQP-0410 (SJ-3366), YM-215389, YM-228855, CMX-052, and CMX-182, 3) HIV nucleoside inhibitors of reverse transcriptase, e.g., zidovudine (Retrovir), emtricitabine (Emtriva), didanosine (Videx), stavudine (Zerit), zalcitabine (Hivid), lamivudine (Epivir), abacavir (Ziagen), amdoxovir, elvucitabine (ACH 126443), alovudine (MIV-310), MIV-210, racivir (racemic FTC, PSI-5004), D-d4FC, phosphazide, fozivudine tidoxil, apricitibine (AVX754, SPD-754), GS-7340, KP-1461, AVX756, OBP-601, dioxolane thymine, TMC-254072, INK-20, PPI-801, PPI-802, MIV-410, 4'-Ed4T, B-108, and fosalvudine tidoxil (HDP 99.0003), 4) HIV nucleotide inhibitors of reverse transcriptase, e.g., tenofovir disoproxil fumarate (Viread), and adefovir dipivoxil, 5) HIV integrase inhibitors, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, raltegravir (Isentress, MK-0518), elvitegravir (GS-9137), BMS-538158, GSK364735C, BMS-707035, MK-2048, GSK-349572 (S-349572), GSK-265744 (S-265744), GSK-247303 (S-247303), S-1360 (GW810871), 1,5-DCQA, INH-001, INT-349, V-165, RIN-25, BFX-1001, BFX-1002, BFX-1003, RSC-1838, BCH-33040, and BA 011, 6) gp41 inhibitors, e.g., enfuvirtide (Fuzeon), sifuvirtide, MPI-451936, FB006M, A-329029, and TRI-1144, 7) CXCR4 inhibitors, e.g., AMD-070, KRH-3955 (CS-3955), AMD-9370, AMD-3451, RPI-MN, MSX-122, and POL-2438, 8) entry inhibitors, e.g., SP01A, PA-161, SPC3, TNX-355, DES6, SP-10, SP-03, CT-319, and CT-326, 9) gp120 inhibitors, e.g., BMS-488043 and its prodrugs, BlockAide/CR, KPC-2, and MNLP62, 10) G6PD and NADH-oxidase inhibitors, e.g., immunitin, 11) CCR5 inhibitors, e.g., aplaviroc, nifeviroc, vicriviroc (SCH-417690), maraviroc (Selzentry), PRO-140, PRO-542, INCB15050, INCB9471, PF-232798, SCH-532706, GSK-706769, TAK-652, TAK-220, ESN-196, RO-1752, ZM-688523, AMD-887, YM-370749, NIBR-1282, SCH-350634, ZM-688523, and CCR5mAb004, 12) CCR8 inhibitors, e.g., ZK-756326, 13) RNase H inhibitors, e.g., ODN-93, and ODN-112, 14) maturation inhibitors, e.g., bevirimat (PA-457), PA-040, MPC-9055 (vicecon, MPI-49839), ACH-100703, ACH-100706

15) pharmacokinetic enhancers, e.g., BAS-100, SPI-452, PF-4194477, TMC-41629, GS-9350, GS-9585, and roxythromycin, 16) other drugs for treating HIV, e.g., REP 9, SP-01A, TNX-355, DES6, ODN-93, ODN-112, VGV-1, Ampligen, HRG214, Cytolin, VGX-410, VGX-820, KD-247, AMZ 0026, CYT 99007, A-221 HIV, HPH-116, DEBIO-025, BAY 50-4798, MDX010 (ipilimumab), PBS 119, BIT-225, UBT-8147, ITI-367, AFX-400, BL-1050, GRN-139951, GRN-140665, AX-38679, RGB-340638, PPI-367, and ALG 889.

Where the disorder is cancer, combination with at least one other anticancer therapy is envisaged. In particular, in anticancer therapy, combination with other anti-neoplastic agent (including chemotherapeutic, hormonal or antibody agents) is envisaged as well as combination with surgical therapy and radiotherapy. Combination therapies according to the present invention thus comprise the administration of at least one compound of formula (I) or a salt or solvate thereof, and the use of at least one other cancer treatment method. Preferably, combination therapies according to the present invention comprise the administration of at least one compound of formula (I) or a salt or solvate thereof, and at least one other pharmaceutically active agent, preferably an anti-neoplastic agent. The compound(s) of formula (I)) and the other pharmaceutically active agent(s) may be administered together or separately and, when administered separately this may occur simultaneously or sequentially in any order (including administration on different days according to the therapy regimen) and by any convenient route. The amounts of the compound(s) of formula (I) and the other pharmaceutically active agent(s) and the relative timings of administration will be selected in order to achieve the desired combined therapeutic effect.

In one embodiment, the further anti-cancer therapy is at least one additional antineoplastic agent. Any anti-neoplastic agent that has activity versus a susceptible tumor being treated may be utilized in the combination. Typical anti-neoplastic agents useful include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; nonreceptor tyrosine kinase angiogenesis inhibitors; immunotherapeutic agents; proapoptotic agents; and cell cycle signaling inhibitors.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. Paclitaxel has been approved for clinical use in the treatment of refractory ovarian cancer in the United States (Markman et al., Yale Journal of Biology and Medicine, 64:583, 1991; McGuire et al., Ann. Intern, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R J. et. al, Cancer Chemotherapy Pocket Guide$_4$ 1998) related to the duration of dosing above a threshold concentration (50 nM) (Kearns, C M. et. al., Seminars in Oncology, 3(6) p. 16-23, 1995).

Docetaxel, (2R,3S)— N-carboxy-3-phenylisoserine,N-te/f-butyl ester, 13-ester with 5β-20-epoxy-1,2α,4,7β,10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine. Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, oxaliplatin, cisplatin and carboplatin. Cisplatin, cis-diamminedichloroplatinum, is commercially available as PLATINOL® as an injectable solution. Cisplatin is primarily indicated in the treatment of metastatic testicular and ovarian cancer and advanced bladder cancer. Carboplatin, platinum, diammine[1,1-cyclobutane-dicarboxylate(2-)-O,O'], is commercially available as PARAPLATIN® as an injectable solution. Carboplatin is primarily indicated in the first and second line treatment of advanced ovarian carcinoma.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine. Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan. Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Busulfan, 1,4-butanediol dimethanesulfonate, is commercially available as MYLERAN® TABLETS. Busulfan is indicated for the palliative treatment of chronic myelogenous leukemia. Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease.

Antibiotic anti-neoplasties are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins. Dactinomycin, also know as Actinomycin D, is commercially available in injectable form as COSMEGEN®. Dactinomycin is indicated for the treatment of Wilm's tumor and rhabdomyosarcoma. Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblasts leukemia, but is also a useful component in the treatment of some solid tumors and lymphomas. Bleomycin, a mixture of cytotoxic glycopeptide antibiotics isolated from a strain of *Streptomyces verticillus*, is commercially available as BLENOXAN Bleomycin is indicated as a palliative treatment, as a single agent or in combination with other agents, of squamous cell carcinoma, lymphomas, and testicular carcinomas.

Topoisomerase II inhibitors include, but are not limited to, epipodophyllotoxins. Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide. Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine. 5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (IH)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. A useful mercaptopurine analog is azathioprine. Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Other purine analogs include pentostatin, erythrohydroxynonyladenine, fludarabine phosphate, and cladribine. Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Methotrexate, N-[4[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below. Irinotecan HCl, (4S)-4,11-diethyl-4-hydroxy-9-[(4-piperidinopiperidino)carbonyloxy]-1H-pyrano[3',4',6,7]indolizino[1,2-b]quinoline-3,14(4H,12H)-dione hydrochloride, is commercially available as the injectable solution CAMPTOSAR®. Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I: DNA: irintecan or SN-38 ternary complex with replication enzymes. Irinotecan is indicated for treatment of metastatic cancer of the colon or rectum. Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and luprolide.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, ret, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C, Exp. Opin. Ther. Patents (2000)

10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed nonreceptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404. SH2/SH3 domain blockers are agents that disrupt SH2 or SH3 domain binding in a variety of enzymes or adaptor proteins including, PI3-K p85 subunit, Src family kinases, adaptor molecules (She, Crk, Nek, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myo-inositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancererbB Family Receptor Tyrosine Kniases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Anti-angiogenic agents including non-receptorkinase angiogenesis inhibitors may alo be useful. Anti-angiogenic agents such as those which inhibit the effects of vascular edothelial growth factor, (for example the anti-vascular endothelial cell growth factor antibody bevacizumab [Avastin™], and compounds that work by other mechanisms (for example linomide, inhibitors of integrin $\alpha v\beta 3$ function, endostatin and angiostatin).

Agents used in immunotherapeutic regimens may also be useful in combination with the compounds of formula (I). Immunotherapy approaches, including for example ex-vivo and in-vivo approaches to increase the immunogenecity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Agents used in proapoptotic regimens (e.g., bcl-2 antisense oligonucleotides) may also be used in the combination of the present invention.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

For the treatment or prophylaxis of pulmonary disorders, anticholinergics of potential use in treating asthma, COPD, bronchitis, and the like, and therefore useful as an additional therapeutic agent include antagonists of the muscarinic receptor (particularly of the M3 subtype) which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2-carboxylic acid (1-methyl-piperidin-4-ylmethyl)-amide; 3-[3-(2-Diethylamino-acetoxy)-2-phenyl-propionyloxy]-8-isopropyl-8-methyl-8-azonia-bicyclo [3.2.1]octane (Ipratropium-N,N-diethylglycinate); 1-Cyclohexyl-3,4-dihydro-1H-isoquinoline-2-carboxylic acid 1-aza-bicyclo[2.2.2]oct-3-yl ester (Solifenacin); 2-Hydroxymethyl-4-methanesulfinyl-2-phenyl-butyric acid 1-aza-bicyclo[2.2.2]oct-3-yl ester (Revatropate); 2-{1-[2-(2,3-Dihydro-benzofuran-5-yl)-ethyl]-pyrrolidin-3-yl}-2,2-diphenyl-acetamide (Darifenacin); 4-Azepan-1-yl-2,2-diphenyl-butyramide (Buzepide); 7-[3-(2-Diethylamino-acetoxy)-2-phenyl-propionyloxy]-9-ethyl-9-methyl-3-oxa- 9-azonia-tricyclo[3.3.1.02,4]nonane (Oxitropium-N,N-diethylglycinate); 7-[2-(2-Diethylamino-acetoxy)-2,2-di-thiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methyl-phenyl ester (Tolterodine-N,N-dimethylglycinate); 3-[4,4-Bis-(4-fluoro-phenyl)-2-oxo-imidazolidin-1-yl]-1-methyl-1-(2-oxo-2-py-ridin-2-yl-ethyl)-pyrrolidinium; 1-[1-(3-Fluoro-benzyl)-pip-eridin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl-acetoxy]-1-(3-phenoxy-propyl)-1-azo-nia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)-piperidin-4-ylester; beta-2 agonist used to treat broncho-constriction in asthma, COPD and bronchitis include salmeterol and albuterol; anti-inflammatory signal transduction modulators for asthma.

With regard to the pulmonary condition of asthma, those skilled in the art appreciate that asthma is a chronic inflammatory disease of the airways resulting from the infiltration of pro-inflammatory cells, mostly eosinophils and activated T-lymphocytes into the bronchial mucosa and submucosa. The secretion of potent chemical mediators, including cytokines, by these proinflammatory cells alters mucosal permeability, mucus production, and causes smooth muscle contraction. All of these factors lead to an increased reactivity of the airways to a wide variety of irritant stimuli (Kaliner, 1988). Targeting signal transduction pathways is an attractive approach to treating inflammatory diseases, as the same pathways are usually involved in several cell types and regulate several coordinated inflammatory processes, hence modulators have the prospect of a wide spectrum of beneficial effects. Multiple inflammatory signals activate a variety of cell surface receptors that activate a limited number of signal transduction pathways, most of which involve cascades of kinases. These kinases in turn may activate transcription factors that regulate multiple inflammatory genes. Applying "anti-inflammatory signal transduction modulators" (referred to in this text as AISTM), like phosphodiesterase inhibitors (e.g. PDE-4, PDE-5, or PDE-7 specific), transcription factor inhibitors (e.g. blocking NFκB through IKK inhibition), or kinase inhibitors (e.g. blocking P38 MAP, JNK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006).

Additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast); 4-[2-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[(methylsulfonyl)amino]-1-dibenzofurancarboxamide (PDE-4 inhibitor Oglemilast); N-(3,5-Dichloro-pyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591); 4-[5-(4-Fluorophenyl)-2-(4-methanesulfinyl-phenyl)-1H-imidazol-4-yl]-pyridine (P38 inhibitor SB-203850); 4-[4-(4-Fluorophenyl)-1-(3-phenyl-propyl)-5-pyridin-4-yl-1H-imidazol-2-yl]-but-3-yn-1-ol (P38 inhibitor RWJ-67657); 4-Cyano-4-(3-cyclopentyloxy-4-methoxy-phenyl)-cyclohexanecarboxylic acid 2-diethylamino-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]-amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

Moreover, asthma is a chronic inflammatory disease of the airways produced by the infiltration of pro-inflammatory cells, mostly eosinophils and activated T-lymphocytes (Poston, Am. Rev. Respir. Dis., 145 (4 Pt 1), 918-921, 1992; Walker, J. Allergy Clin. Immunol., 88 (6), 935-42, 1991) into the bronchial mucosa and submucosa. The secretion of potent chemical mediators, including cytokines, by these proinflammatory cells alters mucosal permeability, mucus production, and causes smooth muscle contraction. All of these factors lead to an increased reactivity of the airways to a wide variety of irritant stimuli (Kaliner, "Bronchial asthma, Immunologic diseases" E. M. Samter, Boston, Little, Brown and Company: 117-118. 1988).

Glucocorticoids, which were first introduced as an asthma therapy in 1950 (Carryer, Journal of Allergy, 21, 282-287, 1950), remain the most potent and consistently effective therapy for this disease, although their mechanism of action is not yet fully understood (Morris, J. Allergy Clin. Immunol., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, 10th edition, 2001). A solution to systemic side effects is to deliver steroid drugs directly to the site of inflammation. Inhaled corticosteroids (ICS) have been developed to mitigate the severe adverse effects of oral steroids. While ICS are very effective in controlling inflammation in asthma, they too are not precisely delivered to the optimal site of action in the lungs and produce unwanted side effects in the mouth and pharynx (candidiasis, sore throat, dysphonia). Combinations of inhaled β2-adrenoreceptor agonist bronchodilators such as formoterol or salmeterol with ICS's are also used to treat both the bronchoconstriction and the inflammation associated with asthma and COPD (Symbicort® and Advair®, respectively). However, these combinations have the side effects of both the ICS's and the β2-adrenoreceptor agonist because of systemic absorption (tachycardia, ventricular dysrhythmias, hypokalemia) primarily because neither agent is delivered to the optimal sites of actions in the lungs. In consideration of all problems and disadvantages connected with the adverse side effect profile of ICS and of β2-agonists it would be highly advantageous to provide mutual steroid-β2-agonist prodrug to mask the pharmacological properties of both steroids and β2-agonists until such a prodrug reaches the lungs, thereby mitigating the oropharyngeal side effects of ICS and cardiovascular side-effects of β2-agonists. In one aspect, such a mutual steroid-β2-agonist prodrug would be effectively delivered to the endobronchial space and converted to active drugs by the action of lung enzymes, thereby delivering to the site of inflammation and bronchoconstriction a therapeutic amount of both drugs. An anti-inflammatory agent for combination therapy includes dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diproprionate, methylprednisolone, fluocinolone, fluocinolone acetonide, flunisolide, fluocortin-21-butylate, flumethasone, flumetasone pivalate, budesonide, halobetasol propionate, mometasone furoate, fluticasone propionate, ciclesonide; or a pharmaceutically acceptable salt thereof.

In yet another embodiment, the present application discloses pharmaceutical compositions comprising a compound of the present invention, or a pharmaceutically acceptable salt thereof, in combination with at least one additional active agent, and a pharmaceutically acceptable carrier or excipient. In yet another embodiment, the present application provides a combination pharmaceutical agent with two or more therapeutic agents in a unitary dosage form. Thus, it is also possible to combine any compound of the invention with one or more other active agents in a unitary dosage form.

The combination therapy may be administered as a simultaneous or sequential regimen. When administered sequentially, the combination may be administered in two or more administrations.

Co-administration of a compound of the invention with one or more other active agents generally refers to simultaneous or sequential administration of a compound of the invention and one or more other active agents, such that therapeutically effective amounts of the compound of the invention and one or more other active agents are both present in the body of the patient.

Co-administration includes administration of unit dosages of the compounds of the invention before or after administration of unit dosages of one or more other active agents, for example, administration of the compounds of the invention within seconds, minutes, or hours of the administration of one or more other active agents. For example, a unit dose of a compound of the invention can be administered first, followed within seconds or minutes by administration of a unit dose of one or more other active agents. Alternatively, a unit dose of one or more other active agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active agents. In other cases, it may be desirable to administer a unit dose of one or more other active agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

Methods of Treatment

As used herein, an "agonist" is a substance that stimulates its binding partner, typically a receptor. Stimulation is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Stimulation may be defined with respect to an increase in a particular effect or function that is induced by interaction of the agonist or partial agonist with a binding partner and can include allosteric effects.

As used herein, an "antagonist" is a substance that inhibits its binding partner, typically a receptor. Inhibition is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Inhibition may be defined with respect to a decrease in a particular effect or function that is induced by interaction of the antagonist with a binding partner, and can include allosteric effects.

As used herein, a "partial agonist" or a "partial antagonist" is a substance that provides a level of stimulation or inhibition, respectively, to its binding partner that is not fully or completely agonistic or antagonistic, respectively. It will be recognized that stimulation, and hence, inhibition is defined intrinsically for any substance or category of substances to be defined as agonists, antagonists, or partial agonists.

As used herein, "intrinsic activity" or "efficacy" relates to some measure of biological effectiveness of the binding partner complex. With regard to receptor pharmacology, the context in which intrinsic activity or efficacy should be defined will depend on the context of the binding partner (e.g., receptor/ligand) complex and the consideration of an activity relevant to a particular biological outcome. For example, in some circumstances, intrinsic activity may vary depending on the particular second messenger system involved. Where such contextually specific evaluations are relevant, and how they might be relevant in the context of the present invention, will be apparent to one of ordinary skill in the art.

As used herein, modulation of a receptor includes agonism, partial agonism, antagonism, partial antagonism, or inverse agonism of a receptor.

As will be appreciated by those skilled in the art, when treating a viral infection such as HCV, HBV, or HIV, such treatment may be characterized in a variety of ways and measured by a variety of endpoints. The scope of the present invention is intended to encompass all such characterizations.

In one embodiment, the method can be used to induce an immune response against multiple epitopes of a viral infection in a human. Induction of an immune response against viral infection can be assessed using any technique that is known by those of skill in the art for determining whether an immune response has occurred. Suitable methods of detecting an immune response for the present invention include, among others, detecting a decrease in viral load or antigen in a subject's serum, detection of IFN-gamma-secreting peptide specific T cells, and detection of elevated levels of one or more liver enzymes, such as alanine transferase (ALT) and aspartate transferase (AST). In one embodiment, the detection of IFN-gamma-secreting peptide specific T cells is accomplished using an ELISPOT assay. Another embodiment includes reducing the viral load associated with HBV infection, including a reduction as measured by PCR testing.

Additionally, the compounds of this invention are useful in the treatment of cancer or tumors (including dysplasias, such as uterine dysplasia). These includes hematological malignancies, oral carcinomas (for example of the lip, tongue or pharynx), digestive organs (for example esophagus, stomach, small intestine, colon, large intestine, or rectum), liver and biliary passages, pancreas, respiratory system such as larynx or lung (small cell and non-small cell), bone, connective tissue, skin (e.g., melanoma), breast, reproductive organs (uterus, cervix, testicles, ovary, or prostate), urinary tract (e.g., bladder or kidney), brain and endocrine glands such as the thyroid. In summary, the compounds of this invention are employed to treat any neoplasm, including not only hematologic malignancies but also solid tumors of all kinds.

Hematological malignancies are broadly defined as proliferative disorders of blood cells and/or their progenitors, in which these cells proliferate in an uncontrolled manner. Anatomically, the hematologic malignancies are divided into two primary groups: lymphomas—malignant masses of lymphoid cells, primarily but not exclusively in lymph nodes, and leukemias—neoplasm derived typically from lymphoid or myeloid cells and primarily affecting the bone marrow and peripheral blood. The lymphomas can be sub-divided into Hodgkin's Disease and Non-Hodgkin's lymphoma (NHL). The later group comprises several distinct entities, which can be distinguished clinically (e.g. aggressive lymphoma, indolent lymphoma), histologically (e.g. follicular lymphoma, mantle cell lymphoma) or based on the origin of the malignant cell (e.g. B lymphocyte, T lymphocyte). Leukemias and related malignancies include acute myelogenous leukemia (AML), chronic myelogenous leukemia (CML), acute lymphoblastic leukemia (ALL) and chronic lymphocytic leukemia (CLL). Other hematological malignancies include the plasma cell dyscrasias including multiple myeloma, and the myelodysplastic syndromes.

SYNTHETIC EXAMPLES

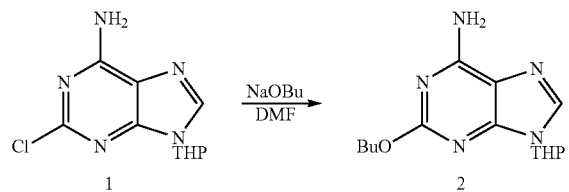

To a solution of the chloropurine 1 (2.54 g, 10.0 mmol) in DMF (20 mL) was added a solution of sodium butoxide (1 M in nBuOH, 20 mL, 20 mmol). The reaction mixture was stirred at 100° C. for 6 h. The reaction mixture was poured onto a saturated solution of NH$_4$Cl (100 mL) and EtOAc (80 mL). The layers were separated, and the aqueous layer was extracted with EtOAc (50 mL). The combined organic layers were washed with brine (75 mL). The organic layer was dried, filtered, and concentrated in vacuo. The crude product was taken onto the next step without further purification.

2: $^1$H-NMR: 300 MHz, (CDCl$_3$) δ: 7.87 (s, 1H), 5.58-5.68 (m, 3H), 4.33 (t, 2H, J=7 Hz), 4.15 (m, 1H), 3.77 (m, 1H), 1.5-2.1 (m, 10H), 0.97 (t, 3H, J=7 Hz).

LCMS-ESI$^+$: calc'd for C$_{14}$H$_{22}$N$_5$O$_2$: 292.4 (M+H$^+$). Found: 292.2 (M+H).

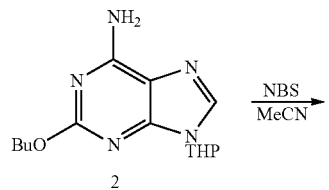

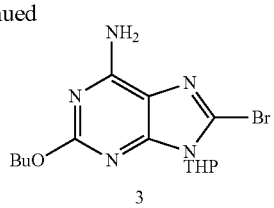

To a solution of the alkoxy purine 2 (~2.9 g, 10.0 mmol) in acetonitrile (25 mL) was added N-bromosuccinimide (2.6 g) portionwise. The reaction was stirred at rt for 2 h and was then poured onto a 20% solution of sodium sulfate (50 mL) and EtOAc (50 mL). The layers were separated. The organic layer was washed with a saturated solution of NaHCO$_3$ (25 mL) then dried, filtered, and concentrated in vacuo. The crude material was purified by flash column chromatography (EtOAc/hexanes).

3: $^1$H-NMR: 300 MHz, (CDCl$_3$) δ: 5.60 (m, 3H), 4.31 (m, 2H), 4.17 (m, 1H), 3.73 (m, 1H), 3.08 (m, 1H), 2.13 (m, 1H), 1.47-1.80 (m, 8H), 0.98 (t, 3H, J=7 Hz).

LCMS-ESI$^+$: calc'd for C$_{14}$H$_{21}$BrN$_5$O$_2$: 371.2 (M+H$^+$). Found: 370.0 [372.0] (M+H)—bromine isotopes.

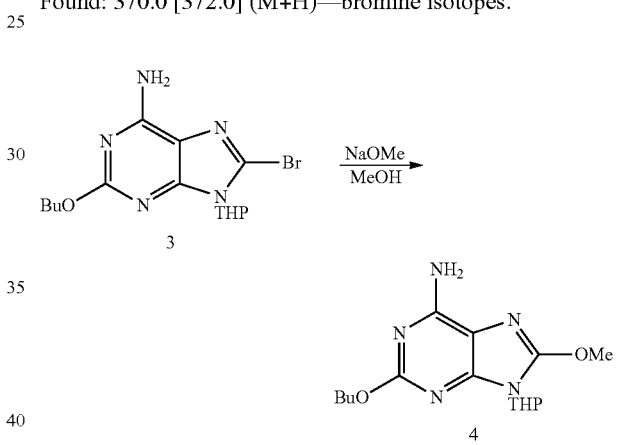

To a solution of the bromide 3 (1.85 g, 5.00 mmol) in MeOH (25 mL) was added a solution of sodium methoxide (1 M in MeOH, 10 mL). The reaction mixture was stirred at 60° C. for 6 h. The mixture was concentrated in vacuo then water was added (20 mL). The mixture was extracted with EtOAc (25 mL). The organic layer was dried, filtered, and concentrated in vacuo. The crude material was purified by flash column chromatography (EtOAc/hexanes).

4: $^1$H-NMR: 300 MHz, (CDCl$_3$) δ: 5.51 (m, 1H), 5.29 (br s, 2H), 4.29 (t, 2H, J=7 Hz), 4.12 (m, 4H), 3.71 (m, 1H), 2.79 (m, 1H), 2.10 (m, 1H), 1.47-1.80 (m, 8H), 0.98 (t, 3H, J=7 Hz).

LCMS-ESI$^+$: calc'd for C$_{15}$H$_{24}$N$_5$O$_3$: 322.4 (M+H$^+$). Found: 322.2 (M+H).

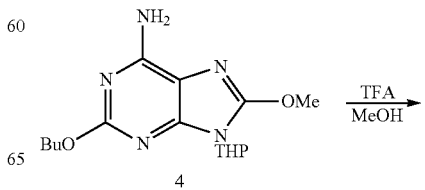

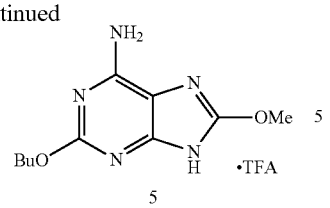

To a solution of the methyl imidate 4 (1.2 g) in MeOH (15 mL) was added trifluoroacetic acid (1.5 mL). The reaction mixture was stirred at rt for 4 days and concentrated in vacuo. The solid was filtered and washed MeOH/EtOAc.

5: $^1$H-NMR: 300 MHz, (CD$_3$OD) δ: 4.48 (t, 2H, J=7 Hz), 4.14 (s, 3H), 1.79 (m, 2H), 1.50 (m, 2H), 0.98 (t, 3H, J=7 Hz).

LCMS-ESI$^+$: calc'd for C$_{10}$H$_{16}$N$_5$O$_2$: 238.3 (M+H$^+$). Found: 238.1 (M+H).

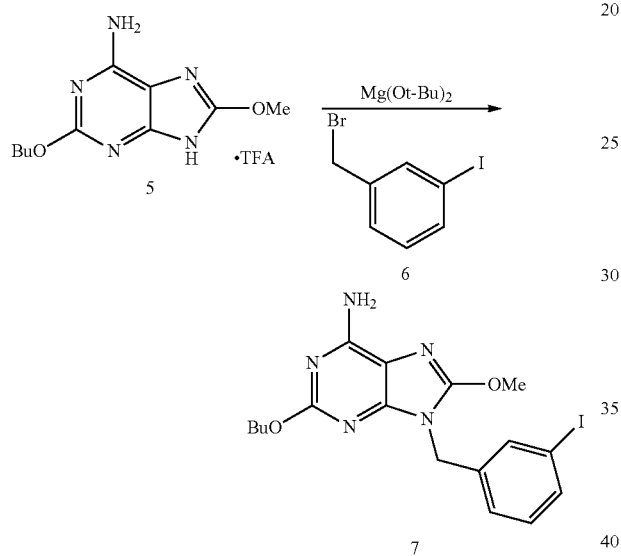

To a solution of the purine salt 5 (1.76 g, 5.00 mmol) in DMF (25 mL) was added Mg(Ot-Bu)$_2$ (2.13 g, 12.5 mmol) and 3-iodobenzyl bromide (6) (1.63 g, 5.50 mmol). The reaction mixture was stirred at 60° C. for 3 h. The reaction mixture was poured onto a saturated solution of NH$_4$Cl (50 mL) and EtOAc (50 mL). The layers were separated and the organic layer was washed with brine (25 mL). The organic solution was dried over Na$_2$SO$_4$, filtered, and concentrated in vacuo. The crude material was purified by flash column chromatography (CH$_2$Cl$_2$ and EtOAc containing 2% MeOH).

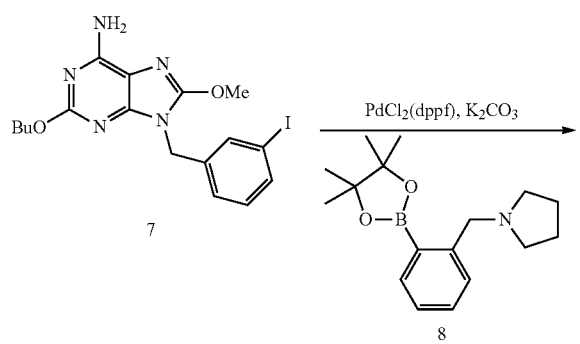

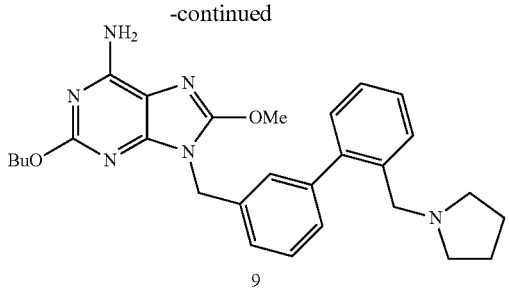

To a solution of the aryl halide 7 (40 mg, 0.098 mmol) and 1-(2-(4,4,5,5-tetramethyl-1,3,2-dioxaborolan-2-yl)benzyl)pyrrolidine (8) (31 mg, 0.11 mmol) in toluene (750 L), ethanol (375 L), and water (375 L) was added potassium carbonate (K$_2$CO$_3$) (41 mg, 0.29 mmol) and [1,1-bis(diphenylphosphino)ferrocene]dichloropalladium(II) (2.1 mg, 0.0029 mmol). The reaction mixture was stirred at 80° C. for 2 h. The reaction mixture was then diluted with water (1 mL) and EtOAc (1 mL). The layers were separated, and the organic layer was concentrated in vacuo. The crude material was purified by flash column chromatography (CH$_2$Cl$_2$/MeOH).

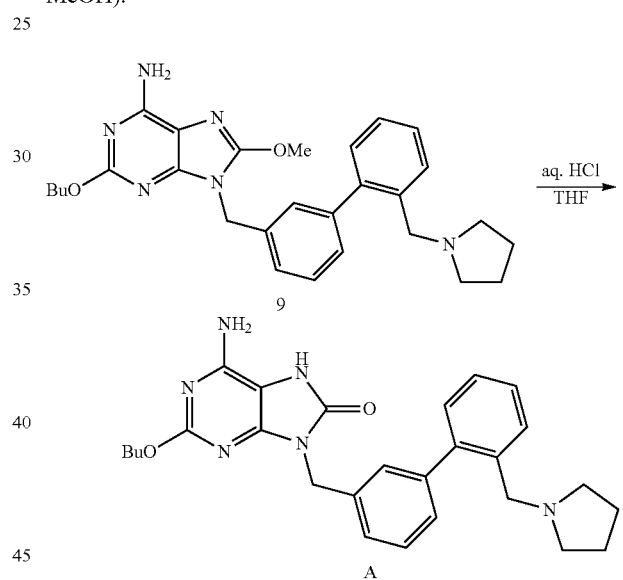

To a solution of the methyl imidate 9 (28 mg, 0.057 mmol) in THF (1 mL) was added a 1 M HCl solution (120 L). The reaction was stirred at 55° C. for 3 h. The THF was removed in vacuo. The remaining oil was diluted with water (~2 mL), frozen, and left on a lyophilizer overnight.

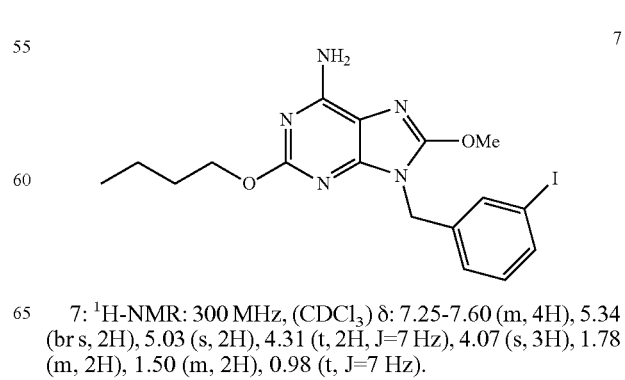

7: $^1$H-NMR: 300 MHz, (CDCl$_3$) δ: 7.25-7.60 (m, 4H), 5.34 (br s, 2H), 5.03 (s, 2H), 4.31 (t, 2H, J=7 Hz), 4.07 (s, 3H), 1.78 (m, 2H), 1.50 (m, 2H), 0.98 (t, J=7 Hz).

LCMS-ESI⁺: calc'd for $C_{17}H_{21}IN_5O_2$: 454.3 (M+H⁺). Found: 454.0 (M+H).

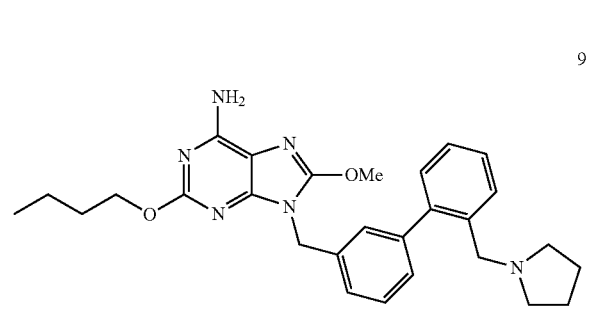 [SMILES: CCCCOc1nc(N)c2nc(OC)n(Cc3cccc(-c4ccccc4CN4CCCC4)c3)c2n1]

9

9: ¹H-NMR: 300 MHz, (CDCl₃) δ: 7.59 (d, 1H, J=7 Hz), 7.26-7.35 (m, 6H), 7.20 (d, 1H, J=7 Hz), 5.30 (br s, 2H), 5.14 (s, 2H), 4.27 (t, 2H, J=7 Hz), 4.09 (s, 3H), 3.51 (s, 2H), 2.39 (br s, 4H), 1.69-1.77 (m, 6H), 1.45 (m, 2H), 0.94 (t, 3H, J=7 Hz).

LCMS-ESI⁺: calc'd for $C_{28}H_{35}N_6O_2$: 487.6 (M+H⁺). Found: 487.1 (M+H).

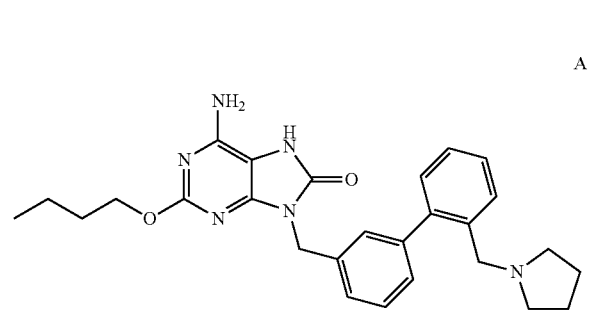 [SMILES: CCCCOc1nc(N)c2[nH]c(=O)n(Cc3cccc(-c4ccccc4CN4CCCC4)c3)c2n1]

A

A: ¹H-NMR: 300 MHz, (CD₃OD) δ: 7.77 (br m, 1H), 7.33-7.55 (m, 7H), 5.14 (s, 2H), 4.55 (m, 2H), 4.43 (s, 2H), 3.38 (m, 2H), 2.85 (m, 2H), 1.90 (m, 4H), 1.81 (m, 2H), 1.49 (m, 2H), 0.98 (t, 3H, J=7 Hz).

LCMS-ESI⁺: calc'd for $C_{27}H_{33}N_6O_2$: 473.6 (M+H⁺). Found: 473.2 (M+H).

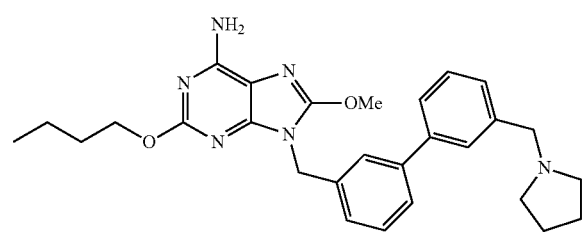

10

Synthesized from compound 7 according to the procedure for compound 9, using 1-(3-(4,4,5,5-tetramethyl-1,3,2-dioxaborolan-2-yl)benzyl)pyrrolidine.

10: ¹H-NMR: 300 MHz, (CDCl₃) δ: 7.27-7.61 (m, 8H), 5.31 (br s, 2H), 5.16 (s, 2H), 4.31 (t, 2H, J=7 Hz), 4.10 (s, 3H), 3.68 (s, 2H), 2.55 (br s, 4H), 1.71-1.81 (m, 6H), 1.44 (m, 2H), 0.95 (t, 3H, J=7 Hz).

LCMS-ESI⁺: calc'd for $C_{28}H_{35}N_6O_2$: 487.6 (M+H⁺). Found: 487.1 (M+H).

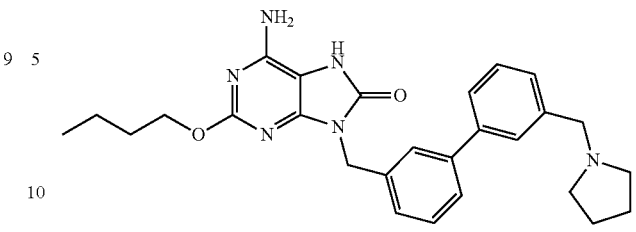

B

Synthesized from compound 10 according to the procedure for compound A.

B: ¹H-NMR: 300 MHz, (CD₃OD) δ: 7.89 (s, 1H), 7.78 (s, 1H), 7.42-7.67 (m, 6H), 5.11 (s, 2H), 4.50 (m, 4H), 3.52 (br m, 2H), 3.22 (br m, 2H), 2.19 (br m, 2H), 2.04 (br m, 2H), 1.76 (m, 2H), 1.45 (m, 2H), 0.94 (t, 3H, J=7 Hz).

LCMS-ESI⁺: calc'd for $C_{27}H_{33}N_6O_2$: 473.6 (M+H⁺). Found: 473.2 (M+H).

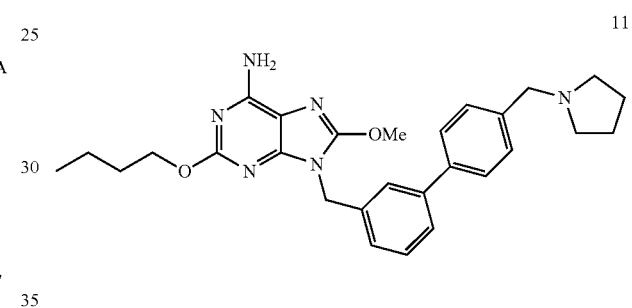

11

Synthesized from compound 7 according to the procedure for compound 9, using 1-(4-(4,4,5,5-tetramethyl-1,3,2-dioxaborolan-2-yl)benzyl)pyrrolidine.

11: ¹H-NMR: 300 MHz, (CDCl₃) δ: 7.60 (s, 1H), 7.27-7.51 (m, 7H), 5.30 (br s, 2H), 5.16 (s, 2H), 4.31 (t, 2H, J=7 Hz), 4.10 (s, 3H), 3.67 (s, 2H), 2.55 (br s, 4H), 1.72-1.81 (m, 6H), 1.48 (m, 2H), 0.95 (t, 3H, J=7 Hz).

LCMS-ESI⁺: calc'd for $C_{28}H_{35}N_6O_2$: 487.6 (M+H⁺). Found: 487.1 (M+H).

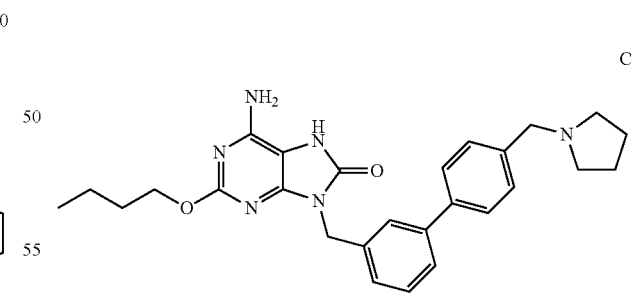

C

Synthesized from compound 11 according to the procedure for compound A.

C: ¹H-NMR: 300 MHz, (CD₃OD) δ: 7.44-7.74 (m, 8H), 5.11 (br s, 2H), 4.52 (br s, 2H), 4.45 (s, 2H), 3.54 (br s, 2H), 3.24 (br s, 2H), 2.21 (br m, 2H), 2.04 (br m, 2H), 1.77 (br m, 2H), 1.45 (br m, 2H), 0.95 (br m, 3H).

LCMS-ESI⁺: calc'd for $C_2H_{33}N_6O_2$: 473.6 (M+H⁺). Found: 473.2 (M+H).

12

Synthesized from compound 5 according to the procedure for compound 7, using 4-iodobenzyl bromide.

12: $^1$H-NMR: 300 MHz, (CDCl$_3$) δ: 7.64 (d, 2H, J=8 Hz), 7.07 (d, 2H, J=8 Hz), 5.34 (br s, 2H), 5.04 (s, 2H), 4.31 (t, 2H, J=7 Hz), 4.09 (s, 3H), 1.78 (m, 2H), 1.50 (m, 2H), 0.97 (t, J=7 Hz).

LCMS-ESI$^+$: calc'd for C$_{17}$H$_{21}$IN$_5$O$_2$: 454.3 (M+H$^+$). Found: 454.0 (M+H).

13

Synthesized from compound 12 according to the procedure for compound 9, using 1-(2-(4,4,5,5-tetramethyl-1,3,2-dioxaborolan-2-yl)benzyl)pyrrolidine.

13: $^1$H-NMR: 300 MHz, (CDCl$_3$) δ: 7.56 (d, 1H, J=8 Hz), 7.19-7.36 (m, 7H), 5.27 (br s, 2H), 5.15 (s, 2H), 4.33 (t, 2H, J=7 Hz), 4.13 (s, 3H), 3.53 (s, 2H), 2.43 (m, 4H), 1.72-1.81 (m, 6H), 1.49 (m, 2H), 0.97 (t, 3H, J=7 Hz).

LCMS-ESI$^+$: calc'd for C$_{28}$H$_{35}$N$_6$O$_2$: 487.6 (M+H$^+$). Found: 487.1 (M+H).

D

Synthesized from compound 13 according to the procedure for compound A.

D: $^1$H-NMR: 300 MHz, (CD$_3$OD) δ: 7.77 (m, 1H), 7.50-7.59 (m, 4H), 7.32-7.7.49 (m, 3H), 5.14 (s, 2H), 4.59 (m, 2H), 4.43 (s, 2H), 3.39 (br m, 2H), 2.85 (br m, 2H), 1.81-1.91 (m, 6H), 1.51 (m, 2H), 1.00 (t, 3H, J=7 Hz).

LCMS-ESI$^+$: calc'd for C$_{27}$H$_{33}$N$_6$O$_2$: 473.6 (M+H$^+$). Found: 473.2 (M+H).

14

Synthesized from compound 12 according to the procedure for compound 9, using 1-(3-(4,4,5,5-tetramethyl-1,3,2-dioxaborolan-2-yl)benzyl)pyrrolidine.

14: $^1$H-NMR: 300 MHz, (CDCl$_3$) δ: 7.26-7.56 (m, 8H), 5.28 (br s, 2H), 5.14 (s, 2H), 4.32 (t, 2H, J=7 Hz), 4.11 (s, 3H), 3.67 (s, 2H), 2.54 (br s, 4H), 1.74-1.83 (m, 6H), 1.51 (m, 2H), 0.97 (t, 3H, J=7 Hz).

LCMS-ESI$^+$: calc'd for C$_{28}$H$_{35}$N$_6$O$_2$: 487.6 (M+H$^+$). Found: 487.1 (M+H).

E

Synthesized from compound 14 according to the procedure for compound A.

E: $^1$H-NMR: 300 MHz, (CD$_3$OD) δ: 7.88 (br s, 1H), 7.70 (br m, 3H), 7.53 (br m, 4H), 5.09 (s, 2H), 4.55 (br m, 2H), 4.46 (s, 2H), 3.53 (br m, 2H), 3.23 (br m, 2H), 2.19 (br m, 2H), 2.04 (br m, 2H), 1.81 (m, 2H), 1.50 (m, 2H), 0.99 (t, 3H, J=7 Hz).

LCMS-ESI$^+$: calc'd for C$_{27}$H$_{33}$N$_6$O$_2$: 473.6 (M+H$^+$). Found: 473.2 (M+H).

15

Synthesized from compound 12 according to the procedure for compound 9, using 1-(4-(4,4,5,5-tetramethyl-1,3,2-dioxaborolan-2-yl)benzyl)pyrrolidine.

15: $^1$H-NMR: 300 MHz, (CDCl$_3$) δ: 7.51 (m, 4H), 7.38 (m, 4H), 5.42 (br s, 2H), 5.13 (s, 2H), 4.32 (t, 2H, J=7 Hz), 4.10 (s, 3H), 3.65 (s, 2H), 2.54 (br s, 4H), 1.78 (m, 6H), 1.50 (m, 2H), 0.97 (t, 3H, J=7 Hz).

LCMS-ESI$^+$: calc'd for C$_{28}$H$_{35}$N$_6$O$_2$: 487.6 (M+H$^+$). Found: 487.1 (M+H).

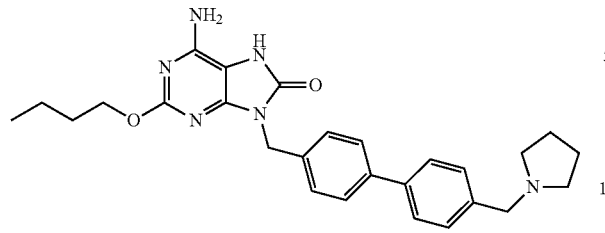

F

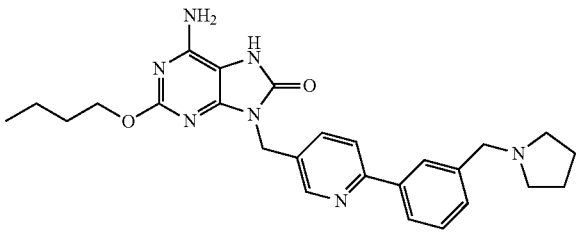

G

Synthesized from compound 15 according to the procedure for compound A.

F: $^1$H-NMR: 300 MHz, (CD$_3$OD) δ: 7.44-7.80 (m, 8H), 5.10 (br s, 2H), 4.55 (br m, 2H), 4.42 (br s, 2H), 3.52 (br m, 2H), 3.23 (br m, 2H), 2.20 (br m, 2H), 2.04 (br m, 2H), 1.81 (br m, 2H), 1.50 (br m, 2H), 0.98 (br m, 3H).

LCMS-ESI$^+$: calc'd for C$_{27}$H$_{33}$N$_6$O$_2$: 473.6 (M+H$^+$). Found: 473.2 (M+H).

Synthesized from compound 17 according to the procedure for compound A.

G: $^1$H-NMR: 300 MHz, (CD$_3$OD) δ: 9.03 (br s, 1H), 8.74 (br s, 1H), 8.53 (br s, 1H), 8.36 (br s, 1H), 8.10 (br s, 1H), 7.92 (br m, 1H), 7.79 (br m, 1H), 5.37 (br s, 2H), 4.59 (br m, 4H), 3.57 (br m, 2H), 3.20 (br m, 2H), 2.22 (br m, 2H), 2.05 (br m, 2H), 1.84 (br m, 2H), 1.53 (br m, 2H), 1.00 (br m, 3H).

LCMS-ESI$^+$: calc'd for C$_{26}$H$_{32}$N$_7$O$_2$: 474.6 (M+H$^+$). Found: 474.2 (M+H).

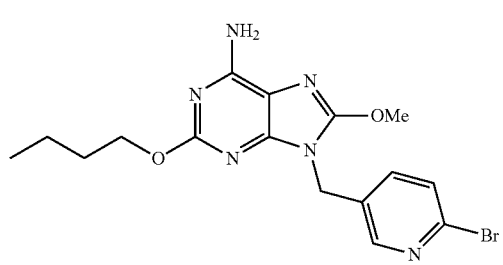

16

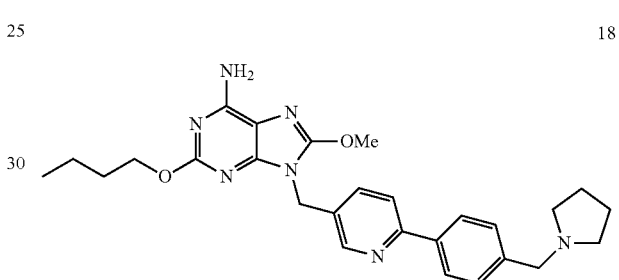

18

Synthesized from compound 5 according to the procedure for compound 7, using 2-bromo-5-(bromomethyl)pyridine.

16: $^1$H-NMR: 300 MHz, (CDCl$_3$) δ: 8.44 (d, 1H, J=2 Hz), 7.58 (dd, 1H, J=8, 2 Hz), 7.43 (d, 1H, J=8 Hz), 5.26 (br s, 2H), 5.07 (s, 2H), 4.30 (t, 2H, J=7 Hz), 4.11 (s, 3H), 1.78 (m, 2H), 1.50 (m, 2H), 0.98 (t, 3H, J=7 Hz).

LCMS-ESI$^+$: calc'd for C$_{16}$H$_{20}$BrN$_6$O$_2$: 408.3 (M+H$^+$). Found: 407.0 [409.0] (M+H)—bromine isotopes.

Synthesized from compound 16 according to the procedure for compound 9, using 1-(4-(4,4,5,5-tetramethyl-1,3,2-dioxaborolan-2-yl)benzyl)pyrrolidine.

18: $^1$H-NMR: 300 MHz, (CDCl$_3$) δ: 8.71 (s, 1H), 7.89 (d, 2H, J=8 Hz), 7.74 (d, 1H, J=8 Hz), 7.65 (d, 1H, J=8 Hz), 7.42 (d, 1H, J=8 Hz), 5.41 (br s, 2H), 5.13 (s, 2H), 4.31 (t, 2H, J=7 Hz), 4.10 (s, 3H), 3.68 (s, 2H), 2.55 (br s, 4H), 1.77 (m, 6H), 1.50 (m, 2H), 0.97 (t, 3H, J=7 Hz).

LCMS-ESI$^+$: calc'd for C$_{27}$H$_{34}$N$_7$O$_2$: 488.6 (M+H$^+$). Found: 488.2 (M+H).

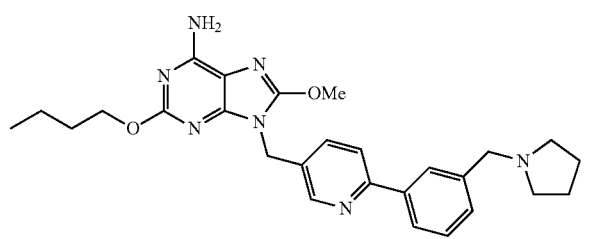

17

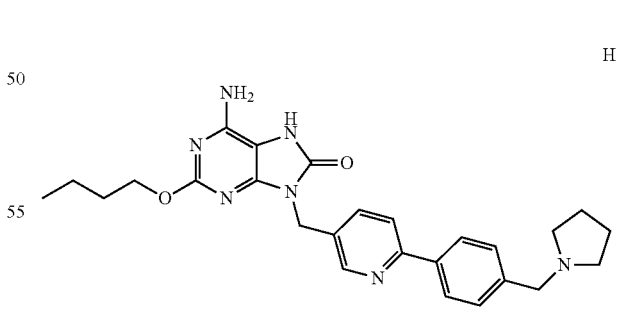

H

Synthesized from compound 16 according to the procedure for compound 9, using 1-(3-(4,4,5,5-tetramethyl-1,3,2-dioxaborolan-2-yl)benzyl)pyrrolidine.

17: $^1$H-NMR: 300 MHz, (CDCl$_3$) δ: 8.72 (s, 1H), 7.65-7.92 (m, 4H), 7.40 (m, 2H), 5.31 (br s, 2H), 5.14 (s, 2H), 4.32 (t, 2H, J=7 Hz), 4.11 (s, 3H), 3.70 (s, 2H), 2.55 (br s, 4H), 1.78 (m, 6H), 1.51 (m, 2H), 0.97 (t, 3H, J=7 Hz).

LCMS-ESI$^+$: calc'd for C$_{27}$H$_{34}$N$_7$O$_2$: 488.6 (M+H$^+$). Found: 488.2 (M+H).

Synthesized from compound 18 according to the procedure for compound A.

H: $^1$H-NMR: 300 MHz, (CD$_3$OD) δ: 8.98 (br s, 1H), 8.61 (br s, 1H), 8.36 (br s, 1H), 8.11 (br s, 2H), 7.88 (br s, 2H), 5.33 (br s, 2H), 4.55 (br m, 4H), 3.56 (br m, 2H), 3.27 (br m, 2H), 2.22 (br m, 2H), 2.05 (br m, 2H), 1.83 (br m, 2H), 1.52 (br m, 2H), 1.00 (br m, 3H).

LCMS-ESI+: calc'd for $C_{26}H_{32}N_7O_2$: 474.6 (M+H+). Found: 474.2 (M+H).

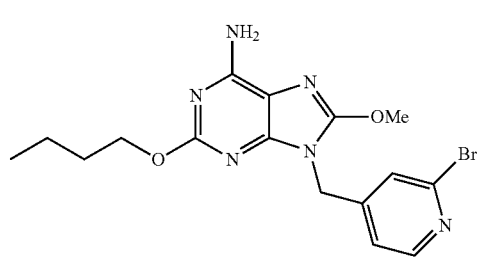

19

Synthesized from compound 5 according to the procedure for compound 7, using 2-bromo-4-(bromomethyl)pyridine.

19: $^1$H-NMR: 300 MHz, (CDCl$_3$) δ: 8.31 (d, 1H, J=5 Hz), 7.38 (s, 1H), 7.13 (d, 1H, J=5 Hz), 5.39 (br s, 2H), 5.07 (s, 2H), 4.29 (t, 2H, J=7 Hz), 4.11 (s, 3H), 1.77 (m, 2H), 1.50 (m, 2H), 0.96 (t, 3H, J=7 Hz).

LCMS-ESI+: calc'd for $C_{16}H_{20}BrN_6O_2$: 408.3 (M+H+). Found: 407.0 [409.0] (M+H)—bromine isotopes.

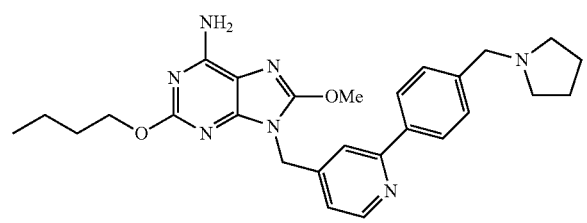

20

Synthesized from compound 19 according to the procedure for compound 9, using 1-(4-(4,4,5,5-tetramethyl-1,3,2-dioxaborolan-2-yl)benzyl)pyrrolidine.

20: $^1$H-NMR: 300 MHz, (CDCl$_3$) δ: 8.60 (d, 1H, J=5 Hz), 7.88 (d, 2H, J=8 Hz), 7.62 (s, 1H), 7.43 (d, 2H, J=8 Hz), 7.09 (d, 1H, J=5 Hz), 5.36 (br s, 2H), 5.15 (s, 2H), 4.28 (t, 2H, J=7 Hz), 4.09 (t, 3H), 3.69 (s, 2H), 2.56 (br s, 4H), 1.74 (m, 6H), 1.49 (m, 2H), 0.94 (t, 3H, J=7 Hz).

LCMS-ESI+: calc'd for $C_{27}H_{34}N_7O_2$: 488.6 (M+H+). Found: 488.2 (M+H).

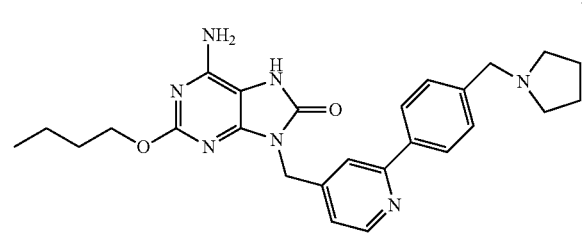

I

Synthesized from compound 20 according to the procedure for compound A.

I: $^1$H-NMR: 300 MHz, (CD$_3$OD) δ: 8.84 (br s, 1H), 8.40 (br s, 1H), 8.09 (br s, 2H), 7.90 (br m, 3H), 5.43 (br s, 2H), 4.56 (br s, 2H), 4.47 (br m, 2H), 3.56 (br m, 2H), 3.27 (br m, 2H), 2.22 (br m, 2H), 2.05 (br m, 2H), 1.76 (br m, 2H), 1.46 (br m, 2H), 0.95 (br m, 3H).

LCMS-ESI+: calc'd for $C_{26}H_{32}N_7O_2$: 474.6 (M+H+). Found: 474.2 (M+H).

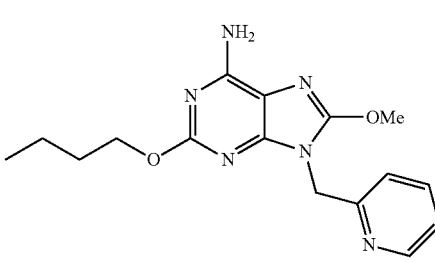

21

Synthesized from compound 5 according to the procedure for compound 7, using 5-bromo-2-(bromomethyl)pyridine.

21: $^1$H-NMR: 300 MHz, (CDCl$_3$) δ: 8.61 (s, 1H), 7.73 (d, 1H, J=8 Hz), 6.99 (d, 1H, J=8 Hz), 5.32 (br s, 2H), 5.21 (s, 2H), 4.25 (t, 2H, J=7 Hz), 4.08 (s, 3H), 1.71 (m, 2H), 1.46 (m, 2H), 0.94 (t, 3H, J=7 Hz).

LCMS-ESI+: calc'd for $C_{16}H_{20}BrN_6O_2$: 408.3 (M+H+). Found: 407.0 [409.0] (M+H)—bromine isotopes.

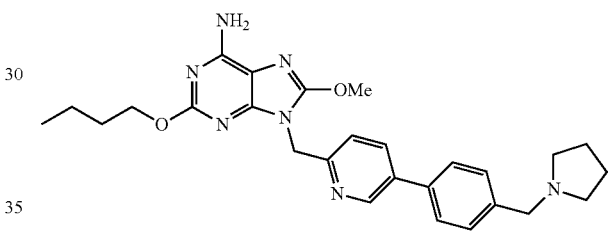

22

Synthesized from compound 21 according to the procedure for compound 9, using 1-(4-(4,4,5,5-tetramethyl-1,3,2-dioxaborolan-2-yl)benzyl)pyrrolidine.

22: $^1$H-NMR: 300 MHz, (CDCl$_3$) δ: 8.77 (s, 1H), 7.79 (d, 1H, J=8 Hz), 7.48 (m, 4H), 7.12 (d, 1H, J=8 Hz), 4.26 (t, 2H, J=7 Hz), 4.10 (s, 3H), 3.74 (s, 2H), 2.63 (m, 4H), 1.84 (m, 4H), 1.74 (m, 2H), 1.46 (m, 2H), 0.94 (t, 3H, J=7 Hz).

LCMS-ESI+: calc'd for $C_{27}H_{34}N_7O_2$: 488.6 (M+H+). Found: 488.2 (M+H).

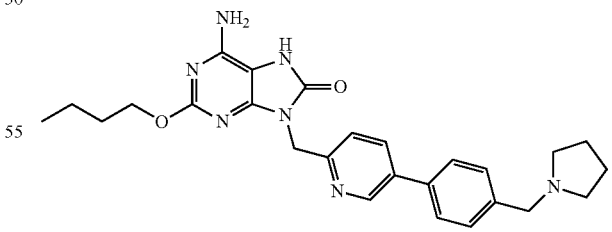

J

Synthesized from compound 22 according to the procedure for compound A.

J: $^1$H-NMR: 300 MHz, (CD$_3$OD) δ: 9.19 (s, 1H), 8.87 (br s, 1H), 8.12 (br s, 1H), 7.95 (d, 2H, J=8 Hz), 7.80 (d, 2H, J=8 Hz), 5.52 (s, 2H), 4.50 (m, 4H), 3.55 (br m, 2H), 3.26 (br m, 2H), 2.21 (br m, 2H), 2.06 (br m, 2H), 1.77 (m, 2H), 1.46 (m, 2H), 0.95 (t, 3H, J=7 Hz).

LCMS-ESI+: calc'd for $C_{26}H_{32}N_7O_2$: 474.6 (M+H+). Found: 474.2 (M+H).

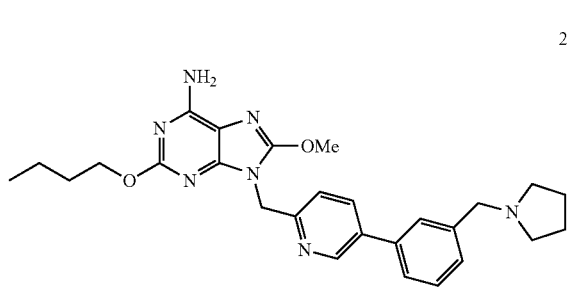

23

Synthesized from compound 21 according to the procedure for compound 9, using 1-(3-(4,4,5,5-tetramethyl-1,3,2-dioxaborolan-2-yl)benzyl)pyrrolidine.

23: $^1$H-NMR: 300 MHz, (CDCl$_3$) δ: 8.78 (s, 1H), 7.80 (d, 1H, J=8 Hz), 7.53 (s, 1H), 7.41 (m, 3H), 7.12 (d, 1H, J=8 Hz), 5.37 (br s, 2H), 5.31 (s, 2H), 4.26 (t, 2H, J=7 Hz), 4.09 (s, 3H), 3.69 (s, 2H), 2.56 (br m, 4H), 1.74 (m, 6H), 1.47 (m, 2H), 0.93 (t, 3H, J=7 Hz).

LCMS-ESI+: calc'd for $C_{27}H_{34}N_7O_2$: 488.6 (M+H+). Found: 488.2 (M+H).

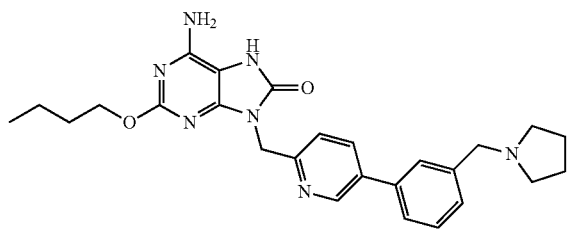

K

Synthesized from compound 23 according to the procedure for compound A.

K: $^1$H-NMR: 300 MHz, (CD$_3$OD) δ: 9.31 (s, 1H), 9.02 (m, 1H), 8.20 (m, 2H), 7.97 (m, 2H), 7.73 (m, 2H), 5.55 (s, 2H), 4.52 (m, 4H), 3.56 (m, 2H), 3.27 (m, 2H), 2.20 (m, 2H), 2.06 (m, 2H), 1.78 (m, 2H), 1.47 (m, 2H), 0.96 (t, 3H, J=7 Hz).

LCMS-ESI+: calc'd for $C_{26}H_{32}N_7O_2$: 474.6 (M+H+). Found: 474.2 (M+H).

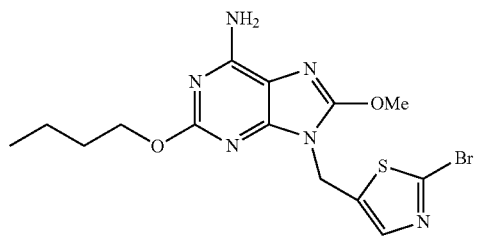

24

Synthesized from compound 5 according to the procedure for compound 7, using 2-bromo-5-(bromomethyl)thiazole.

24: $^1$H-NMR: 300 MHz, (CDCl$_3$) δ: 7.58 (s, 1H), 5.26 (s, 2H), 4.33 (t, 2H, J=7 Hz), 4.14 (s, 3H), 1.80 (m, 2H), 1.53 (m, 2H), 0.99 (t, 3H, J=7 Hz).

LCMS-ESI+: calc'd for $C_{14}H_{18}BrN_6O_2S$: 414.3 (M+H+). Found: 413.0 [415.0] (M+H)—bromine isotopes.

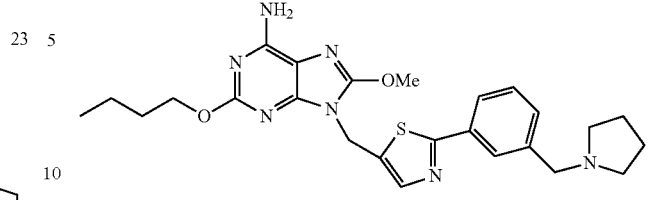

25

Synthesized from compound 24 according to the procedure for compound 9, using 1-(3-(4,4,5,5-tetramethyl-1,3,2-dioxaborolan-2-yl)benzyl)pyrrolidine.

25: $^1$H-NMR: 300 MHz, (CDCl$_3$) δ: 7.74-7.82 (m, 3H), 7.33-7.44 (m, 2H), 5.30 (s, 2H), 5.26 (s, 2H), 4.34 (t, 2H, J=7 Hz), 4.15 (s, 3H), 3.67 (s, 2H), 2.54 (m, 4H), 1.79 (m, 6H), 1.54 (m, 2H), 0.99 (t, 3H, J=7 Hz).

LCMS-ESI+: calc'd for $C_{25}H_{32}N_7O_2S$: 494.6 (M+H+). Found: 494.1 (M+H).

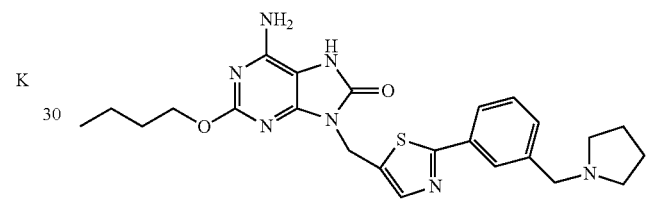

L

Synthesized from compound 25 according to the procedure for compound A.

L: $^1$H-NMR: 300 MHz, (CD$_3$OD) δ: 8.22 (br s, 1H), 8.14 (s, 1H), 8.03 (m, 1H), 7.77 (m, 1H), 7.65 (m, 1H), 5.38 (s, 2H), 4.65 (br m, 2H), 4.51 (s, 2H), 3.54 (br m, 2H), 3.25 (br m, 2H), 2.20 (m, 2H), 2.04 (m, 2H), 1.87 (m, 2H), 1.54 (m, 2H), 1.01 (t, 3H, J=7 Hz).

LCMS-ESI+: calc'd for $C_{24}H_{30}N_7O_2S$: 480.6 (M+H+). Found: 480.1 (M+H).

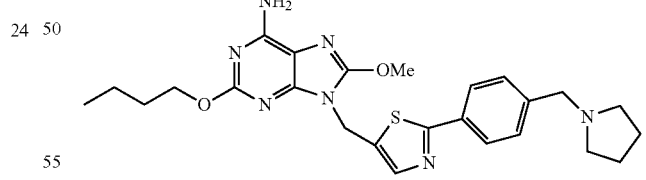

26

Synthesized from compound 24 according to the procedure for compound 9, using 1-(4-(4,4,5,5-tetramethyl-1,3,2-dioxaborolan-2-yl)benzyl)pyrrolidine.

26: $^1$H-NMR: 300 MHz, (CDCl$_3$) δ: 7.80 (m, 3H), 7.38 (m, 2H), 5.42 (br s, 2H), 5.28 (s, 2H), 4.34 (m, 2H), 4.13 (s, 3H), 3.64 (s, 2H), 2.52 (m, 4H), 1.79 (m, 6H), 1.51 (m, 2H), 0.97 (m, 3H).

LCMS-ESI+: calc'd for $C_{25}H_{32}N_7O_2S$: 494.6 (M+H+). Found: 494.1 (M+H).

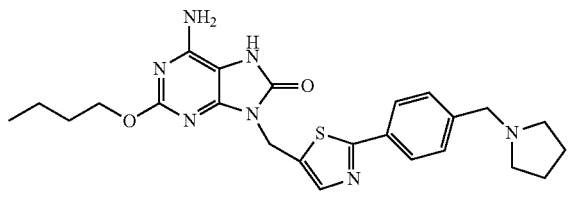

M

Synthesized from compound 26 according to the procedure for compound A.

M: $^1$H-NMR: 300 MHz, (CD$_3$OD) δ: 8.10 (br s, 1H), 8.03 (br m, 2H), 7.75 (br m, 2H), 5.37 (s, 2H), 4.64 (br m, 2H), 4.48 (s, 2H), 3.54 (br m, 2H), 3.23 (br m, 2H), 2.20 (m, 2H), 2.04 (m, 2H), 1.87 (m, 2H), 1.54 (m, 2H), 1.02 (t, 3H, J=7 Hz).

LCMS-ESI$^+$: calc'd for C$_{24}$H$_{30}$N$_7$O$_2$S: 480.6 (M+H$^+$). Found: 480.2 (M+H).

27

Synthesized from compound 5 according to the procedure for compound 7, using 2-(4-(bromomethyl)phenyl)-4,4,5,5-tetramethyl-1,3,2-dioxaborolane.

27: $^1$H-NMR: 300 MHz, (CDCl$_3$): δ: 7.74 (d, 2H, J=8 Hz), 7.30 (d, 2H, J=8 Hz), 5.28 (br s, 2H), 5.11 (s, 2H), 4.30 (t, 2H, J=7 Hz), 4.08 (s, 3H), 1.77 (m, 2H), 1.51 (m, 2H), 1.33 (s, 12H), 1.00 (t, 3H, J=7 Hz).

LCMS-ESI$^+$: calc'd for C$_{23}$H$_{33}$BN$_5$O$_4$: 454.3 (M+H$^+$). Found: 454.1 (M+H).

28

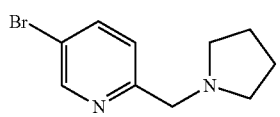

To a solution of 5-bromopicolinaldehyde (558 mg, 3.00 mmol) in MeOH (8 mL) was added acetic acid (400 μL), pyrrolidine (273 μL, 3.30 mmol), and sodium triacetoxyborohydride (634 mg, 3.00 mmol). After 1.5 h, the reaction mixture was poured onto a saturated solution of NH$_4$Cl (15 mL) and EtOAc (15 mL). The layers were separated, and the aqueous layer was extracted with EtOAc (15 mL). The combined organic layers were washed with brine (20 mL), dried, filtered, and concentrated in vacuo to give 510 mg of 28.

28: $^1$H-NMR: 300 MHz, (CDCl$_3$): δ: 8.61 (s, 1H), 7.77 (d, 1H, J=8 Hz), 7.32 (d, 1H, J=8 Hz), 3.74 (s, 2H), 2.57 (m, 4H), 1.81 (m, 4H).

LCMS-ESI$^+$: calc'd for C$_{10}$H$_{14}$BrN$_2$: 242.1 (M+H$^+$). Found: 241.1 [243.1] (M+H)-bromine isotopes.

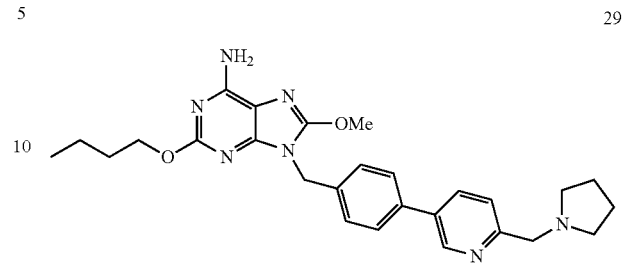

29

Synthesized from compound 27 according to the procedure for compound 9, using 28.

29: $^1$H-NMR: 300 MHz, (CDCl$_3$): δ: 8.75 (s, 1H), 7.81 (d, 1H, J=8 Hz), 7.42-7.53 (m, 5H), 5.20 (br s, 2H), 5.15 (s, 2H), 4.32 (t, 2H, J=7 Hz), 4.11 (s, 3H), 3.87 (s, 2H), 2.68 (m, 4H), 1.75-1.85 (m, 6H), 1.51 (m, 2H), 0.97 (t, 3H, J=7 Hz).

LCMS-ESI$^+$: calc'd for C$_{27}$H$_{34}$N$_7$O$_2$: 488.6 (M+H$^+$). Found: 488.1 (M+H).

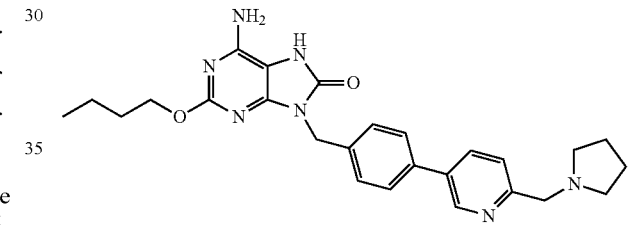

N

Synthesized from compound 29 according to the procedure for compound A.

N: $^1$H-NMR: 300 MHz, (CD$_3$OD) δ: 9.14 (s, 1H), 8.59 (d, 1H, J=8 Hz), 8.08 (d, 1H, J=8 Hz), 7.81 (d, 2H, J=8 Hz), 7.62 (d, 2H, J=8 Hz), 5.15 (s, 2H), 4.81 (s, 2H), 4.56 (t, 2H, J=7 Hz), 3.73 (br m, 2H), 3.22 (br m, 2H), 2.18 (br m, 4H), 1.82 (m, 2H), 1.50 (m, 2H), 0.98 (t, 3H, J=7 Hz).

LCMS-ESI$^+$: calc'd for C$_{26}$H$_{32}$N$_7$O$_2$: 474.6 (M+H$^+$). Found: 474.2 (M+H).

30

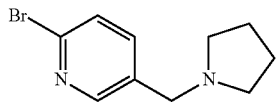

Synthesized from 6-bromonicotinaldehyde according to the procedure for compound 28.

30: $^1$H-NMR: 300 MHz, (CDCl$_3$): δ: 8.30 (s, 1H), 7.58 (d, 1H, J=8 Hz), 7.44 (d, 1H, J=8 Hz), 3.59 (s, 2H), 2.51 (m, 4H), 1.80 (m, 4H).

LCMS-ESI$^+$: calc'd for C$_{10}$H$_{14}$BrN$_2$: 242.1 (M+H$^+$). Found: 241.1 [243.1] (M+H)-bromine isotopes.

31

Synthesized from compound 27 according to the procedure for compound 9, using 30.

31: $^1$H-NMR: 300 MHz, (CDCl$_3$): δ: 8.60 (s, 1H), 7.92 (d, 2H, J=8 Hz), 7.81 (br d, 1H J=8 Hz), 7.66 (d, 1H, J=8 Hz), 7.42 (d, 2H, J=8 Hz), 5.15 (br s, 4H), 4.32 (t, 2H, J=7 Hz), 4.09 (s, 3H), 3.71 (s, 2H), 2.61 (m, 4H), 1.73-1.84 (m, 6H), 1.50 (m, 2H), 0.97 (t, 3H, J=7 Hz).

LCMS-ESI$^+$: calc'd for C$_{27}$H$_{34}$N$_7$O$_2$: 488.6 (M+H$^+$). Found: 488.2 (M+H).

33

Synthesized from compound 27 according to the procedure for compound 9, using 32.

33: $^1$H-NMR: 300 MHz, (CDCl$_3$) δ: 7.88 (d, 2H, J=8 Hz), 7.37 (d, 2H, J=8 Hz), 7.16 (d, 1H), 5.25 (br s, 2H), 5.12 (s, 2H), 4.30 (t, 2H, J=7 Hz), 4.08 (s, 3H), 3.86 (s, 2H), 2.67 (m, 4H), 1.75-1.82 (m, 6H), 1.50 (m, 2H), 0.97 (t, 3H, J=7 Hz).

LCMS-ESI$^+$: calc'd for C$_{25}$H$_{32}$N$_7$O$_2$S: 494.6 (M+H$^+$). Found: 494.1 (M+H).

O

Synthesized from compound 31 according to the procedure for compound A.

O: $^1$H-NMR: 300 MHz, (CD$_3$OD) δ: 9.20 (s, 1H), 8.94 (d, 1H, J=8 Hz), 8.50 (d, 1H, J=8 Hz), 8.04 (d, 2H, J=8 Hz), 7.74 (d, 2H, J=8 Hz), 5.21 (s, 2H), 4.81 (s, 2H), 4.55 (t, 2H, J=7 Hz), 3.68 (br m, 2H), 3.31 (br m, 2H), 2.25 (m, 2H), 2.10 (m, 2H), 1.82 (m, 2H), 1.49 (m, 2H), 0.99 (t, 3H, J=7 Hz).

LCMS-ESI$^+$: calc'd for C$_{26}$H$_{32}$N$_7$O$_2$: 474.6 (M+H$^+$). Found: 474.1 (M+H).

P

Synthesized from compound 33 according to the procedure for compound A.

P: $^1$H-NMR: 300 MHz, (CD$_3$OD) δ: 8.01 (d, 2H, J=8 Hz), 7.82 (s, 1H), 7.54 (d, 2H, J=8 Hz), 5.11 (s, 2H), 4.54 (m, 4H), 3.64 (m, 2H), 3.33 (s, 2H), 2.19 (m, 2H), 2.06 (m, 2H), 1.80 (m, 2H), 1.49 (m, 2H), 0.97 (t, 3H, J=7 Hz).

LCMS-ESI$^+$: calc'd for C$_{24}$H$_{30}$N$_7$O$_2$S: 480.6 (M+H$^+$). Found: 480.1 (M+H).

32

Synthesized from 2-bromothiazole-4-carbaldehyde according to the procedure for compound 28.

32: $^1$H-NMR: 300 MHz, (CDCl$_3$): δ: 7.11 (s, 1H), 3.76 (s, 2H), 2.60 (m, 4H), 1.80 (m, 4H).

LCMS-ESI$^+$: calc'd for C$_8$H$_{12}$BrN$_2$S: 248.2 (M+H$^+$). Found: 247.0 [249.0] (M+H)-bromine isotopes.

34

Synthesized from 2-bromothiazole-5-carbaldehyde according to the procedure for compound 28.

34: $^1$H-NMR: 300 MHz, (CDCl$_3$): δ: 7.38 (s, 1H), 3.79 (s, 2H), 2.56 (m, 4H), 1.80 (m, 4H).

LCMS-ESI$^+$: calc'd for C$_8$H$_{12}$BrN$_2$S: 248.2 (M+H$^+$). Found: 247.0 [249.0] (M+H)-bromine isotopes.

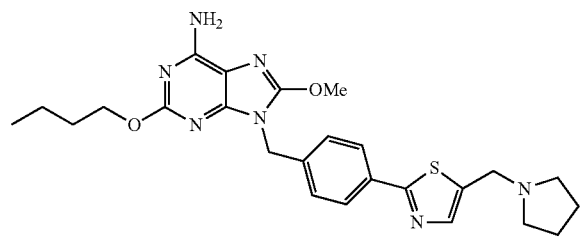

35

Synthesized from compound 27 according to the procedure for compound 9, using 34.

35: $^1$H-NMR: 300 MHz, (CDCl$_3$) δ: 7.85 (d, 2H, J=8 Hz), 7.63 (s, 1H), 7.37 (d, 2H, J=8 Hz), 5.20 (br s, 2H), 5.12 (s, 2H), 4.30 (t, 2H, J=7 Hz), 4.09 (s, 3H), 3.86 (s, 2H), 2.60 (m, 4H), 1.75-1.81 (m, 6H), 1.50 (m, 2H), 0.96 (t, 3H, J=7 Hz).

LCMS-ESI$^+$: calc'd for C$_{25}$H$_{32}$N$_7$O$_2$S: 494.6 (M+H$^+$). Found: 494.1 (M+H).

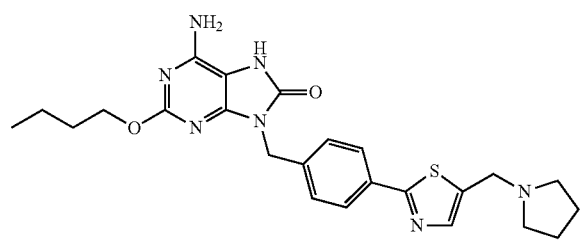

Q

Synthesized from compound 35 according to the procedure for compound A.

Q: $^1$H-NMR: 300 MHz, (CD$_3$OD) δ: 8.15 (br s, 1H), 7.98 (br m, 2H), 7.58 (br m, 2H), 5.12 (br s, 2H), 4.80 (br s, 2H), 4.54 (br m, 2H), 3.64 (m, 2H), 3.29 (m, 2H), 2.22 (m, 2H), 2.07 (m, 2H), 1.80 (m, 2H), 1.48 (m, 2H), 0.98 (br t, 3H, J=7 Hz).

LCMS-ESI$^+$: calc'd for C$_{24}$H$_{30}$N$_7$O$_2$S: 480.6 (M+H$^+$). Found: 480.2 (M+H).

36

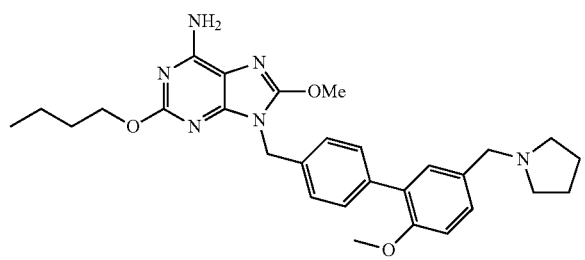

Synthesized from compound 27 according to the procedure for compound 9, using 1-(3-bromo-4-methoxybenzyl)pyrrolidine.

36: $^1$H-NMR: 300 MHz, (CDCl$_3$) δ: 7.47 (d, 1H, J=8 Hz), 7.37 (d, 1H, J=8 Hz), 7.26 (m, 3H), 6.85 (d, 2H, J=8 Hz), 5.29 (br s, 2H), 5.13 (s, 2H), 4.32 (t, 2H, J=7 Hz), 4.10 (s, 3H), 3.79 (s, 5H), 3.59 (s, 3H), 2.53 (m, 4H), 1.79 (m, 6H), 1.51 (m, 2H), 0.97 (t, 3H, J=7 Hz).

LCMS-ESI$^+$: calc'd for C$_{29}$H$_{37}$N$_6$O$_3$: 517.6 (M+H$^+$). Found: 517.2 (M+H).

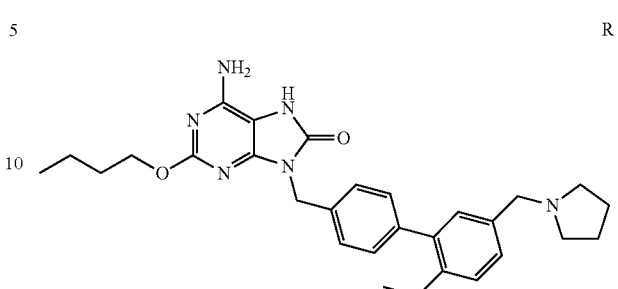

R

Synthesized from compound 36 according to the procedure for compound A.

R: $^1$H-NMR: 300 MHz, (CD$_3$OD) δ: 7.49 (m, 5H), 7.00 (d, 2H, J=8 Hz), 5.09 (s, 2H), 4.57 (m, 2H), 4.37 (s, 2H), 4.13 (s, 3H), 3.47 (m, 2H), 3.19 (m, 2H), 2.17 (m, 2H), 2.02 (m, 2H), 1.83 (m, 2H), 1.50 (m, 2H), 0.97 (t, 3H, J=7 Hz).

LCMS-ESI$^+$: calc'd for C$_{28}$H$_{35}$N$_6$O$_3$: 503.6 (M+H$^+$). Found: 503.1 (M+H).

37

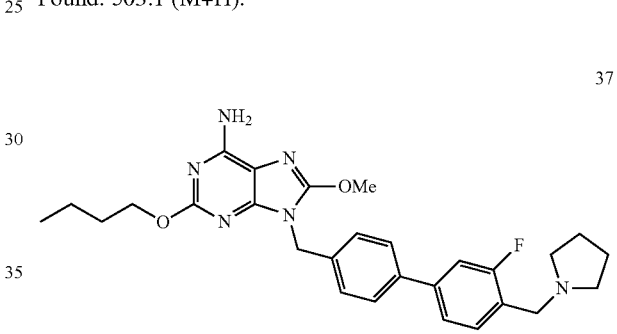

Synthesized from compound 27 according to the procedure for compound 9, using 1-(4-bromo-2-fluorobenzyl)pyrrolidine.

37: $^1$H-NMR: 300 MHz, (CDCl$_3$) δ: 7.20-7.51 (m, 7H), 5.30 (s, 2H), 5.14 (s, 2H), 4.31 (t, 2H, J=7 Hz) 4.10 (s, 3H), 3.72 (s, 2H), 2.59 (m, 4H), 1.78 (m, 6H), 1.50 (m, 2H), 0.97 (t, 2H, J=7 Hz).

LCMS-ESI$^+$: calc'd for C$_{28}$H$_{34}$FN$_6$O$_2$: 505.6 (M+H$^+$). Found: 505.1 (M+H).

S

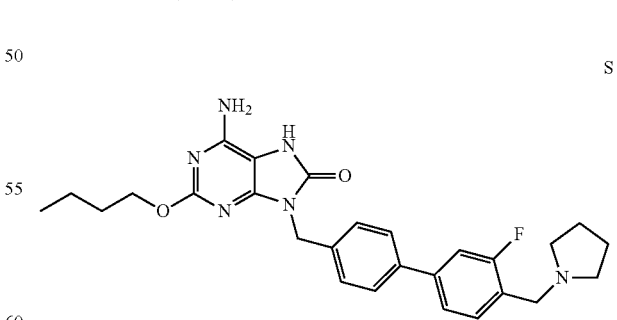

Synthesized from compound 37 according to the procedure for compound A.

S: $^1$H-NMR: 300 MHz, (CD$_3$OD) δ: 7.46-7.73 (m, 7H), 5.10 (br s, 2H), 4.52 (br m, 4H), 3.59 (br m, 2H), 3.28 (br m, 2H), 2.21 (br m, 2H), 2.08 (br m, 2H), 1.80 (br m, 2H), 1.50 (br m, 2H), 0.98 (br m, 3H).

LCMS-ESI⁺: calc'd for $C_{27}H_{32}FN_6O_2$: 491.6 (M+H⁺). Found: 491.2 (M+H).

38

Synthesized from compound 1 according to the procedure for compound 2.

38 ¹H-NMR: 300 MHz, (CDCl₃) δ: 7.88 (s, 1H), 5.62-5.65 (m, 2H), 4.51 (t, J=4.9 Hz, 2H), 4.14-4.17 (m, 1H), 3.77 (t, J=4.6 Hz, 2H), 3.44 (s, 3H), 1.66-2.11 (m, 6H).

LCMS-ESI⁺: calc'd for $C_{13}H_{19}N_5O_3$: 294.3 (M+H⁺). Found: 294.0 (M+H).

39

Synthesized from compound 38 according to the procedure for compound 3. 39: ¹H-NMR: 300 MHz, (CDCl₃) δ: 5.78 (br m, 2H), 4.49 (t, J=4.9 Hz, 2H), 4.14-4.18 (m, 1H), 3.77 (t, J=4.6 Hz, 2H), 3.44 (s, 3H), 1.60-1.83 (m, 6H).

LCMS-ESI⁺: calc'd for $C_{13}H_{18}BrN_5O_3$: 372.1 (M+H⁺). Found: 371.8 (M+H).

40

Synthesized from compound 39 according to the procedure for compound 4.

40: ¹H-NMR: 300 MHz, (CDCl₃) δ: 5.44-5.52 (m, 2H), 4.47 (br m, 2H), 4.10-4.15 (m, 4H), 3.66-3.77 (m, 2H), 3.45 (s, 3H), 1.56-1.76 (m, 6H).

LCMS-ESI⁺: calc'd for $C_{14}H_{21}N_5O_4$: 324.1 (M+H⁺). Found: 323.9 (M+H).

41

Synthesized from compound 40 according to the procedure for compound 5.

41: ¹H-NMR: 300 MHz, (CDCl₃) δ: 4.66 (br m, 2H), 4.21 (s, 3H), 3.79 (br m, 2H), 3.44 (s, 3H).

LCMS-ESI⁺: calc'd for $C_9H_{13}N_5O_3$: 240.1 (M+H⁺). Found: 240.0 (M+H).

42

Synthesized from compound 1 according to the procedure for compound 2.

LCMS-ESI⁺: calc'd for $C_{16}H_{24}N_5O_3$: 334.4 (M+H⁺). Found: 334.1 (M+H).

43

Synthesized from compound 42 according to the procedure for compound 3.

LCMS-ESI⁺: calc'd for $C_{16}H_{23}BrN_5O_3$: 413.3 (M+H⁺). Found: 412.1 (M+H).

44

Synthesized from compound 43 according to the procedure for compound 4.

LCMS-ESI⁺: calc'd for $C_{17}H_{26}N_5O_4$: 364.4 (M+H⁺). Found: 346.2 (M+H).

45

Synthesized from compound 44 according to the procedure for compound 5.

45: ¹H-NMR: 300 MHz, (CD₃OD) δ: 4.33 (d, 2H, J=6 Hz), 4.16 (s, 3H), 3.98 (m, 2H), 3.46 (t, 2H, J=12 Hz), 2.11 (m, 1H), 1.73 (m, 2H), 1.47 (m, 2H).

LCMS-ESI+: calc'd for $C_{12}H_{18}N_5O_3$: 280.3 (M+H+). Found: 280.1 (M+H).

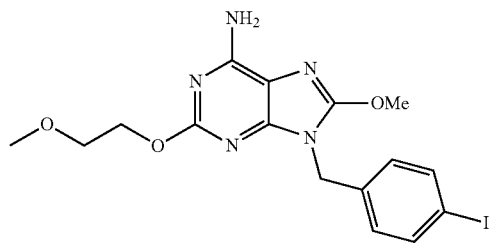

46

Synthesized from compound 40 according to the procedure for compound 7, using 4-iodobenzyl bromide.

46: 1H-NMR: 300 MHz, (CDCl3) δ:7.03-7.62 (m, 2H), 7.24-7.06 (m, 2H), 5.03 (s, 2H), 4.46 (t, J=4.9 Hz, 2H), 4.09 (s, 3H), 3.75 (t, J=4.9 Hz, 2H), 3.43 (s, 3H).

LCMS-ESI+: calc'd for $C_{16}H_{18}N_5O_3$: 456.0 (M+H+). Found: 456.0 (M+H).

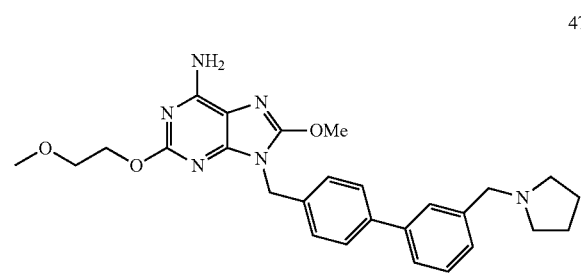

47

Synthesized from compound 46 according to the procedure for compound 9, using 1-(3-(4,4,5,5-tetramethyl-1,3,2-dioxaborolan-2-yl)benzyl)pyrrolidine.

47: 1H-NMR: 300 MHz, (CD3OD) δ: 7.77-7.43 (m, 8H), 5.23 (s, 2H), 4.59 (t, J=4.6 Hz, 2H), 4.44 (s, 2H), 4.18 (s, 3H), 3.76 (t, J=4.6 Hz, 2H), 3.52 (br m, 2H), 3.40 (s, 3H), 3.24 (br m, 2H), 2.20 (br m, 2H), 2.02 (br m, 2H).

LCMS-ESI+: calc'd for $C_{27}H_{32}N_6O_3$: 489.6 (M+H+). Found: 489.2 (M+H).

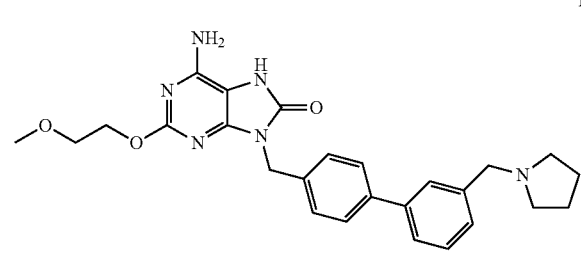

T

Synthesized from compound 47 according to the procedure for compound A.

T 1H-NMR: 300 MHz, (CD3OD) δ: 7.71-7.54 (m, 8H), 5.09 (s, 2H), 4.67 (br m, 2H), 4.46 (s, 2H), 3.77 (br m, 2H), 3.53 (br m, 2H), 3.40 (s, 3H), 3.24 (br m, 2H), 2.19 (br m, 2H), 2.04 (br m, 2H).

LCMS-ESI+: calc'd for $C_{26}H_{30}N_6O_3$: 475.6 (M+H+). Found: 475.2 (M+H).

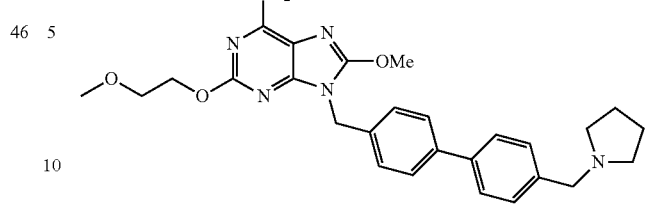

48

Synthesized from compound 46 according to the procedure for compound 9, using 1-(4-(4,4,5,5-tetramethyl-1,3,2-dioxaborolan-2-yl)benzyl)pyrrolidine.

48: 1H-NMR: 300 MHz, (CD3OD) δ: 7.75-7.43 (m, 8H), 5.23 (s, 2H), 4.59 (br m, 2H), 4.42 (s, 2H), 4.18 (s, 3H), 3.76 (br m, 2H), 3.52 (br m, 2H), 3.32 (s, 3H), 3.24 (br m, 2H), 2.20 (br m, 2H), 2.02 (br m, 2H).

LCMS-ESI+: calc'd for $C_{27}H_{32}N_6O_3$: 489.6 (M+H+). Found: 489.2 (M+H).

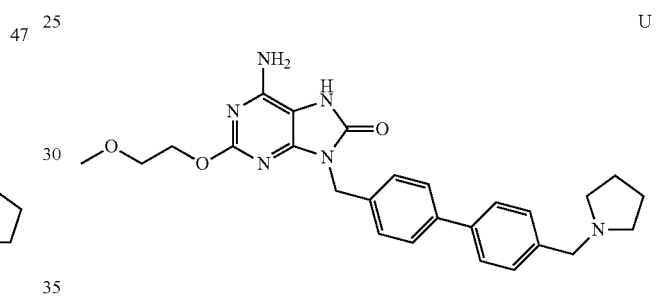

U

Synthesized from compound 48 according to the procedure for compound A.

U: 1H-NMR: 300 MHz, (CD3OD) δ: 7.73-7.51 (m, 8H), 5.10 (s, 2H), 4.64 (t, J=4.2 Hz, 2H), 4.43 (s, 2H), 3.76 (t, J=4.2 Hz, 2H), 3.53 (br m, 2H), 3.38 (s, 3H), 3.24 (br m, 2H), 2.20 (br m, 2H), 2.04 (br m, 2H).

LCMS-ESI+: calc'd for $C_{26}H_{30}N_6O_3$: 475.6 (M+H+). Found: 475.1 (M+H).

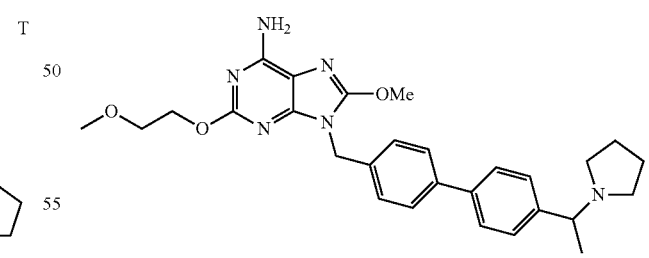

49

Synthesized from compound 46 according to the procedure for compound 9, using 1-(1-(4-(4,4,5,5-tetramethyl-1,3,2-dioxaborolan-2-yl)phenyl)ethyl)pyrrolidine.

49: 1H-NMR: 300 MHz, (CD3OD) δ: 7.73-7.43 (m, 8H), 5.23 (s, 2H), 4.59 (br m, 2H), 4.41 (br m, 1H), 4.18 (br m, 3H), 3.76 (br m, 4H), 3.40 (s, 3H), 3.09 (br m, 2H), 2.07 (br m, 4H), 1.75 (br m, 3H).

LCMS-ESI+: calc'd for $C_{28}H_{34}N_6O_3$: 503.6 (M+H+). Found: 503.0 (M+H+).

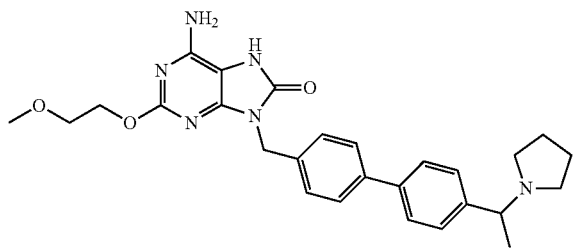

V

Synthesized from compound 49 according to the procedure for compound A.

V: $^1$H-NMR: 300 MHz, (CD$_3$OD) δ: 7.74-7.46 (m, 8H), 5.10 (s, 2H), 4.64 (t, J=4.2 Hz, 2H), 4.42-4.45 (m, 1H), 3.82-3.74 (m, 4H), 3.38 (s, 3H), 3.02-3.11 (m, 2H), 2.06-2.20 (m, 4H), 1.77 (d, J=6.9 Hz, 3H).

LCMS-ESI$^+$: calc'd for C$_{27}$H$_{32}$N$_6$O$_3$: 489.6 (M+H$^+$). Found: 489.0 (M+H$^+$).

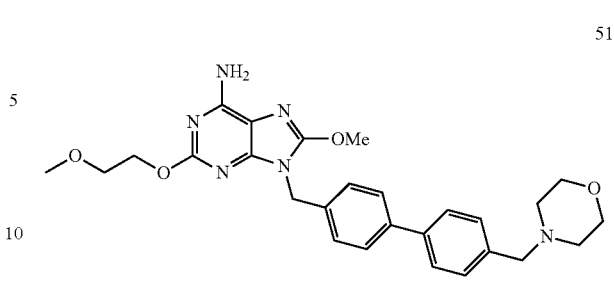

51

Synthesized from compound 46 according to the procedure for compound 9, using 4-(4-(4,4,5,5-tetramethyl-1,3,2-dioxaborolan-2-yl)benzyl)morpholine.

51: $^1$H-NMR: 300 MHz, (CD$_3$OD) δ: 7.76-7.44 (m, 8H), 5.23 (s, 2H), 4.62 (br m, 2H), 4.41 (s, 2H), 4.19 (s, 3H), 4.03 (br m, 2H), 3.77 (br m, 4H), 3.31-3.41 (m, 7H).

LCMS-ESI$^+$: calc'd for C$_{27}$H$_{32}$N$_6$O$_4$: 505.6 (M+H$^+$). Found: 505.2 (M+H$^+$).

50

Synthesized from compound 46 according to the procedure for compound 9, using 1-(3-(4,4,5,5-tetramethyl-1,3,2-dioxaborolan-2-yl)benzyl)piperidine.

50: $^1$H-NMR: 300 MHz, (CD$_3$OD) δ: 7.76-7.46 (m, 8H), 5.23 (s, 2H), 4.60 (br s, 2H), 4.35 (br s, 2H), 4.19 (br s, 3H), 3.77 (br m, 2H), 3.47 (br m, 2H), 3.40 (s, 3H), 2.98 (br m, 2H), 1.72-1.92 (m, 6H).

LCMS-ESI$^+$: calc'd for C$_{28}$H$_{34}$N$_6$O$_3$: 503.6 (M+H$^+$). Found: 503.2 (M+H$^+$).

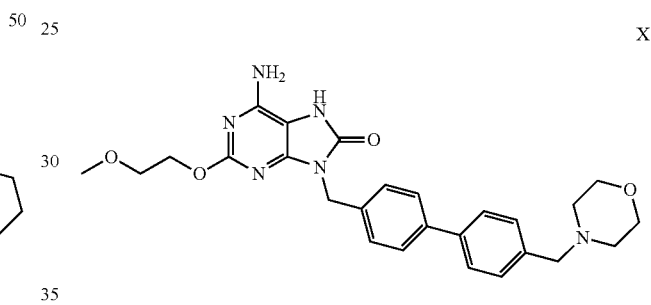

X

Synthesized from compound 51 according to the procedure for compound A.

X: $^1$H-NMR: 300 MHz, (CD$_3$OD) δ: 7.76-7.51 (m, 8H), 5.10 (s, 2H), 4.64 (br m, 2H), 4.42 (s, 2H), 4.08-4.03 (m, 2H), 3.84-3.76 (m, 4H), 3.38 (s, 3H), 3.30-3.21 (m, 4H). LCMS-ESI$^+$: calc'd for C$_{26}$H$_{30}$N$_6$O$_4$: 491.6 (M+H$^+$). Found: 491.1 (M+H$^+$).

W

Synthesized from compound 50 according to the procedure for compound A.

W: $^1$H-NMR: 300 MHz, (CD$_3$OD) δ: 7.85-7.50 (m, 8H), 5.10 (s, 2H), 4.66 (br m, 2H), 4.37 (s, 2H), 3.76 (br m, 2H), 3.46-3.50 (m, 2H), 3.38 (s, 3H), 2.98-3.02 (m, 2H), 1.79-1.97 (m, 6H).

LCMS-ESI$^+$: calc'd for C$_{27}$H$_{32}$N$_6$O$_3$: 489.6 (M+H$^+$). Found: 489.2 (M+H$^+$).

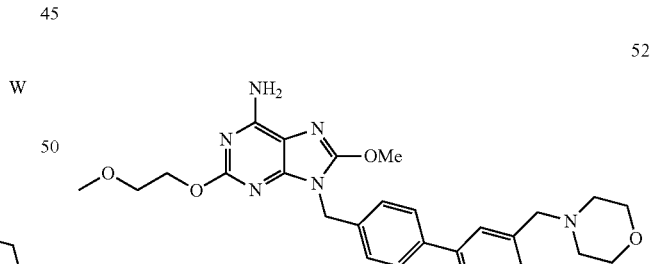

52

Synthesized from compound 46 according to the procedure for compound 9, using 4-(3-(4,4,5,5-tetramethyl-1,3,2-dioxaborolan-2-yl)benzyl)morpholine.

52: $^1$H-NMR: 300 MHz, (CD$_3$OD) δ: 7.78-7.44 (m, 8H), 5.23 (s, 2H), 4.61 (t, J=4.4 Hz, 2H), 4.43 (s, 2H), 4.19 (s, 3H), 4.03 (br m, 2H), 3.78-3.75 (m, 4H), 3.40 (s, 3H), 3.30-3.21 (br m, 4H).

LCMS-ESI$^+$: calc'd for C$_{27}$H$_{32}$N$_6$O$_4$: 505.6 (M+H$^+$). Found: 505.2 (M+H$^+$).

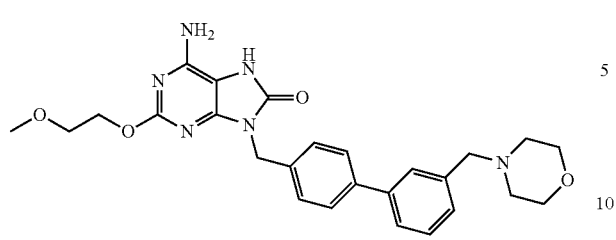

Y

Synthesized from compound 52 according to the procedure for compound A.

Y: $^1$H-NMR: 300 MHz, (CD$_3$OD) δ: 7.87-7.52 (m, 8H), 5.10 (s, 2H), 4.65 (t, J=4.5 Hz, 2H), 4.45 (s, 2H), 4.06-4.03 (m, 2H), 3.80-3.75 (m, 4H), 3.38 (s, 3H), 3.30-3.21 (br m, 4H).

LCMS-ESI$^+$: calc'd for C$_{26}$H$_{30}$N$_6$O$_4$: 491.6 (M+H$^+$). Found: 491.2 (M+H$^+$).

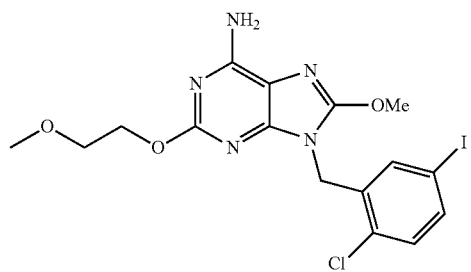

54

Synthesized from compound 40 according to the procedure for compound 7, using 1-(bromomethyl)-2-chloro-5-iodo-benzene.

54: LCMS-ESI$^+$: calc'd for C$_{16}$H$_{17}$ClN$_6$O$_3$: 490.0 (M+H$^+$). Found: 490.0 (M+H$^+$).

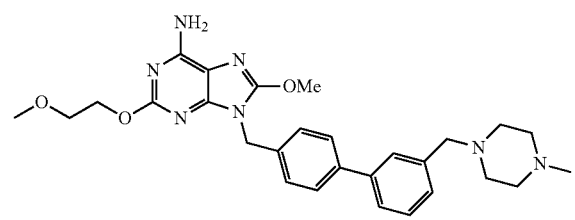

53

Synthesized from compound 46 according to the procedure for compound 9, using 1-(3-(4,4,5,5-tetramethyl-1,3,2-dioxaborolan-2-yl)benzyl)-4-methylpiperazine.

53: $^1$H-NMR: 300 MHz, (CD$_3$OD) δ: 7.64-7.39 (m, 8H), 5.23 (s, 2H), 4.63-4.65 (m, 2H), 4.20 (s, 3H), 3.91 (s, 2H), 3.76 (br m, 2H), 3.31-3.40 (m, 11H), 2.88 (s, 3H).

LCMS-ESI$^+$: calc'd for C$_{28}$H$_{35}$N$_7$O$_3$: 518.6 (M+H$^+$). Found: 518.3 (M+H$^+$).

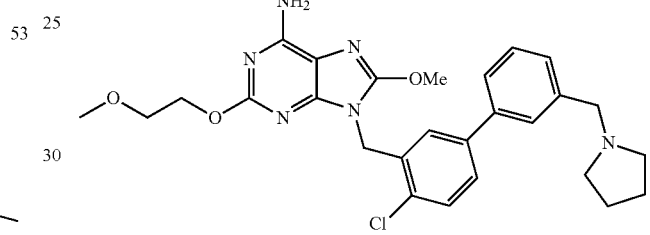

55

Synthesized from compound 54 according to the procedure for compound 9, using 1-(3-(4,4,5,5-tetramethyl-1,3,2-dioxaborolan-2-yl)benzyl)pyrrolidine.

55: $^1$H-NMR: 300 MHz, (CDCl$_3$) δ: 7.75-7.30 (m, 7H), 5.30 (s, 2H), 4.48 (br m, 2H), 4.26 (s, 2H), 4.15 (s, 3H), 3.72-3.66 (m, 4H), 3.36 (s, 3H), 2.87 (br m, 2H), 2.11 (br m, 4H).

LCMS-ESI$^+$: calc'd for C$_{27}$H$_{31}$ClN$_6$O$_3$: 523.0 (M+H$^+$). Found: 523.2 (M+H$^+$).

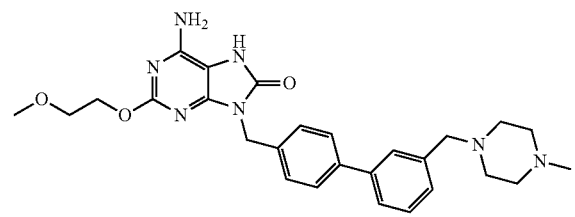

Z

Synthesized from compound 53 according to the procedure for compound A.

Z: $^1$H-NMR: 300 MHz, (CD$_3$OD) δ: 7.74-7.52 (m, 8H), 5.10 (s, 2H), 4.66 (t, J=4.5 Hz, 2H), 4.53 (s, 2H), 3.78-3.65 (m, 10H), 3.38 (s, 3H), 3.01 (s, 3H).

LCMS-ESI$^+$: calc'd for C$_{27}$H$_{33}$N$_7$O$_3$: 504.6 (M+H$^+$). Found: 504.3 (M+H$^+$).

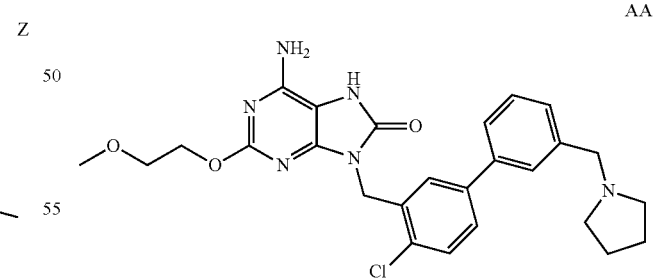

AA

Synthesized from compound 55 according to the procedure for compound A.

AA: $^1$H-NMR: 300 MHz, (CD$_3$OD) δ: 7.74-7.54 (m, 7H), 5.23 (s, 2H), 4.43 (br m, 2H), 3.63-3.51 (m, 6H), 3.34 (s, 3H), 3.20-3.23 (m, 2H), 2.20 (br m, 2H), 2.03 (br m, 2H).

LCMS-ESI$^+$: calc'd for C$_{26}$H$_{29}$ClN$_6$O$_3$: 509.2 (M+H$^+$). Found: 509.1 (M+H$^+$).

56

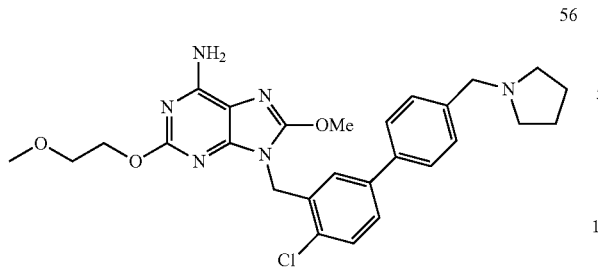

Synthesized from compound 54 according to the procedure for compound 9, using 1-(4-(4,4,5,5-tetramethyl-1,3,2-dioxaborolan-2-yl)benzyl)pyrrolidine.

56: $^1$H-NMR: 300 MHz, (CDCl$_3$) δ: 7.51-7.42 (m, 6H), 7.18 (s, 1H), 5.30 (s, 2H), 4.50 (t, J=4.5 Hz, 2H), 4.25 (s, 2H), 4.16 (s, 3H), 3.69 (br m, 4H), 3.37 (s, 3H), 2.89 (br m, 2H), 2.11 (br m, 4H).

LCMS-ESI$^+$: calc'd for C$_2$H$_{31}$ClN$_6$O$_3$: 523.0 (M+H$^+$). Found: 523.2 (M+H$^+$).

AB

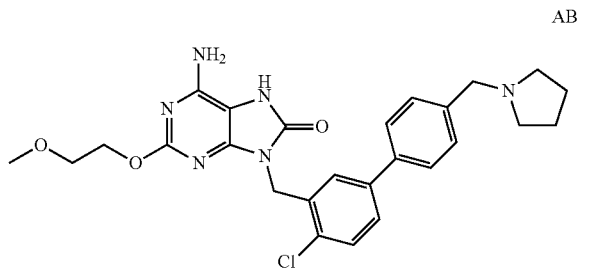 [SMILES: COCCOc1nc(N)c2[nH]c(=O)n(Cc3cc(-c4ccc(CN5CCCC5)cc4)ccc3Cl)c2n1]

Synthesized from compound 56 according to the procedure for compound A.

AB $^1$H-NMR: 300 MHz, (CD$_3$OD) δ: 7.72-7.53 (m, 7H), 5.25 (s, 2H), 4.45 (br m, 2H), 4.42 (s, 2H), 3.62 (br m, 2H), 3.52 (br m, 2H), 3.32 (s, 3H), 3.20-3.23 (m, 2H), 2.20 (br m, 2H), 2.04 (br m, 2H).

LCMS-ESI$^+$: calc'd for C$_{26}$H$_{29}$ClN$_6$O$_3$: 509.2 (M+H$^+$). Found: 509.1 (M+H$^+$).

57

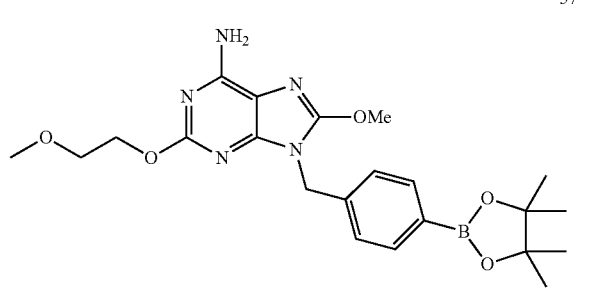

Synthesized from compound 40 according to the procedure for compound 7, using 2-(4-(bromomethyl)phenyl)-4,4,5,5-tetramethyl-1,3,2-dioxaborolane.

57: $^1$H-NMR: 300 MHz, (CDCl$_3$) δ: 7.75 (d, J=3.6 Hz, 2H), 7.30 (d, J=3.6 Hz, 2H), 5.10 (s, 2H), 4.47 (t, J=4.5 Hz, 2H), 4.09 (s, 3H), 3.75 (t, J=4.5 Hz, 2H), 3.43 (s, 3H), 1.33 (s, 12H).

LCMS-ESI$^+$: calc'd for C$_{22}$H$_{30}$BN$_5$O$_5$: 456.3 (M+H$^+$). Found: 456.2 (M+H$^+$).

58

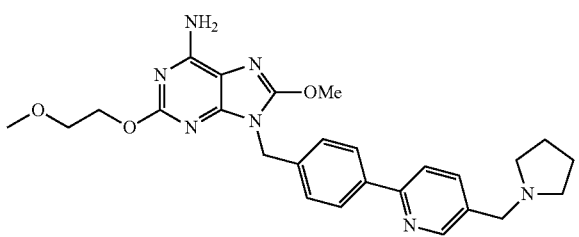

Synthesized from compound 57 according to the procedure for compound 9, using 30.

58: $^1$H-NMR: 300 MHz, (CD$_3$OD) δ: 8.76 (s, 1H), 8.05-7.97 (m, 4H), 7.49 (d, J=8.1 Hz, 2H), 5.26 (s, 2H), 4.64 (t, J=3.9 Hz, 2H), 4.50 (s, 2H), 4.20 (s, 3H), 3.77 (t, J=4.3 Hz, 2H), 3.54 (br m, 4H), 3.39 (s, 3H), 2.20 (br m, 2H), 2.06 (br m, 2H).

LCMS-ESI$^+$: calc'd for C$_{26}$H$_{31}$N$_7$O$_3$: 490.6 (M+H$^+$). Found: 490.1 (M+H$^+$).

AC

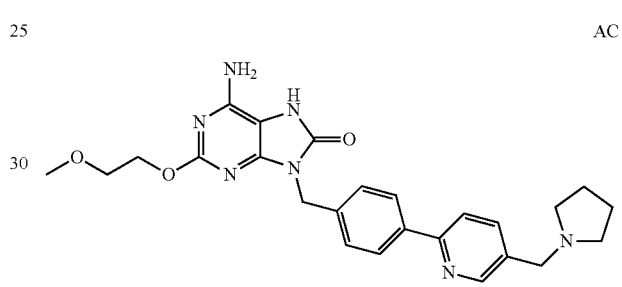

Synthesized from compound 58 according to the procedure for compound A.

AC: $^1$H-NMR: 300 MHz, (CD$_3$OD) δ: 9.11 (s, 1H), 8.76 (d, J=4.2 Hz, 1H), 8.40 (d, J=4.2 Hz, 1H), 8.03 (d, J=3.9 Hz, 2H), 7.72 (dd, J=3.9 Hz, 2H), 5.20 (s, 2H), 4.70 (s, 2H), 4.67 (br m, 2H), 3.76 (br m, 2H), 3.66-3.57 (m, 4H), 3.39 (s, 3H), 2.24-2.22 (m, 2H), 2.09 (br m, 2H).

LCMS-ESI$^+$: calc'd for C$_{25}$H$_{29}$N$_7$O$_3$: 476.5 (M+H$^+$). Found: 476.1 (M+H$^+$).

59

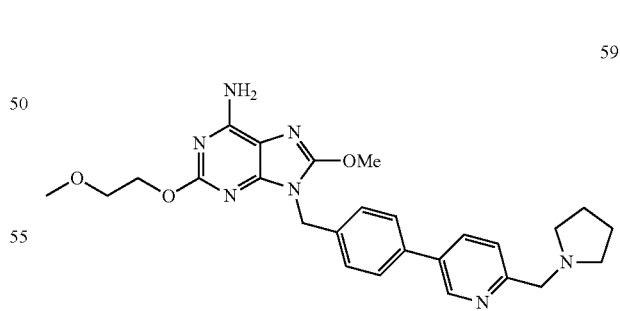

Synthesized from compound 57 according to the procedure for compound 9, using 28.

59: $^1$H-NMR: 300 MHz, (CD$_3$OD) δ: 8.92 (s, 1H), 8.12 (d, J=3.9 Hz, 1H), 7.69 (d, J=4.0 Hz, 2H), 7.55-7.48 (m, 2H), 7.21 (d, J=4.0 Hz, 1H), 5.25 (s, 2H), 4.65-4.59 (m, 4H), 4.19 (s, 3H), 3.78-3.70 (m, 6H), 3.39 (s, 3H), 2.15 (bm, 4H).

LCMS-ESI$^+$: calc'd for C$_{26}$H$_{31}$N$_7$O$_3$: 490.6 (M+H$^+$). Found: 490.1 (M+H$^+$).

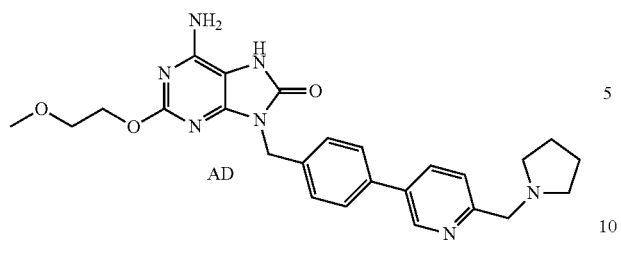

AD

Synthesized from compound 59 according to the procedure for compound A.

AD: $^1$H-NMR: 300 MHz, (CD$_3$OD) δ: 9.01 (s, 1H), 8.30 (d, J=3.9 Hz, 1H), 7.78-7.33 (m, 2H), 7.65-7.59 (m, 2H), 7.40 (d, J=3.6 Hz, 1H), 5.14 (s, 2H), 4.68 (br m, 4H), 3.75-3.58 (m, 6H), 3.38 (s, 3H), 2.16 (bm, 4H).

LCMS-ESI$^+$: calc'd for C$_{26}$H$_{31}$N$_7$O$_3$: 476.5 (M+H$^+$). Found: 476.1 (M+H$^+$).

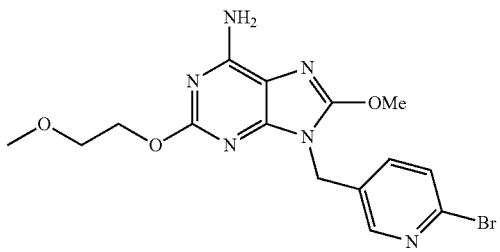

61

Synthesized from compound 40 according to the procedure for compound 7, using 2-bromo-5-(bromomethyl)pyridine.

61: $^1$H-NMR: 300 MHz, (CDCl$_3$) δ: 8.42 (s, 1H), 7.58-7.41 (m, 2H), 5.17 (br s, 2H, NH$_2$), 5.06 (s, 2H), 4.46 (t, J=4.8 Hz, 2H), 4.10 (s, 3H), 3.76 (t, J=4.9 Hz, 2H), 3.44 (s, 3H).

LCMS-ESI$^+$: calc'd for C$_{15}$H$_{17}$BrN$_6$O$_3$: 409.0 (M+H$^+$). Found: 409.0 (M+H$^+$).

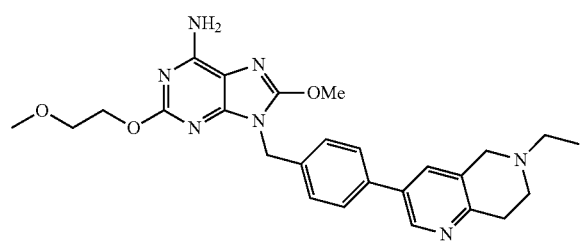

60

Synthesized from compound 57 according to the procedure for compound 9, using 3-bromo-6-ethyl-5,6,7,8-tetrahydro-1,6-naphthyridine.

60: $^1$H-NMR: 300 MHz, (CD$_3$OD) δ: 8.78 (s, 1H), 7.96 (s, 1H), 7.67 (d, J=3.9 Hz, 2H), 7.48 (d, J=3.9 Hz, 2H), 5.23 (s, 2H), 4.56 (bm, 2H), 4.17 (s, 3H), 3.75 (bm, 2H), 3.54-3.44 (m, 4H), 3.39 (s, 3H), 3.08 (br m, 4H), 1.48 (t, J=7.2 Hz, 3H).

LCMS-ESI$^+$: calc'd for C$_{26}$H$_{31}$N$_7$O$_3$: 490.6 (M+H$^+$). Found: 490.0 (M+H$^+$).

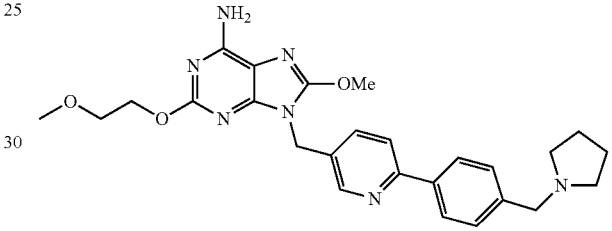

62

Synthesized from compound 61 according to the procedure for compound 9, using 1-(4-(4,4,5,5-tetramethyl-1,3,2-dioxaborolan-2-yl)benzyl)pyrrolidine.

62: $^1$H-NMR: 300 MHz, (CD$_3$OD) δ: 8.64 (s, 1H), 7.93 (d, J=4.2 Hz, 2H), 7.84 (m, 2 Hz, 2H), 7.48 (d, J=4.2 Hz, 2H), 5.21 (s, 2H), 4.46 (t, J=4.6 Hz, 2H), 4.16 (s, 3H), 3.74-3.72 (m, 4H), 3.40 (s, 3H), 2.63 (bm, 4H), 1.84 (bm, 4H).

LCMS-ESI$^+$: calc'd for C$_{26}$H$_{31}$N$_7$O$_3$: 490.6 (M+H$^+$). Found: 490.1 (M+H$^+$).

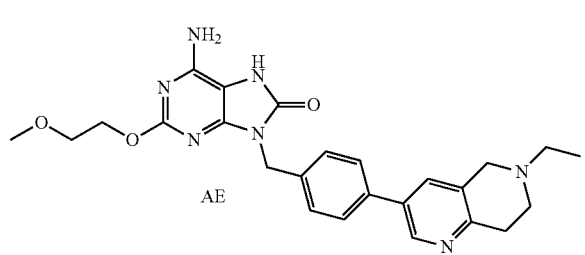 [SMILES: CCN1CCc2ncc(-c3ccc(Cn4c(=O)[nH]c5c(N)nc(OCCOC)nc54)cc3)cc2C1]

AE

Synthesized from compound 60 according to the procedure for compound A.

AE: $^1$H-NMR: 300 MHz, (CD$_3$OD) δ: 8.93 (s, 1H), 8.30 (s, 1H), 7.74 (d, J=4.0 Hz, 2H), 7.60 (d, J=3.9 Hz, 2H), 5.13 (s, 2H), 4.63 (br m, 2H), 3.75 (br m, 2H), 3.57-3.45 (m, 4H), 3.39 (s, 3H), 3.08 (br m, 4H), 1.48 (t, J=7.2 Hz, 3H).

LCMS-ESI$^+$: calc'd for C$_{25}$H$_{29}$N$_7$O$_3$: 476.5 (M+H$^+$). Found: 476.2 (M+H$^+$).

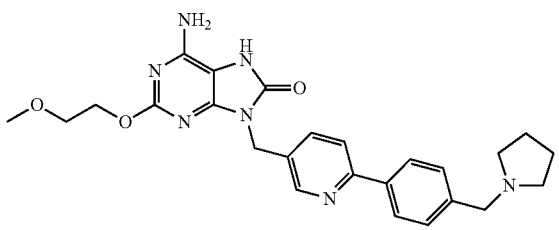

AF

Synthesized from compound 62 according to the procedure for compound A.

AF: $^1$H-NMR: 300 MHz, (CD$_3$OD) δ: 8.97 (s, 1H), 8.60 (br m, 1H), 8.36 (br m, 1H), 8.02 (br m, 2H), 7.85 (br m, 2H), 5.32 (s, 2H), 4.69 (br m, 2H), 4.53 (s, 2H), 3.78 (br m, 2H), 3.57 (br m, 4H), 3.40 (s, 3H), 2.22 (br m, 2H), 2.04 (br m, 2H).

LCMS-ESI$^+$: calc'd for C$_{25}$H$_{29}$N$_7$O$_3$: 476.5 (M+H$^+$). Found: 476.1 (M+H$^+$).

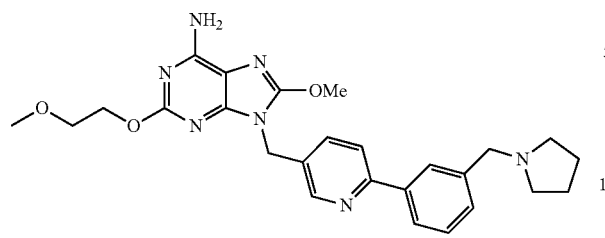

63

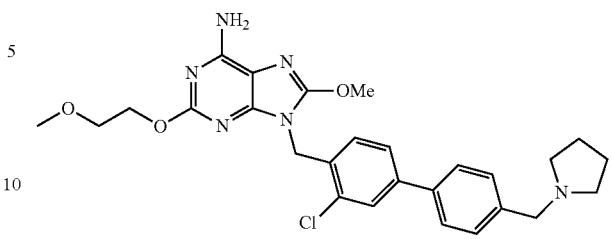

65

Synthesized from compound 61 according to the procedure for compound 9, using 1-(3-(4,4,5,5-tetramethyl-1,3,2-dioxaborolan-2-yl)benzyl)pyrrolidine.

63: $^1$H-NMR: 300 MHz, (CD$_3$OD) δ: 8.69 (s, 1H), 7.97-7.44 (m, 6H), 5.15 (s, 2H), 4.48 (br m, 2H), 4.13 (s, 3H), 3.79 (br m, 4H), 3.46 (s, 3H), 2.70 (br m, 4H), 1.87 (br m, 4H).

LCMS-ESI$^+$: calc'd for C$_{26}$H$_{31}$N$_7$O$_3$: 490.6 (M+H$^+$). Found: 490.2 (M+H$^+$).

Synthesized from compound 64 according to the procedure for compound 9, using 1-(4-(4,4,5,5-tetramethyl-1,3,2-dioxaborolan-2-yl)benzyl)pyrrolidine.

65: $^1$H-NMR: 300 MHz, (CD$_3$OD) δ: 7.67-7.38 (m, 7H), 5.25 (s, 2H), 4.37 (t, J=4.8 Hz, 2H), 4.10 (s, 3H), 3.67-3.64 (m, 4H), 3.34 (s, 3H), 2.56 (br m, 4H), 1.81 (br m, 4H).

LCMS-ESI$^+$: calc'd for C$_{27}$H$_{31}$ClN$_6$O$_3$: 523.0 (M+H$^+$). Found: 523.1 (M+H$^+$).

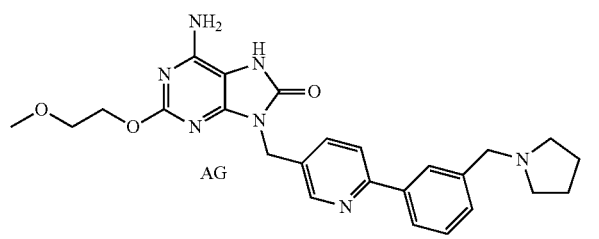 [SMILES: COCCOc1nc(N)c2[nH]c(=O)n(Cc3ccc(-c4cccc(CN5CCCC5)c4)nc3)c2n1]

AG

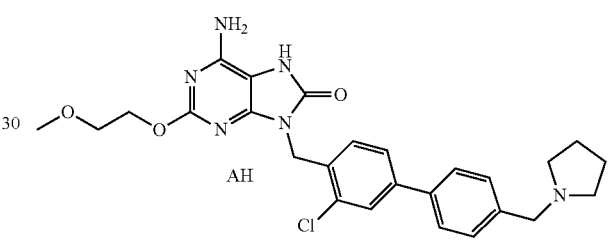

AH

Synthesized from compound 63 according to the procedure for compound A.

AG: $^1$H-NMR: 300 MHz, (CD$_3$OD) δ: 8.99 (s, 1H), 8.64 (br m, 1H), 8.42 (br m, 1H), 8.29 (s, 1H), 8.07 (br m, 1H), 7.87-7.77 (m, 2H), 5.34 (s, 2H), 4.70 (br m, 2H), 4.55 (s, 2H), 3.79 (br m, 2H), 3.57 (br m, 4H), 3.40 (s, 3H), 2.22 (br m, 2H), 2.07 (br m, 2H).

LCMS-ESI$^+$: calc'd for C$_{25}$H$_{29}$N$_7$O$_3$: 476.5 (M+H$^+$). Found: 476.2 (M+H$^+$).

Synthesized from compound 65 according to the procedure for compound A.

AH: $^1$H-NMR: 300 MHz, (CD$_3$OD) δ: 7.76-7.44 (m, 7H), 5.23 (s, 2H), 4.58 (br m, 2H), 4.44 (s, 2H), 3.70 (br m, 2H), 3.56-3.50 (m, 2H), 3.33 (s, 3H), 3.26-3.23 (m, 2H), 2.20 (br m, 2H), 2.04 (br m, 2H).

LCMS-ESI$^+$: calc'd for C$_{26}$H$_{29}$ClN$_6$O$_3$: 509.9 (M+H$^+$). Found: 509.1 (M+H$^+$).

64

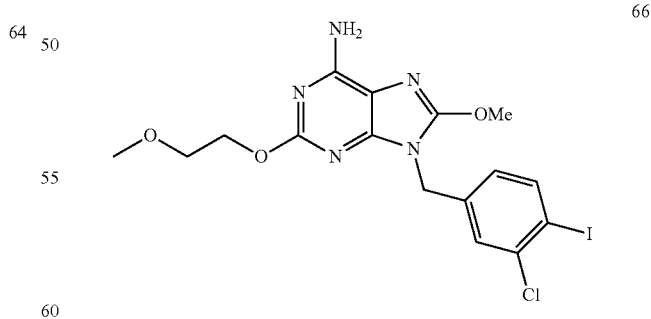

66

Synthesized from compound 40 according to the procedure for compound 7, using 1-(bromomethyl)-2-chloro-4-iodobenzene.

64: LCMS-ESI$^+$: calc'd for C$_{16}$H$_{17}$ClN$_5$O$_3$: 490.0 (M+H$^+$). Found: 490.0 (M+H+).

Synthesized from compound 40 according to the procedure for compound 7, using 1-(bromomethyl)-3-chloro-4-iodobenzene.

66: LCMS-ESI$^+$: calc'd for C$_{16}$H$_{17}$ClN$_6$O$_3$: 490.0 (M+H$^+$). Found: 490.0 (M+H$^+$).

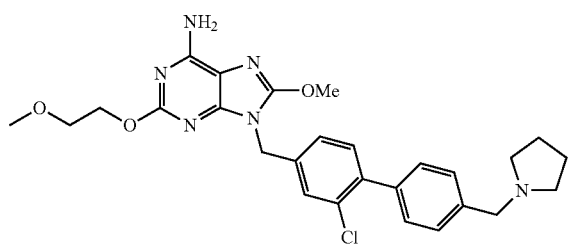

67

Synthesized from compound 66 according to the procedure for compound 9, using 1-(4-(4,4,5,5-tetramethyl-1,3,2-dioxaborolan-2-yl)benzyl)pyrrolidine.

67: $^{1}$H-NMR: 300 MHz, (CD$_3$OD) δ: 7.47-7.30 (m, 7H), 5.14 (s, 2H), 4.54 (t, J=4.7 Hz, 2H), 4.17 (s, 3H), 3.73 (t, J=4.5 Hz, 2H), 3.69 (s, 2H), 3.39 (s, 3H), 2.60 (br m, 4H), 1.83 (br m, 4H).

LCMS-ESI$^+$: calc'd for C$_{27}$H$_{31}$ClN$_6$O$_3$: 523.0 (M+H$^+$). Found: 523.2 (M+H$^+$).

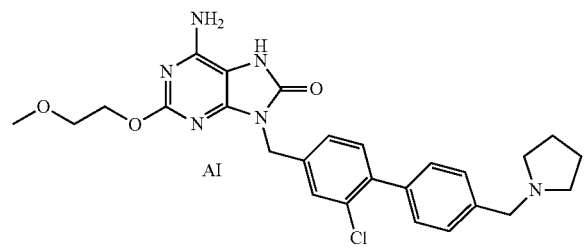

AI

Synthesized from compound 67 according to the procedure for compound A.

AI: $^{1}$H-NMR: 300 MHz, (CD$_3$OD) δ: 7.67-7.36 (m, 7H), 5.23 (s, 2H), 4.70 (br m, 2H), 4.46 (s, 2H), 3.78 (br m, 2H), 3.59-3.53 (m, 2H), 3.38 (s, 3H), 3.27-3.23 (m, 2H), 2.20 (br m, 2H), 2.04 (br m, 2H).

LCMS-ESI$^+$: calc'd for C$_{26}$H$_{29}$ClN$_6$O$_3$: 509.9 (M+H$^+$). Found: 509.1 (M+H$^+$).

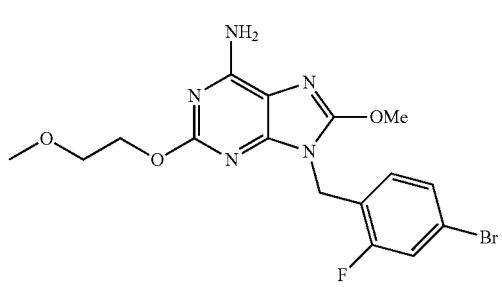

68

Synthesized from compound 40 according to the procedure for compound 7, using 1-(bromomethyl)-2-fluoro-4-bromobenzene.

68: LCMS-ESI$^+$: calc'd for C$_{16}$H$_{17}$BrN$_6$O$_3$: 426.0; (M+H$^+$). Found: 426.0 (M+H$^+$).

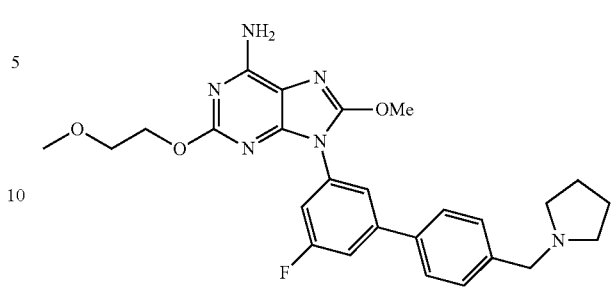

69

Synthesized from compound 68 according to the procedure for compound 9, using 1-(4-(4,4,5,5-tetramethyl-1,3,2-dioxaborolan-2-yl)benzyl)pyrrolidine.

69: $^{1}$H-NMR: 300 MHz, (CD$_3$OD) δ: 7.58 (d, J=4.2 Hz, 2H), 7.43-7.36 (m, 4H), 7.23 (t, J=9 Hz, 1H), 5.21 (s, 2H), 4.42 (t, J=4.9 Hz, 2H), 4.12 (s, 3H), 3.72-3.68 (m, 4H), 3.37 (s, 3H), 2.62 (br m, 4H), 1.86-1.82 (m, 4H).

LCMS-ESI$^+$: calc'd for C$_{27}$H$_{31}$FN$_6$O$_3$: 507.2 (M+H$^+$). Found: 507.2 (M+H$^+$).

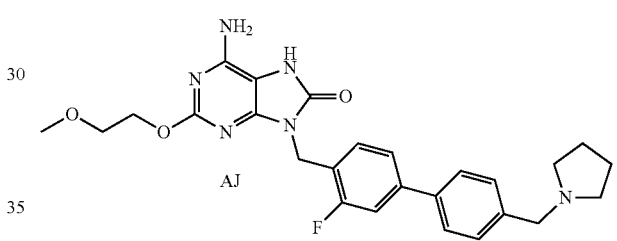

AJ

Synthesized from compound 69 according to the procedure for compound A.

AJ: $^{1}$H-NMR: 300 MHz, (CD$_3$OD) δ: 7.67-7.44 (m, 7H), 5.17 (s, 2H), 4.64 (br m, 2H), 4.44 (s, 2H), 3.74-3.72 (m, 2H), 3.56-3.52 (m, 2H), 3.36 (s, 3H), 3.28-3.23 (m, 2H), 2.22-2.20 (m, 2H), 2.04 (br m, 2H).

LCMS-ESI$^+$: calc'd for C$_{26}$H$_{29}$FN$_6$O$_3$: 493.5 (M+H$^+$). Found: 493.1 (M+H$^+$).

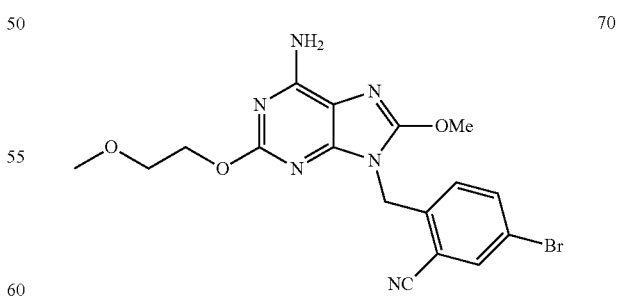

70

Synthesized from compound 40 according to the procedure for compound 7, using 1-(bromomethyl)-2-cyano-4-bromobenzene.

70: LCMS-ESI$^+$: calc'd for C$_{17}$H$_{17}$BrN$_6$O$_3$: 433.0; (M+H$^+$). Found: 433.0 (M+H$^+$).

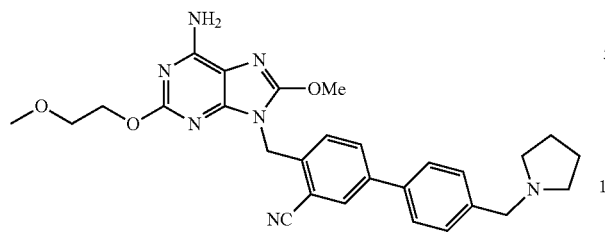

71

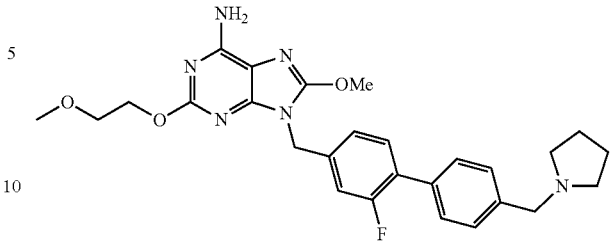

73

Synthesized from compound 70 according to the procedure for compound 9, using 1-(4-(4,4,5,5-tetramethyl-1,3,2-dioxaborolan-2-yl)benzyl)pyrrolidine.

71: ¹H-NMR: 300 MHz, (CD₃OD) δ: 8.02-7.38 (m, 7H), 5.36 (s, 2H), 4.41 (t, J=4.8 Hz, 2H), 4.14 (s, 3H), 3.70-3.66 (m, 4H), 3.35 (s, 3H), 2.59 (br m, 4H), 1.84-1.82 (m, 4H).

LCMS-ESI⁺: calc'd for $C_{28}H_{31}N_7O_3$: 514.6 (M+H⁺). Found: 514.2 (M+H⁺).

Synthesized from compound 72 according to the procedure for compound 9, using 1-(4-iodobenzyl)pyrrolidine.

73: ¹H-NMR: 300 MHz, (CD₃OD) δ: 7.57 (d, J=4.2 Hz, 2H), 7.42-7.36 (m, 4H), 7.23 (t, J=9 Hz, 1H), 5.21 (s, 2H), 4.42 (t, J=4.8 Hz, 2H), 4.12 (s, 3H), 3.72-3.68 (m, 4H), 3.37 (s, 3H), 2.59 (br m, 4H), 1.84-1.81 (m, 4H).

LCMS-ESI⁺: calc'd for $C_{27}H_{31}FN_7O_3$: 507.6 (M+H⁺). Found: 507.1 (M+H⁺).

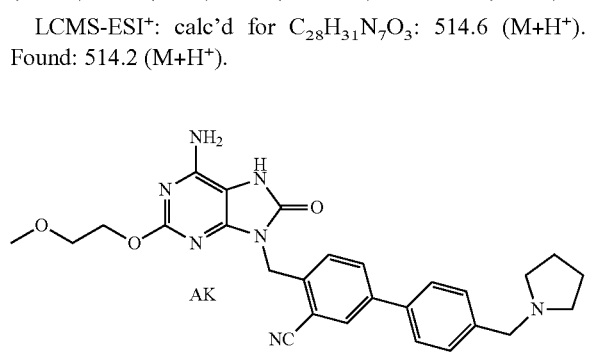

AK

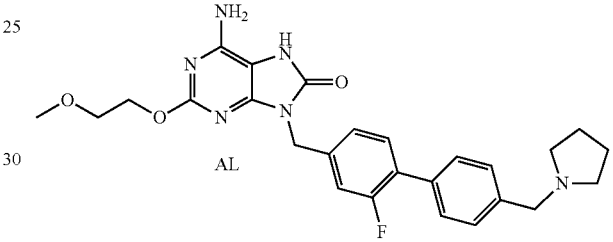

AL

Synthesized from compound 71 according to the procedure for compound A.

AK: ¹H-NMR: 300 MHz, (CD₃OD) δ: 8.09-7.69 (m, 7H), 5.32 (s, 2H), 4.68 (br m, 2H), 4.46 (s, 2H), 3.73 (br m, 2H), 3.59-3.53 (m, 2H), 3.35 (s, 3H), 3.28-3.23 (m, 2H), 2.21 (br m, 2H), 2.06 (br m, 2H).

LCMS-ESI⁺: calc'd for $C_{27}H_{29}N_7O_3$: 500.5 (M+H⁺). Found: 500.1 (M+H⁺).

Synthesized from compound 73 according to the procedure for compound A.

AL: ¹H-NMR: 300 MHz, (CD₃OD) δ: 7.75-7.44 (m, 7H), 5.17 (s, 2H), 4.63 (t, J=4.0 Hz, 2H), 4.45 (s, 2H), 3.74 (t, J=3 Hz, 2H), 3.58-3.53 (m, 2H), 3.35 (s, 3H), 3.28-3.23 (m, 2H), 2.20 (br m, 2H), 2.04 (br m, 2H).

LCMS-ESI⁺: calc'd for $C_{26}H_{29}FN_6O_3$: 493.5 (M+H⁺). Found: 493.1 (M+H⁺).

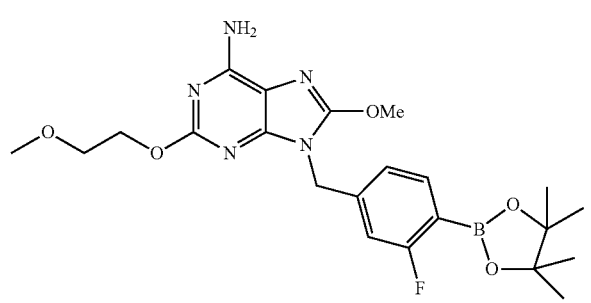

72

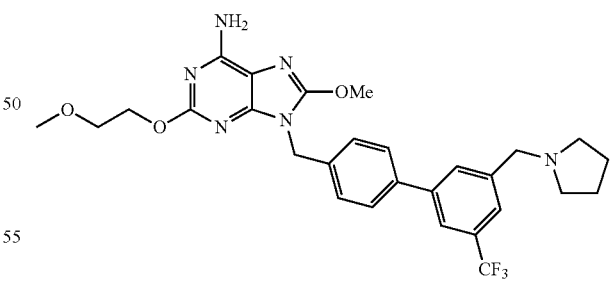

74

Synthesized from compound 40 according to the procedure for compound 7, using 2-(4-(bromomethyl)-2-fluorophenyl)-4,4,5,5-tetramethyl-1,3,2-dioxaborolane.

72: LCMS-ESI⁺: calc'd for $C_{22}H_{29}BFN_5O_5$: 474.2; (M+H⁺). Found: 474.2 (M+H⁺).

Synthesized from compound 46 according to the procedure for compound 9, using 1-(3-(4,4,5,5-tetramethyl-1,3,2-dioxaborolan-2-yl)-5-(trifluoromethyl)benzyl)pyrrolidine.

74: ¹H-NMR: 300 MHz, (CD₃OD) δ: 7.82 (s, 1H), 7.76 (s, 1H), 7.63-7.40 (m, 5H), 5.16 (s, 2H), 4.44 (t, J=4.6 Hz, 2H), 4.12 (s, 3H), 3.75-3.70 (m, 4H), 3.37 (s, 3H), 2.57 (br m, 4H), 1.83-1.81 (m, 4H).

LCMS-ESI⁺: calc'd for $C_{28}H_{31}F_3N_6O_3$: 557.6 (M+H⁺). Found: 557.2 (M+H⁺).

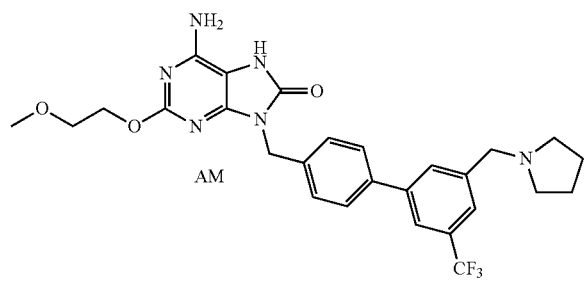

AM

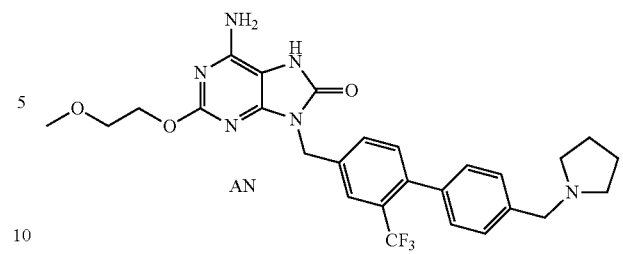

AN

Synthesized from compound 74 according to the procedure for compound A.

AM: $^1$H-NMR: 300 MHz, (CD$_3$OD) δ: 8.20-7.57 (m, 7H), 5.13 (s, 2H), 4.68 (br m, 2H), 4.47 (s, 2H), 3.77 (br m, 2H), 3.59-3.56 (m, 2H), 3.38 (s, 3H), 3.28-3.23 (m, 2H), 2.22 (br m, 2H), 2.06 (br m, 2H).

LCMS-ESI$^+$: calc'd for C$_{27}$H$_{29}$F$_3$N$_6$O$_3$: 543.5 (M+H$^+$). Found: 543.2 (M+H$^+$).

Synthesized from compound 76 according to the procedure for compound A.

AN: $^1$H-NMR: 300 MHz, (CD$_3$OD) δ: 7.93-7.39 (m, 7H), 5.13 (s, 2H), 4.69 (br m, 2H), 4.46 (s, 2H), 3.77 (br m, 2H), 3.59-3.54 (m, 2H), 3.39 (s, 3H), 3.28-3.23 (m, 2H), 2.22 (br m, 2H), 2.06 (br m, 2H).

LCMS-ESI$^+$: calc'd for C$_{27}$H$_{29}$F$_3$N$_6$O$_3$: 543.5 (M+H$^+$). Found: 543.1 (M+H$^+$).

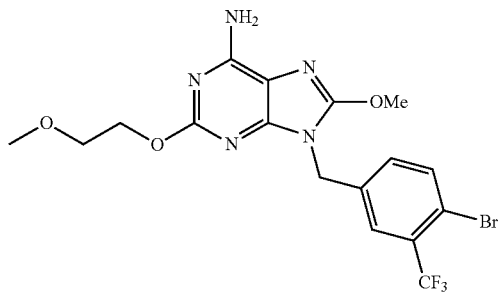

75

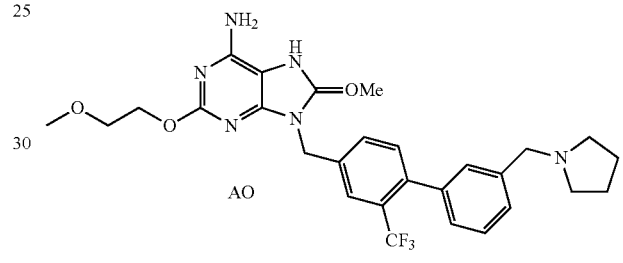

AO

Synthesized from compound 40 according to the procedure for compound 7, using 1-(bromomethyl)-3-trifluoromethyl-4-bromobenzene.

75: $^1$H-NMR: 300 MHz, (CD$_3$OD) δ: 7.69-7.33 (m, 3H), 5.07 (s, 2H), 4.44 (br m, 2H), 4.09 (s, 3H), 3.73 (br m, 2H), 3.41 (s, 3H).

LCMS-ESI$^+$: calc'd for C$_{17}$H$_{17}$BrF$_3$N$_5$O$_3$: 476.0 (M+H$^+$). Found: 476.0 (M+H$^+$).

Synthesized from compound 75 according to the procedure for compound 9, using 1-(3-(4,4,5,5-tetramethyl-1,3,2-dioxaborolan-2-yl)benzyl)pyrrolidine.

77: $^1$H-NMR: 300 MHz, (CD$_3$OD) δ: 7.79 (s, 1H), 7.56 (d, J=3.9 Hz, 1H), 7.39-7.24 (m, 5H), 5.23 (s, 2H), 4.45 (t, J=4.6 Hz, 2H), 4.15 (s, 3H), 3.72 (t, J=4.8 Hz, 2H), 3.69 (s, 2H), 3.39 (s, 3H), 2.58 (br m, 4H), 1.83-1.81 (m, 4H).

LCMS-ESI$^+$: calc'd for C$_{28}$H$_{31}$F$_3$N$_6$O$_3$: 557.6 (M+H$^+$). Found: 557.2 (M+H$^+$).

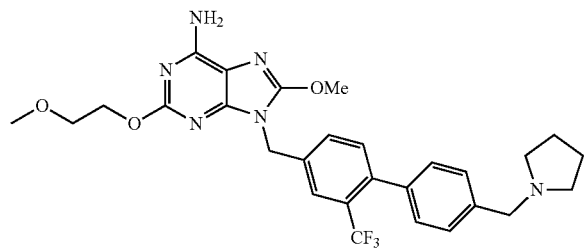 [SMILES: COCCOc1nc(N)c2[nH]c(=O)n(Cc3ccc(-c4ccc(CN5CCCC5)cc4)c(C(F)(F)F)c3)c2n1]

76

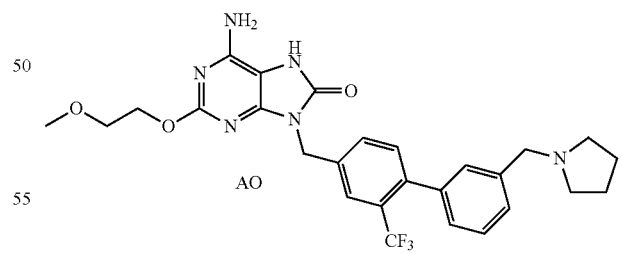

AO

Synthesized from compound 75 according to the procedure for compound 9, using 1-(4-(4,4,5,5-tetramethyl-1,3,2-dioxaborolan-2-yl)benzyl)pyrrolidine.

76: $^1$H-NMR: 300 MHz, (CD$_3$OD) δ: 7.79 (s, 1H), 7.56 (d, J=3.9 Hz, 1H), 7.39-7.24 (m, 5H), 5.23 (s, 2H), 4.45 (t, J=4.6 Hz, 2H), 4.15 (s, 3H), 3.74-3.71 (m, 4H), 3.39 (s, 3H), 2.60 (br m, 4H), 1.85-1.82 (m, 4H).

LCMS-ESI$^+$: calc'd for C$_{28}$H$_{31}$F$_3$N$_6$O$_3$: 557.6 (M+H$^+$). Found: 557.2 (M+H$^+$).

Synthesized from compound 77 according to the procedure for compound A.

AO: $^1$H-NMR: 300 MHz, (CD$_3$OD) δ: 7.93-7.39 (m, 7H), 5.19 (s, 2H), 4.69 (br m, 2H), 4.45 (s, 2H), 3.79 (br m, 2H), 3.50 (br m, 2H), 3.39 (s, 3H), 3.28-3.23 (m, 2H), 2.21-2.18 (m, 2H), 2.04 (br m, 2H).

LCMS-ESI$^+$: calc'd for C$_{27}$H$_{29}$F$_3$N$_6$O$_3$: 543.5 (M+H$^+$). Found: 543.2 (M+H$^+$).

75

78

Synthesized from 3-(5-bromopyridin-2-yl)propanal according to the procedure for compound 28.

78: $^1$H-NMR: 300 MHz, (CDCl$_3$) δ: 8.57 (d, 1H, J=2 Hz), 7.70 (dd, 1H, J=8, 2 Hz), 7.07 (d, 1H, J=8 Hz), 2.80 (t, 2H, J=7 Hz), 2.55 (m, 6H), 1.94 (m, 2H), 1.80 (m, 4H).

LCMS-ESI$^+$: calc'd for C$_{12}$H$_{18}$BrN$_2$: 270.2 (M+H$^+$). Found: 269.1 [271.1] (M+H$^+$)-bromine isotopes.

79

Synthesized from compound 46 according to the procedure for compound 9, using 78.

79: $^1$H-NMR: 300 MHz, (CDCl$_3$) δ: 8.71 (s, 1H), 7.75 (d, 1H, J=8 Hz), 7.49 (d, 2H, J=8 Hz), 7.42 (d, 2H, J=8 Hz), 7.22 (d, 1H, J=8 Hz), 5.17 (br s, 2H), 5.14 (s, 2H), 4.78 (t, 2H, J=7 Hz), 4.12 (s, 3H), 3.76 (d, 2H, J=7 Hz), 3.43 (s, 3H), 2.87 (t, 2H, J=7 Hz), 2.54 (m, 6H), 1.99 (m, 2H), 1.79 (m, 4H).

LCMS-ESI$^+$: calc'd for C$_{28}$H$_{36}$N$_7$O$_3$: 518.3 (M+H$^+$). Found: 518.2 (M+H$^+$).

AP

Synthesized from compound 79 according to the procedure for compound A.

AP: $^1$H-NMR: 300 MHz, (CD$_3$OD) δ: 9.07 (s, 1H), 8.86 (br m, 1H), 8.15 (br m, 1H), 7.84 (br d, 2H, J=8 Hz), 7.65 (br d, 2H, J=8 Hz), 5.16 (s, 2H), 4.67 (br m, 2H), 3.73 (br m, 4H), 3.39 (s, 3H) 3.30 (m, 2H), 3.14 (br m, 4H), 2.06-2.32 (br m, 6H).

LCMS-ESI$^+$: calc'd for C$_{27}$H$_{34}$N$_7$O$_3$: 504.3 (M+H$^+$). Found: 504.1 (M+H$^+$).

76

80

Synthesized from compound 45 according to the procedure for compound 7, using 4-iodobenzyl bromide.

80: LCMS-ESI$^+$: calc'd for C$_{19}$H$_{22}$IN$_5$O$_3$: 496.1; (M+H$^+$). Found: 496.0 (M+H$^+$).

81

Synthesized from compound 80 according to the procedure for compound 9, using 1-(3-(4,4,5,5-tetramethyl-1,3,2-dioxaborolan-2-yl)benzyl)pyrrolidine.

81: $^1$H-NMR: 300 MHz, (CD$_3$OD) δ: 7.60-7.33 (m, 8H), 5.16 (s, 2H), 4.19-4.17 (m, 2H), 4.13 (s, 3H), 3.97-3.93 (m, 2H), 3.74 (s, 2H), 3.42-3.35 (m, 2H), 2.63 (br m, 4H), 2.01 (br m, 1H), 1.85-1.82 (m, 4H), 1.76-1.72 (m, 2H), 1.43-1.40 (m, 2H).

LCMS-ESI$^+$: calc'd for C$_{30}$H$_{36}$N$_6$O$_3$: 529.6 (M+H$^+$). Found: 529.2 (M+H$^+$).

AQ

Synthesized from compound 81 according to the procedure for compound A.

AQ: $^1$H-NMR: 300 MHz, (CD$_3$OD) δ: 7.90 (s, 1H), 7.17-7.54 (m, 7H), 5.16 (s, 2H), 4.46-4.34 (m, 4H), 3.95-3.92 (m, 2H), 3.52 (br m, 2H), 3.44-3.37 (m, 2H), 3.28 (br m, 2H), 2.17-2.04 (m, 5H), 1.72-1.68 (m, 2H), 1.40 (br m, 2H).

LCMS-ESI$^+$: calc'd for C$_{29}$H$_{34}$N$_6$O$_3$: 515.6 (M+H$^+$). Found: 515.3 (M+H$^+$).

82

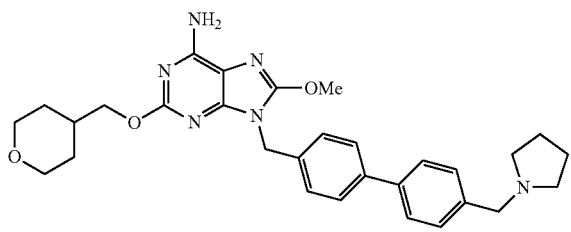

Synthesized from compound 80 according to the procedure for compound 9, using 1-(4-(4,4,5,5-tetramethyl-1,3,2-dioxaborolan-2-yl)benzyl)pyrrolidine.

82: $^1$H-NMR: 300 MHz, (CD$_3$OD) δ: 7.59-7.54 (m, 4H), 7.41-7.35 (m, 4H), 5.16 (s, 2H), 4.19-4.17 (m, 2H), 4.13 (s, 3H), 3.97-3.93 (m, 2H), 3.66 (s, 2H), 3.45-3.38 (m, 2H), 2.57 (br m, 4H), 2.03 (br m, 1H), 1.82 (br m, 4H), 1.77-1.72 (m, 2H), 1.45-1.40 (m, 2H).

LCMS-ESI$^+$: calc'd for C$_{30}$H$_{36}$N$_6$O$_3$: 529.6 (M+H$^+$). Found: 529.1 (M+H$^+$).

AR

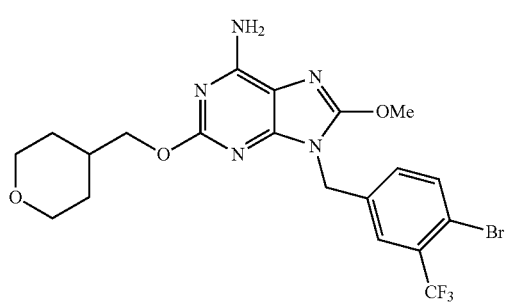

Synthesized from compound 82 according to the procedure for compound A.

AR: $^1$H-NMR: 300 MHz, (CD$_3$OD) δ: 7.73-7.54 (m, 8H), 5.12 (s, 2H), 4.43 (br m, 4H), 3.96-3.93 (m, 2H), 3.52 (br m, 2H), 3.44-3.37 (m, 2H), 3.22 (br m, 2H), 2.20-2.03 (m, 5H), 1.72-1.68 (m, 2H), 1.45-1.40 (m, 2H).

LCMS-ESI$^+$: calc'd for C$_{29}$H$_{34}$N$_6$O$_3$: 515.6 (M+H$^+$). Found: 515.1 (M+H$^+$).

83

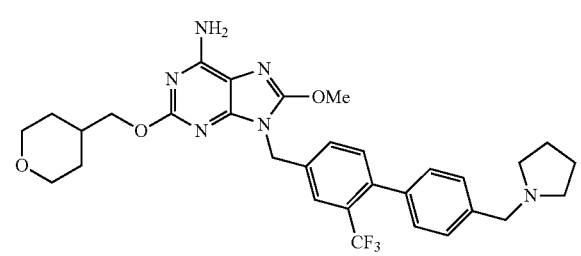

Synthesized from compound 45 according to the procedure for compound 7, using 1-(bromomethyl)-3-trifluoromethyl-4-bromobenzene.

83: $^1$H-NMR: 300 MHz, (CD$_3$OD) δ: 7.74-7.32 (m, 3H), 5.32-5.29 (m, 2H), 5.08 (s, 2H), 4.14-3.98 (m, 5H), 3.45-3.38 (m, 2H), 2.08 (br m, 1H), 1.80-1.76 (m, 2H), 1.45-1.38 (m, 2H).

LCMS-ESI$^+$: calc'd for C$_{20}$H$_{21}$BrF$_3$N$_5$O$_3$: 516.1 (M+H$^+$). Found: 516.0 (M+H$^+$).

84

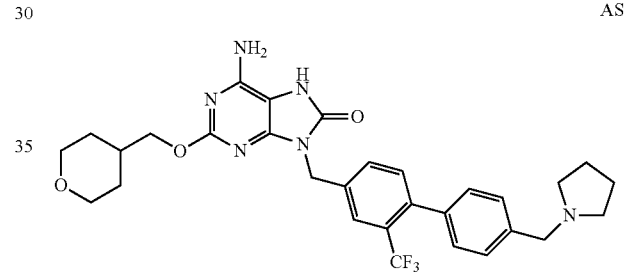

Synthesized from compound 83 according to the procedure for compound 9, using 1-(4-(4,4,5,5-tetramethyl-1,3,2-dioxaborolan-2-yl)benzyl)pyrrolidine.

84: $^1$H-NMR: 300 MHz, (CD$_3$OD) δ: 7.80-7.23 (m, 7H), 5.23 (s, 2H), 4.19-4.17 (m, 2H), 4.15 (s, 3H), 3.97-3.93 (m, 2H), 3.47 (s, 2H), 3.46-3.38 (m, 2H), 2.58 (br m, 4H), 2.03 (br m, 1H), 1.84-1.80 (m, 4H), 1.77-1.72 (m, 2H), 1.45-1.39 (m, 2H).

LCMS-ESI$^+$: calc'd for C$_{31}$H$_{35}$F$_3$N$_6$O$_3$: 597.6 (M+H$^+$). Found: 597.2 (M+H$^+$).

AS

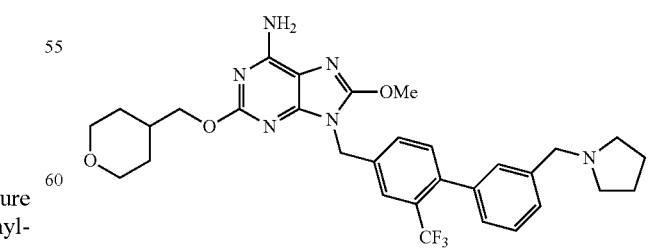

Synthesized from compound 84 according to the procedure for compound A.

AS: $^1$H-NMR: 300 MHz, (CD$_3$OD) δ: 7.93-7.38 (m, 7H), 5.19 (s, 2H), 4.48-4.42 (m, 4H), 3.96-3.93 (m, 2H), 3.59-3.41 (m, 4H), 3.22 (br m, 2H), 2.21-2.05 (m, 5H), 1.75-1.72 (m, 2H), 1.46-1.39 (m, 2H).

LCMS-ESI$^+$: calc'd for C$_{30}$H$_{33}$F$_3$N$_6$O$_3$: 583.6 (M+H$^+$). Found: 583.2 (M+H$^+$).

85

Synthesized from compound 83 according to the procedure for compound 9, using 1-(3-(4,4,5,5-tetramethyl-1,3,2-dioxaborolan-2-yl)benzyl)pyrrolidine.

85: $^1$H-NMR: 300 MHz, (CD$_3$OD) δ: 7.80 (s, 1H), 7.57-7.23 (m, 6H), 5.24 (s, 2H), 4.19-4.17 (m, 2H), 4.16 (s, 3H), 3.98-3.93 (m, 2H), 3.68 (s, 2H), 3.47-3.40 (m, 2H), 2.56 (br m, 4H), 2.03 (br m, 1H), 1.82-1.73 (m, 6H), 1.44-1.34 (m, 2H).

LCMS-ESI$^+$: calc'd for C$_{31}$H$_{35}$F$_3$N$_6$O$_3$: 597.6 (M+H$^+$). Found: 597.2 (M+H$^+$).

87: $^1$H-NMR: 300 MHz, (CDCl$_3$) δ: 8.74 (s, 1H), 7.82 (d, 1H, J=8 Hz), 7.51 (m, 3H), 7.42 (d, 2H, J=8 Hz), 5.16 (br s, 4H), 4.17 (d, 2H, J=7 Hz), 4.10 (s, 3H), 4.00 (m, 2H), 3.91 (s, 2H), 3.42 (t, 2H, J=12 Hz), 2.73 (br s, 4H), 2.10 (br m, 1H), 1.83 (m, 6H), 1.46 (m, 2H).

LCMS-ESI$^+$: calc'd for C$_{29}$H$_{36}$N$_7$O$_3$: 530.3 (M+H$^+$). Found: 530.1 (M+H$^+$).

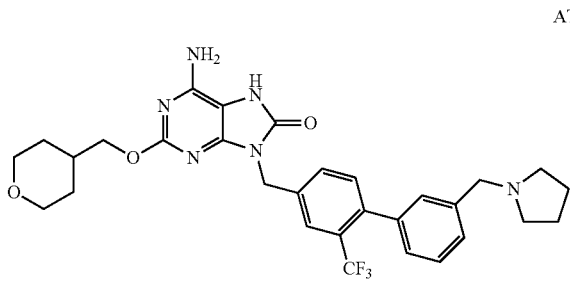

AT

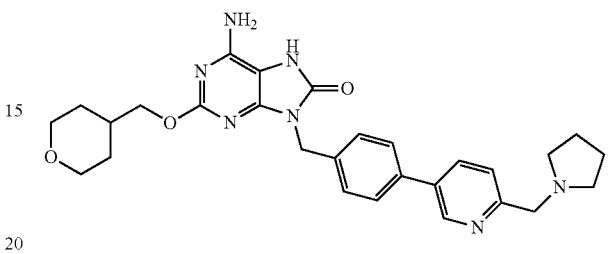

AU

Synthesized from compound 85 according to the procedure for compound A.

AT: $^1$H-NMR: 300 MHz, (CD$_3$OD) δ: 7.94-7.42 (m, 7H), 5.20 (s, 2H), 4.44 (br m, 4H), 3.99-3.96 (m, 2H), 3.59-3.44 (m, 4H), 3.22 (br m, 2H), 2.21-2.04 (m, 5H), 1.72 (br m, 2H), 1.43 (m, 2H).

LCMS-ESI$^+$: calc'd for C$_{30}$H$_{33}$F$_3$N$_6$O$_3$: 583.6 (M+H$^+$). Found: 583.2 (M+H$^+$).

Synthesized from compound 87 according to the procedure for compound A.

AU: $^1$H-NMR: 300 MHz, (CD$_3$OD) δ: 8.99 (s, 1H), 8.27 (d, 2H, J=6 Hz), 7.73 (m, 3H), 7.59 (d, 2H, J=8 Hz), 5.14 (s, 2H), 4.67 (s, 2H), 4.42 (d, 2H, J=6 Hz), 3.94 (dd, 2H, J=11, 3 Hz), 3.49 (br m, 4H), 3.41 (t, 2H, J=11 Hz), 2.16 (br m, 4H), 1.70 (d, 2H, J=11 Hz), 1.44 (m, 2H).

LCMS-ESI$^+$: calc'd for C$_{28}$H$_{34}$N$_7$O$_3$: 516.3 (M+H$^+$). Found: 516.1 (M+H$^+$).

86

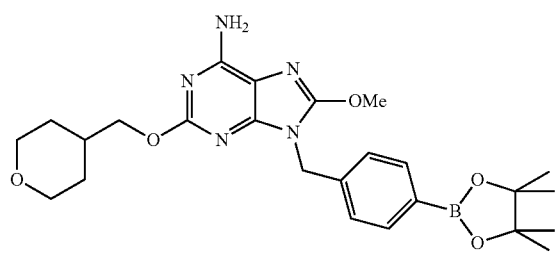

88

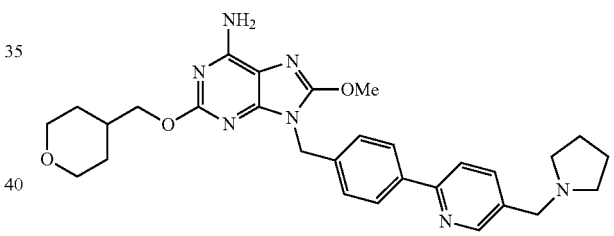

Synthesized from compound 45 according to the procedure for compound 7, using 2-(4-(bromomethyl)phenyl)-4,4,5,5-tetramethyl-1,3,2-dioxaborolane.

86: $^1$H-NMR: 300 MHz, (CDCl$_3$) δ: 7.74 (d, 2H, J=8 Hz), 7.28 (d, 2H, J=8 Hz), 5.36 (br s, 2H), 5.11 (s, 2H), 4.13 (d, 2H, J=7 Hz), 4.06 (s, 2H), 3.98 (dd, 2H, J=11, 4 Hz), 3.41 (t, 2H, J=11 Hz), 2.04 (m, 1H), 1.77 (d, 2H, J=11 Hz), 1.44 (m, 2H), 1.32 (s, 12H).

LCMS-ESI$^+$: calc'd for C$_{25}$H$_{35}$BN$_5$O$_5$: 496.3 (M+H$^+$). Found: 496.2 (M+H+).

Synthesized from compound 86 according to the procedure for compound 9, using 30.

88: $^1$H-NMR: 300 MHz, (CDCl$_3$) δ: 8.60 (s, 1H), 7.93 (d, 2H, J=8 Hz), 7.80 (d, 1H, J=8 Hz), 7.66 (d, 1H, J=8 Hz), 7.41 (d, 2H, J=8 Hz), 5.20 (br s, 2H), 5.16 (s, 2H), 4.17 (d, 2H, J=7 Hz), 4.10 (s, 3H), 4.00 (br d, 2H, J=7 Hz), 3.71 (s, 2H), 3.42 (m, 2H), 2.60 (br s, 4H), 2.08 (m, 1H), 1.83 (m, 6H), 1.43 (m, 2H).

LCMS-ESI$^+$: calc'd for C$_{29}$H$_{36}$N$_7$O$_3$: 530.3 (M+H$^+$). Found: 530.1 (M+H$^+$).

87

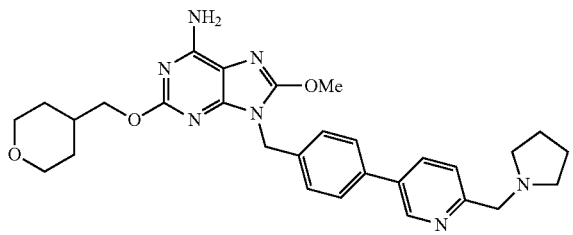

AV

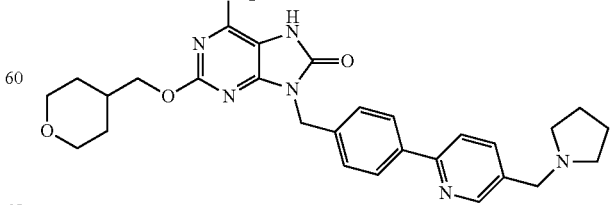

Synthesized from compound 86 according to the procedure for compound 9, using 28.

Synthesized from compound 88 according to the procedure for compound A.

AV: $^1$H-NMR: 300 MHz, (CD$_3$OD) δ: 9.11 (s, 1H), 8.75 (d, 1H, J=8 Hz), 8.40 (d, 1H, J=8 Hz), 8.04 (d, 2H, J=8 Hz), 7.71 (d, 2H, J=8 Hz), 5.20 (s, 2H), 4.70 (s, 2H), 4.41 (d, 2H, J=7 Hz), 3.94 (m, 2H), 3.66 (br m, 2H), 3.42 (t, 2H, J=11 Hz), 3.30 (br m, 2H), 2.24 (m, 2H), 2.10 (m, 2H), 1.70 (br d, 2H, J=11 Hz), 1.45 (m, 2H).

LCMS-ESI$^+$: calc'd for C$_{28}$H$_{34}$N$_7$O$_3$: 516.3 (M+H$^+$). Found: 516.1 (M+H$^+$).

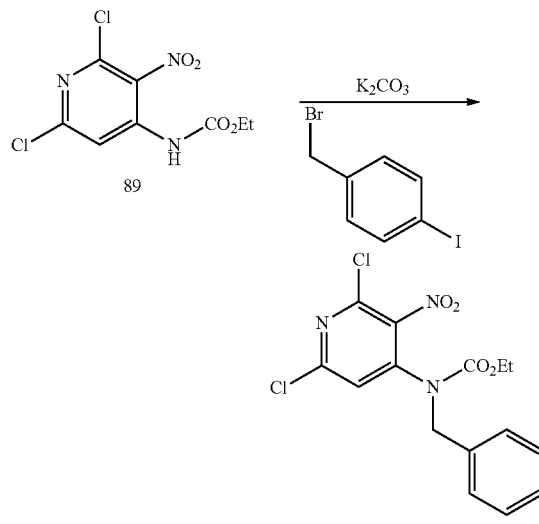

To a solution of carbamate 89 (1.40 g, 5.00 mmol) in acetonitrile (12 mL) was added potassium carbonate (1.38 g, 10.0 mmol) and 4-iodobenzyl bromide (1.56 g, 5.25 mmol). The reaction mixture was stirred at room temperature for 18 h and 45° C. for 3 h then poured onto H$_2$O (15 mL) and EtOAc (10 mL). The layers were separated, and the aqueous layer was extracted with EtOAc (10 mL). The combined organic layers were washed with brine (15 mL) then dried, filtered, and concentrated in vacuo. The crude product was purified by flash column chromatography (5-10% EtOAc/hexanes) to give 2.02 g of 90.

90: $^1$H-NMR: 300 MHz, (CDCl$_3$) δ: 7.67 (d, 2H, J=8 Hz), 7.01 (d, 2H, J=8 Hz), 6.97 (s, 1H), 4.77 (s, 2H), 4.16 (q, 2H, J=7 Hz), 1.21 (t, 3H, J=7 Hz).

LCMS-ESI$^+$: calc'd for C$_{15}$H$_{13}$Cl$_2$IN$_3$O$_4$: 497.1 (M+H$^+$). Found: 496.9 (M+H$^+$).

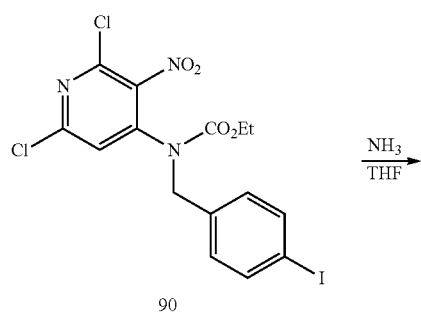

To a solution of dichloride 90 (2.02 g, 4.07 mmol) in THF (16 mL) was added a solution of NH$_3$ (4 mL, 7 M in MeOH). The reaction was stirred at room temperature for 18 h. A saturated solution of NH$_4$Cl (20 mL) was added. The layers were separated, and the aqueous layer was extracted with EtOAc (10 mL). The combined organic layers were dried, filtered, and concentrated in vacuo. The crude product was purified by flash column chromatography (EtOAc/hexanes) to give 1.53 g of 91.

91: $^1$H-NMR: 300 MHz, (DMSO) δ: 7.67 (d, 2H, J=8 Hz), 7.12 (d, 2H, J=8 Hz), 6.66 (s, 1H), 4.85 (s, 2H), 4.04 (m, 2H), 1.08 (t, 3H, J=7 Hz).

LCMS-ESI$^+$: calc'd for C$_{15}$H$_{15}$ClIN$_4$O$_4$: 477.7 (M+H$^+$). Found: 476.9 (M+H$^+$).

To a solution of 2-methoxyethanol (301 uL, 3.82 mmol) in THF (7.6 mL) was added sodium hydride (153 mg, 3.82 mmol, 60% in mineral oil). After 30 min, chloropyridine 91 (760 mg, 1.59 mmol) in THF (2 mL) was added. The reaction was stirred at room temperature for 1 h. A saturated solution of NH$_4$Cl (20 mL) was added. The layers were separated, and the aqueous layer was extracted with EtOAc (10 mL). The combined organic layers were dried, filtered, and concentrated in vacuo. The crude product was purified by flash column chromatography (EtOAc/hexanes) to give 701 mg of 92.

92: $^1$H-NMR: 300 MHz, (CDCl$_3$) δ: 7.65 (d, 2H, J=8 Hz), 7.06 (d, 2H, J=8 Hz), 6.60 (br s, 2H), 5.88 (s, 1H), 5.05 (m, 1H), 4.41 (m, 3H), 4.12 (q, 2H, J=7 Hz), 3.67 (t, 2H, J=7 Hz), 3.41 (s, 3H), 1.26 (t, 3H, J=7 Hz).

LCMS-ESI$^+$: calc'd for C$_{18}$H$_{22}$IN$_4$O$_6$: 517.3 (M+H$^+$). Found: 517.2 (M+H+).

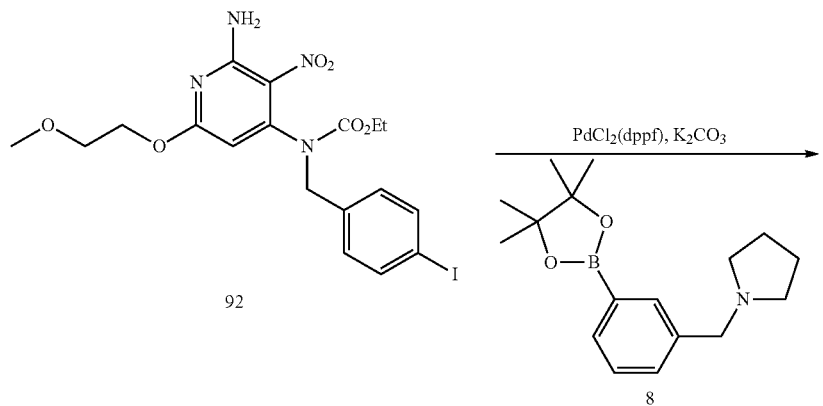
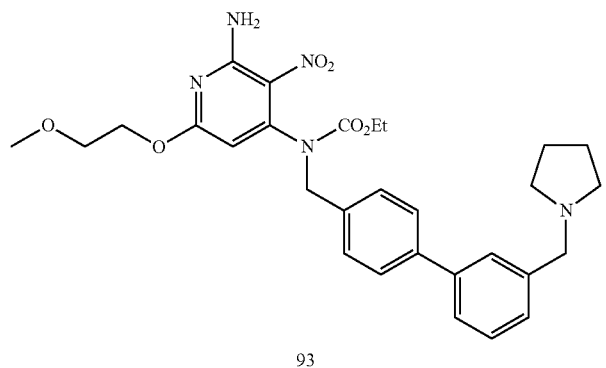
Synthesized from compound 92 according to the procedure for compound 9, using 1-(3-(4,4,5,5-tetramethyl-1,3,2-dioxaborolan-2-yl)benzyl)pyrrolidine.
93: $^1$H-NMR: 300 MHz, (CD$_3$OD) δ: 7.34-7.61 (m, 8H), 5.84 (s, 1H), 5.13 (m, 1H), 4.30-4.51 (m, 3H), 4.11 (m, 2H), 3.78 (br s, 2H), 3.65 (br m, 2H), 3.39 (s, 3H), 2.67 (br s, 4H), 1.85 (br s, 4H), 1.20 (br m, 3H).
LCMS-ESI$^+$: calc'd for C$_{29}$H$_{36}$N$_5$O$_6$: 550.6 (M+H$^+$). Found: 550.1 (M+H$^+$).
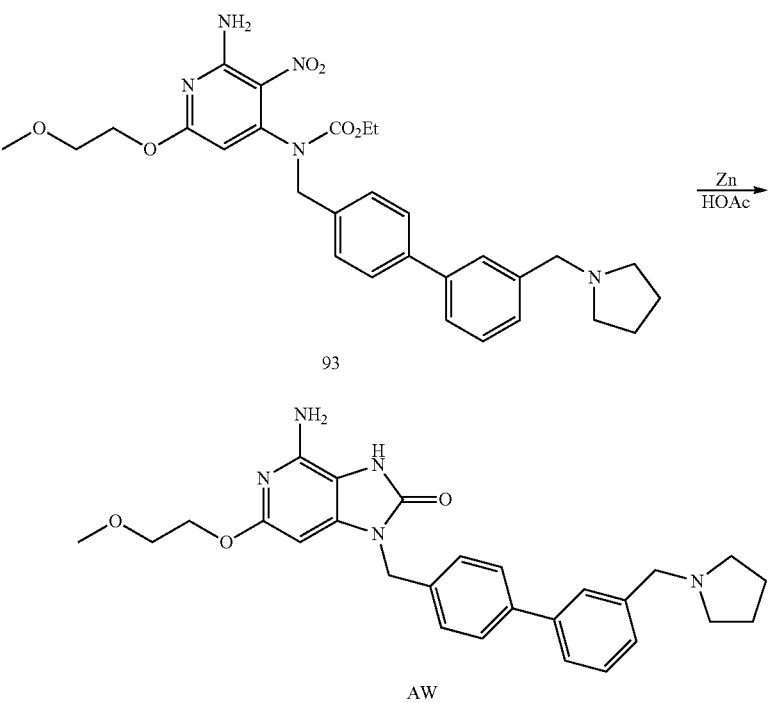

To a solution of 93 (55 mg, 0.10 mmol) in acetic acid (2 mL) was added zinc powder (65 mg). The mixture was stirred at 60° C. 1.5 h and then filtered with MeOH and concentrated in vacuo. The crude product was purified on C18 silica (MeCN/H$_2$O) to give 41 mg.

AW: $^1$H-NMR: 300 MHz, (CD$_3$OD) δ: 7.89 (s, 1H), 7.48-7.73 (m, 7H), 6.48 (s, 1H), 5.17 (s, 2H), 4.50 (s, 2H), 4.38 (m, 2H), 3.76 (m, 2H), 3.55 (br m, 2H), 3.37 (s, 3H), 3.29 (br m, 2H), 2.21 (m, 2H), 2.02 (m, 2H).

LCMS-ESI$^+$: calc'd for C$_{27}$H$_{32}$N$_5$O$_3$: 474.6 (M+H$^+$). Found: 474.1 (M+H$^+$).

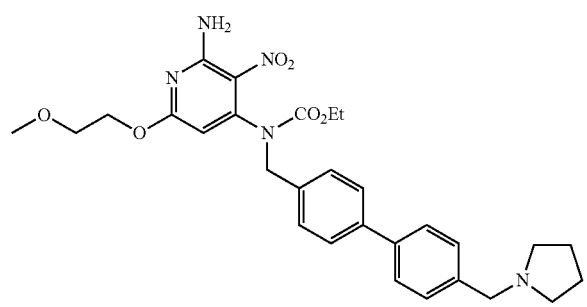

94

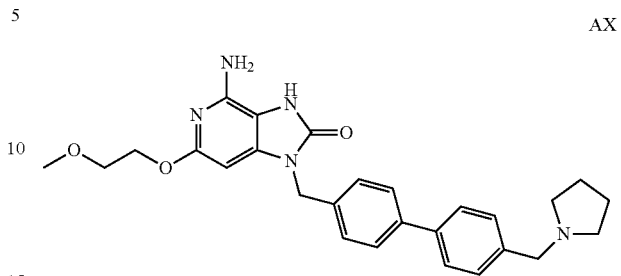

AX

Synthesized from 94 according to the procedure for compound AW.

AX: $^1$H-NMR: 300 MHz, (CD$_3$OD) δ: 7.48-7.73 (m, 8H), 6.49 (s, 1H), 5.18 (s, 2H), 4.46 (s, 2H), 4.36 (m, 2H), 3.76 (m, 2H), 3.53 (br m, 2H), 3.37 (s, 3H), 3.29 (br m, 2H), 2.22 (m, 2H), 2.02 (m, 2H).

LCMS-ESI$^+$: calc'd for C$_{27}$H$_{32}$N$_5$O$_3$: 474.6 (M+H$^+$). Found: 474.2 (M+H$^+$).

LCMS-ESI$^+$: calc'd for C$_{29}$H$_{36}$N$_5$O$_6$: 550.6 (M+H$^+$). Found: 550.1 (M+H$^+$).

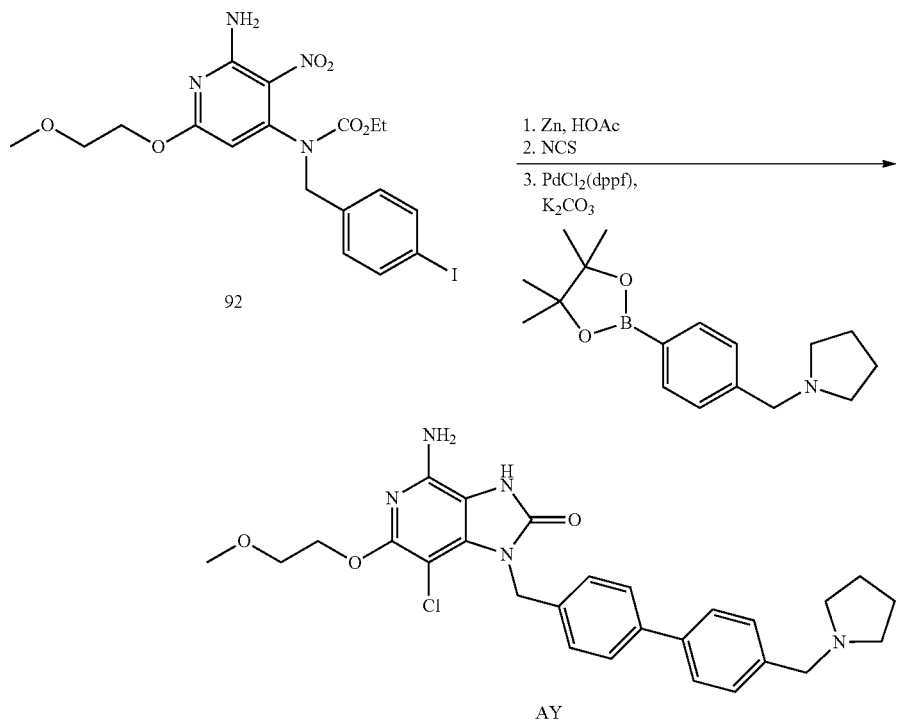

Synthesized from compound 92 according to the procedure for compound 9, using 1-(4-(4,4,5,5-tetramethyl-1,3,2-dioxaborolan-2-yl)benzyl)pyrrolidine.

94: $^1$H-NMR: 300 MHz, (CD$_3$OD) δ: 7.33-7.71 (m, 8H), 5.83 (s, 1H), 5.13 (m, 1H), 4.30-4.57 (m, 3H), 4.11 (m, 2H), 3.65-3.73 (m, 4H), 3.37 (s, 3H), 2.60 (br s, 4H), 1.83 (br s, 4H), 1.16 (br m, 3H).

To a solution of 92 (180 mg) in acetic acid (5 mL) was added zinc powder (100 mg). The mixture was stirred at 60° C. 2 h. The mixture was filtered. The solution was then diluted with H$_2$O (10 mL) and EtOAc (10 mL). The layers were separated, and the combined organic layers were washed with a saturated solution of NaHCO$_3$ (10 mL). The organic layer was dried, filtered, and concentrated in vacuo. CH$_2$Cl$_2$ (5 mL)

and acetonitrile (1 mL) were added followed by N-chlorosuccinimide (NCS) (50 mg). The reaction mixture was stirred at rt for 4 h. EtOAc (15 mL) and a saturated solution of sodium sulfite (10 mL) were added. The layers were separated, and the aqueous layer was extracted with EtOAc (10 mL). The combined organic layers were dried, filtered, and concentrated. The resulting oil was used crude in the coupling reaction according to the procedure for compound 9, using 1-(4-(4,4,5,5-tetramethyl-1,3,2-dioxaborolan-2-yl)benzyl)pyrrolidine.

AY: $^1$H-NMR: 300 MHz, (CD$_3$OD) δ: 7.70 (d, 2H, J=8 Hz), 7.62 (d, 4H, J=8 Hz), 7.34 (d, 2H, J=8 Hz), 5.46 (s, 2H), 4.49 (m, 2H), 4.43 (s, 2H), 3.75 (m, 2H), 3.52 (br m, 2H), 3.38 (s, 3H), 3.22 (br m, 2H), 2.19 (m, 2H), 2.04 (m, 2H).

LCMS-ESI$^+$: calc'd for C$_{27}$H$_{31}$ClN$_5$O$_3$: 508.0 (M+H$^+$). Found: 508.1 (M+H$^+$).

95

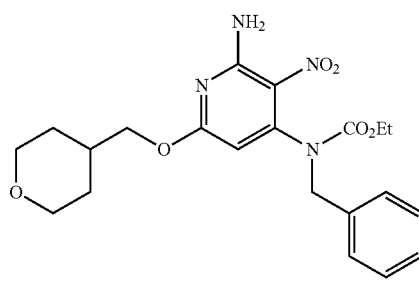

Synthesized from compound 91 according to the procedure for 92, using 4-tetrahydropyranmethanol.

95: $^1$H-NMR: 300 MHz, (CDCl$_3$) δ: 7.65 (d, 2H, J=8 Hz), 7.07 (d, 2H, J=8 Hz), 6.62 (br s, 2H), 5.77 (s, 1H), 5.10 (m, 1H), 4.42 (m, 1H), 3.98-4.16 (m, 6H), 3.42 (t, 2H, J=11 Hz), 2.00 (m, 1H), 1.65 (m, 2H), 1.42 (m, 2H), 1.28 (t, 3H, J=7 Hz).

LCMS-ESI$^+$: calc'd for C$_{21}$H$_{26}$IN$_4$O$_6$: 557.4 (M+H$^+$). Found: 557.2 (M+H$^+$).

96

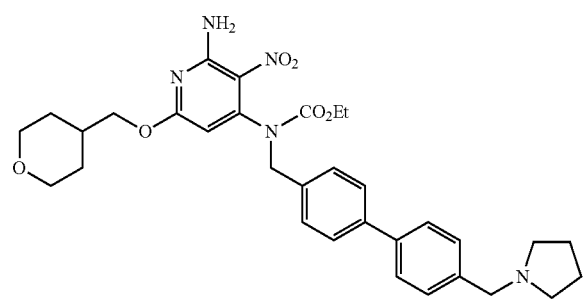

Synthesized from compound 95 according to the procedure for compound 9, using 1-(4-(4,4,5,5-tetramethyl-1,3,2-dioxaborolan-2-yl)benzyl)pyrrolidine.

96: $^1$H-NMR: 300 MHz, (CDCl$_3$) δ: 7.50-7.57 (m, 4H), 7.33-7.42 (m, 4H), 6.64 (br s, 2H), 5.82 (s, 1H), 5.24 (br m, 1H), 4.47 (br m, 1H), 4.06-4.24 (m, 6H), 3.96 (m, 2H), 3.68 (s, 2H), 3.38 (t, 2H, J=11 Hz), 2.56 (m, 4H), 1.99 (m, 1H), 1.66 (m, 4H), 1.15-1.42 (m, 7H).

LCMS-ESI$^+$: calc'd for C$_{32}$H$_{40}$N$_5$O$_6$: 590.7 (M+H$^+$). Found: 590.1 (M+H$^+$).

AZ

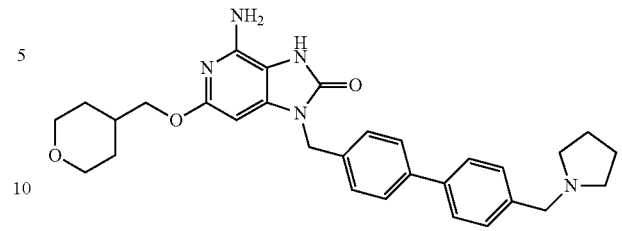

Synthesized from compound 96 according to the procedure for compound AW.

AZ: $^1$H-NMR: 300 MHz, (CD$_3$OD) δ: 7.73 (d, 2H, J=8 Hz), 7.65 (m, 4H), 7.47 (d, 2H, J=8 Hz), 6.44 (s, 1H), 5.18 (s, 2H), 4.91 (s, 2H), 4.08 (d, 2H, J=6 Hz), 3.95 (dd, 2H, J=11, 4 Hz), 3.53 (m, 2H), 3.40 (t, 2H, J=11 Hz), 3.22 (m, 2H), 2.02-2.21 (m, 5H), 1.72 (d, 2H, J=11 Hz), 1.47 (m, 2H).

LCMS-ESI$^+$: calc'd for C$_{30}$H$_{36}$N$_5$O$_3$: 514.6 (M+H$^+$). Found: 514.1 (M+H$^+$).

97

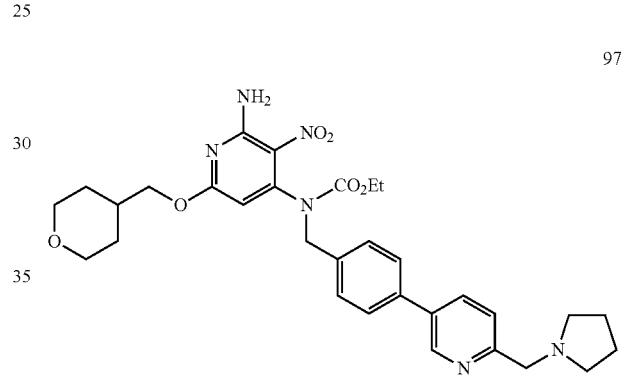

Synthesized from compound 95 according to the procedure for compound 9, using 28.

97: $^1$H-NMR: 300 MHz, (CDCl$_3$) δ: 8.79 (s, 1H), 7.85 (d, 2H, J=8 Hz), 7.44-7.57 (m, 4H), 7.33-7.42 (m, 4H), 6.62 (br s, 2H), 5.86 (s, 1H), 5.20 (br m, 1H), 4.56 (br m, 1H), 3.96-4.24 (m, 6H), 3.85 (s, 2H), 3.39 (t, 2H, J=11 Hz), 2.64 (m, 4H), 1.99 (m, 1H), 1.84 (m, 4H), 1.65 (m, 2H), 1.41 (m, 2H).

LCMS-ESI$^+$: calc'd for C$_{31}$H$_{39}$N$_6$O$_6$: 591.7 (M+H$^+$). Found: 591.1 (M+H$^+$).

BA

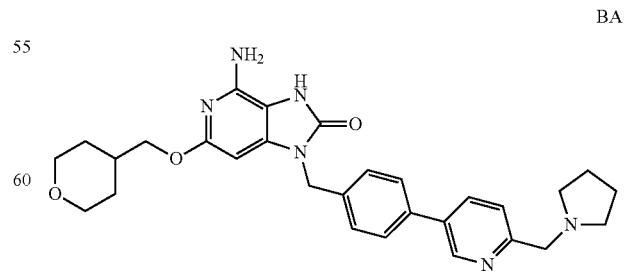

Synthesized from compound 97 according to the procedure for compound AW.

BA: LCMS-ESI+: calc'd for $C_{29}H_{35}N_6O_3$: 515.7 (M+H+).
Found: 515.2 (M+H+).

98

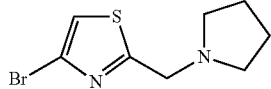

Synthesized from 4-bromothiazole-2-carbaldehyde according to the procedure for compound 28.

LCMS-ESI+: calc'd for $C_8H_{12}BrN_2S$: 248.2 (M+H+). Found: 246.9 (M+H+).

99

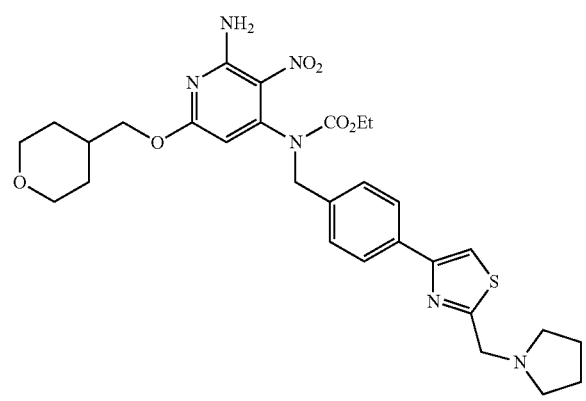

Synthesized from compound 95 according to the procedure for compound 9, using 28.

98: $^1$H-NMR: 300 MHz, (CDCl$_3$) δ: 7.84 (d, 2H, J=8 Hz), 7.46 (s, 1H), 7.36 (d, 2H, J=8 Hz), 6.61 (br s, 2H), 5.80 (s, 1H), 5.20 (br m, 1H), 4.52 (br m, 1H), 3.97-4.22 (m, 8H), 3.39 (t, 2H, J=11 Hz), 2.78 (m, 4H), 1.99 (m, 1H), 1.89 (m, 4H), 1.62 (m, 2H), 1.40 (m, 2H).

LCMS-ESI+: calc'd for $C_{29}H_{37}N_6O_6S$: 597.7 (M+H+). Found: 597.2 (M+H+).

BB

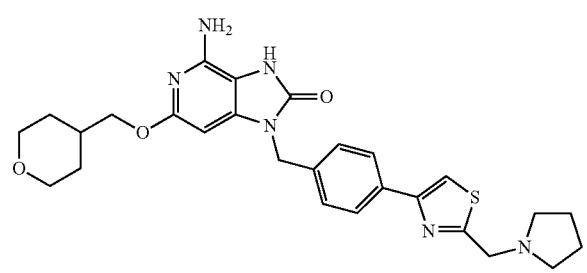

Synthesized from compound 99 according to the procedure for compound AW.

LCMS-ESI+: calc'd for $C_{27}H_{33}N_6O_3S$: 521.7 (M+H+). Found: 521.1 (M+H+).

100

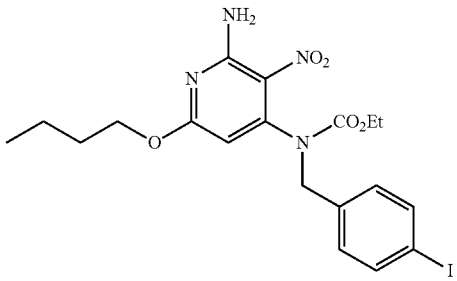

Synthesized from compound 91 according to the procedure for 92, using 1-butanol.

100: $^1$H-NMR: 300 MHz, (CDCl$_3$) δ: 7.

LCMS-ESI+: calc'd for $C_{19}H_{24}IN_4O_5$: 515.3 (M+H+). Found: 515.1 (M+H+).

101

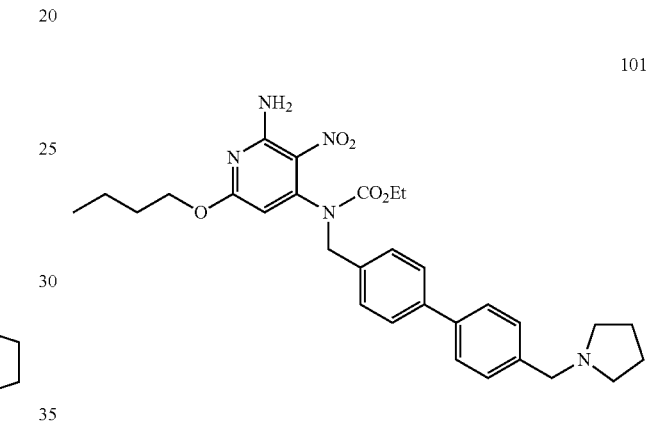

Synthesized from compound 100 according to the procedure for compound 9, using 1-(4-(4,4,5,5-tetramethyl-1,3,2-dioxaborolan-2-yl)benzyl)pyrrolidine.

101: $^1$H-NMR: 300 MHz, (CDCl$_3$) δ: 7.56 (m, 4H), 7.40 (m, 4H), 6.12 (br s, 2H), 5.84 (s, 1H), 4.47 (m, 1H), 4.22 (m, 2H), 4.12 (m, 1H), 3.68 (s, 2H), 2.57 (m, 4H), 1.82 (m, 4H), 1.67 (m, 2H), 1.42 (m, 2H), 1.19 (m, 3H), 0.94 (t, 3H, J=7 Hz).

LCMS-ESI+: calc'd for $C_{30}H_{38}N_5O_5$: 548.7 (M+H+). Found: 548.1 (M+H+).

BC

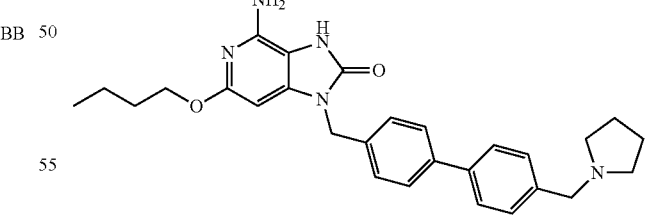

Synthesized from compound 101 according to the procedure for compound AW.

BC: $^1$H-NMR: 300 MHz, (CDCl$_3$) δ: 7.43 (d, 2H, J=8 Hz), 7.67 (d, 2H, J=8 Hz), 7.62 (d, 2H, J=8 Hz), 7.48 (d, 2H, J=8 Hz), 6.42 (s, 1H), 5.18 (s, 2H), 4.43 (d, 2H), 4.22 (t, 2H, J=7 Hz), 3.53 (m, 2H), 3.24 (m, 2H), 2.20 (m, 2H), 2.06 (m, 2H), 1.80 (m, 2H), 1.52 (m, 2H), 0.98 (t, 3H, J=7 Hz).

LCMS-ESI+: calc'd for $C_{28}H_{34}N_5O_2$: 472.6 (M+H+). Found: 472.1 (M+H+).

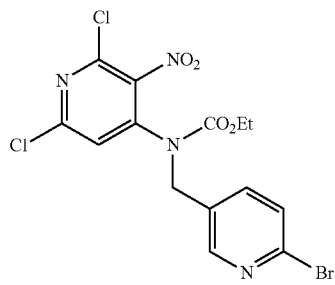

102

Synthesized from compound 89 according to the procedure for compound 90, using 2-bromo-5-(bromomethyl)pyridine.

102: $^1$H-NMR: 300 MHz, (CDCl$_3$) δ: 8.27 (s, 1H), 7.54 (m, 2H), 7.06 (s, 1H), 4.81 (s, 2H), 4.18 (q, 2H, J=7 Hz), 1.23 (t, 3H, J=7 Hz).

LCMS-ESI$^+$: calc'd for C$_{14}$H$_{12}$BrCl$_2$N$_4$O$_4$: 451.1 (M+H$^+$). Found: 450.9 (M+H$^+$).

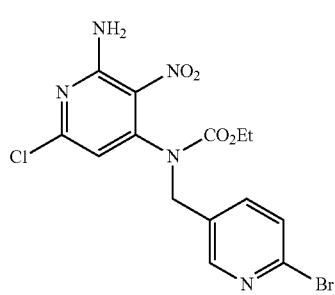

103

Synthesized from compound 102 according to the procedure for compound 91.

103: $^1$H-NMR: 300 MHz, (CDCl$_3$) δ: 8.30 (s, 1H), 7.63 (m, 1H), 7.48 (m, 1H), 6.45 (s, 1H), 6.41 (br s, 2H), 4.87 (s, 2H), 4.14 (q, 2H, J=7 Hz), 1.26 (t, 3H, J=7 Hz).

LCMS-ESI$^+$: calc'd for C$_{14}$H$_{14}$BrClN$_5$O$_4$: 431.6 (M+H$^+$). Found: 431.9 (M+H$^+$).

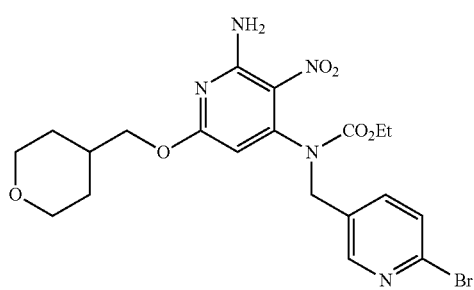

104

Synthesized from compound 103 according to the procedure for compound 92, using 4-tetrahydropyranmethanol.

104: $^1$H-NMR: 300 MHz, (CDCl$_3$) δ: 8.25 (s, 1H), 7.70 (m, 1H), 7.48 (d, 1H, J=8 Hz), 6.67 (br s, 2H), 5.80 (s, 1H), 4.97 (m, 1H), 4.60 (m, 1H), 3.97-4.18 (m, 4H), 3.37-3.50 (m, 4H), 2.02 (m, 1H), 1.72 (m, 2H), 1.35 (m, 2H), 1.15 (t, 3H, J=7 Hz).

LCMS-ESI$^+$: calc'd for C$_{20}$H$_{25}$BrN$_5$O$_6$: 511.3 (M+H$^+$). Found: 510.1 (M+H$^+$).

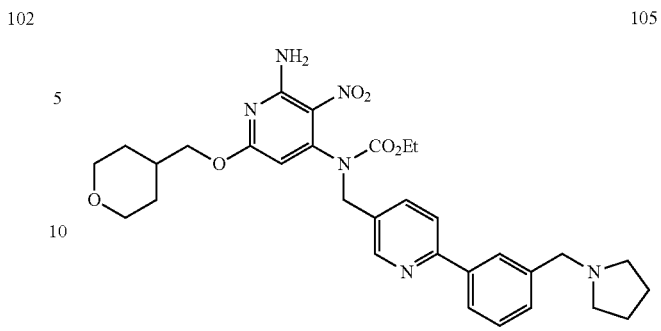

105

Synthesized from compound 104 according to the procedure for compound 9, using 1-(3-(4,4,5,5-tetramethyl-1,3,2-dioxaborolan-2-yl)benzyl)pyrrolidine.

105: $^1$H-NMR: 300 MHz, (CDCl$_3$) δ: 8.55 (s, 1H), 7.17-7.95 (m, 6H), 6.65 (br s, 2H), 5.85 (s, 1H), 5.01 (m, 1H), 4.66 (m, 1H), 3.97-4.21 (m, 6H), 3.37-3.70 (m, 4H), 2.56 (m, 4H), 2.02 (m, 1H), 1.80 (m, 4H), 1.68 (m, 2H), 1.35 (m, 2H), 1.17 (br m, 3H).

LCMS-ESI$^+$: calc'd for C$_{31}$H$_{39}$N$_6$O$_6$: 591.7 (M+H$^+$). Found: 591.2 (M+H$^+$).

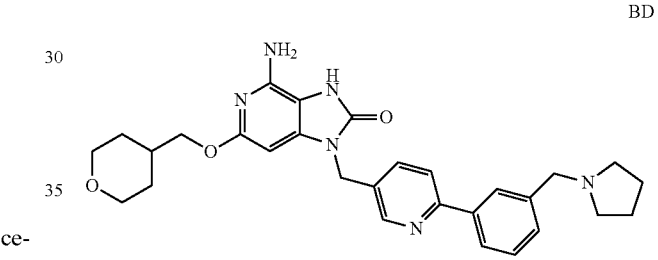

BD

Synthesized from 105 according to the procedure for compound AW.

BD: $^1$H-NMR: 300 MHz, (CD$_3$OD) δ: 8.94 (s, 1H), 8.46 (d, 1H, J=8 Hz), 8.30 (m, 2H), 8.07 (d, 1H, J=8 Hz), 7.79 (m, 2H), 6.73 (s, 1H), 5.37 (s, 2H), 4.54 (s, 2H), 4.16 (d, 2H, J=7 Hz), 3.99 (m, 2H), 3.53 (m, 4H), 3.29 (m, 2H), 2.21 (m, 2H), 2.06 (m, 2H), 1.77 (m, 2H), 1.48 (m, 2H).

LCMS-ESI$^+$: calc'd for C$_{29}$H$_{35}$N$_6$O$_3$: 515.6 (M+H$^+$). Found: 515.1 (M+H$^+$).

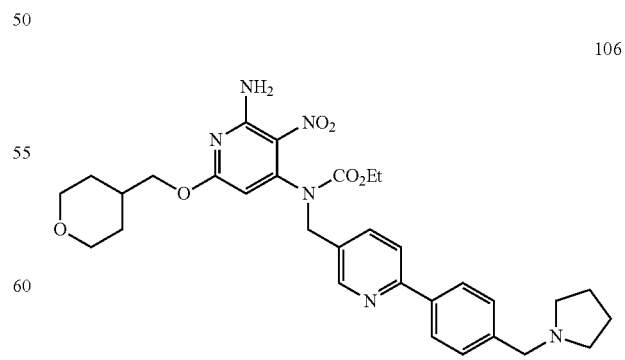

106

Synthesized from compound 104 according to the procedure for compound 9, using 1-(4-(4,4,5,5-tetramethyl-1,3,2-dioxaborolan-2-yl)benzyl)pyrrolidine.

106: ¹H-NMR: 300 MHz, (CDCl₃) δ: 8.54 (s, 1H), 7.94 (d, 2H, J=8 Hz), 7.75 (m, 1H), 7.45 (d, 2H, J=8 Hz), 7.19 (m, 1H), 6.65 (br s, 2H), 5.85 (s, 1H), 5.11 (m, 1H), 4.66 (m, 1H), 3.97-4.22 (m, 6H), 3.51 (m, 2H), 3.40 (m, 2H), 2.55 (m, 4H), 2.00 (m, 1H), 1.81 (m, 4H), 1.67 (m, 2H), 1.35 (m, 2H), 1.17 (br m, 3H).

LCMS-ESI⁺: calc'd for $C_{31}H_{39}N_6O_6$: 591.7 (M+H⁺). Found: 591.1 (M+H⁺).

BE

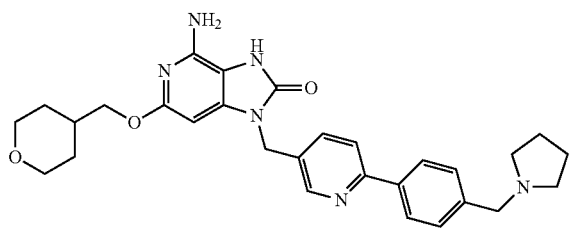

Synthesized from 106 according to the procedure for compound AW.

BE: ¹H-NMR: 300 MHz, (CD₃OD) δ: 9.03 (s, 1H), 8.70 (d, 1H, J=8 Hz), 8.42 (d, 1H, J=8 Hz), 8.10 (d, 2H, J=8 Hz), 7.90 (d, 2H, J=8 Hz), 6.82 (s, 1H), 5.44 (s, 2H), 4.55 (s, 2H), 4.18 (d, 2H, J=7 Hz), 3.99 (m, 2H), 3.54 (m, 2H), 3.44 (m, 2H), 3.27 (m, 2H), 2.22 (m, 2H), 2.06 (m, 2H), 1.78 (m, 2H), 1.49 (m, 2H).

LCMS-ESI⁺: calc'd for $C_{29}H_{35}N_6O_3$: 515.6 (M+H⁺). Found: 515.1 (M+H⁺).

107

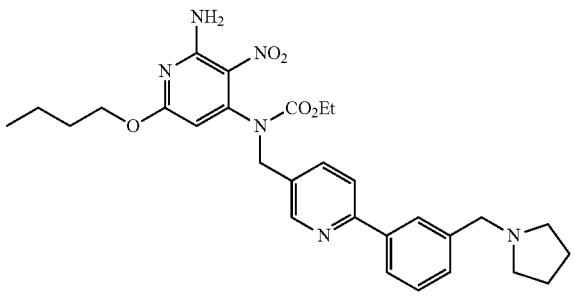

Synthesized from compound 103 according to the procedure for compound 92, using 1-butanol.

107: ¹H-NMR: 300 MHz, (CDCl₃) δ: 8.26 (s, 1H), 7.68 (m, 1H), 7.47 (d, 1H, J=8 Hz), 6.67 (br s, 2H), 5.80 (s, 1H), 4.98 (m, 1H), 4.59 (m, 1H), 4.08-4.28 (m, 4H), 1.72 (m, 2H), 1.42 (m, 2H), 1.15 (m, 3H), 0.97 (t, 3H, J=7 Hz).

LCMS-ESI⁺: calc'd for $C_{18}H_{23}BrN_5O_5$: 469.3 (M+H⁺). Found: 468.1 (M+H⁺).

108

Synthesized from compound 107 according to the procedure for compound 9, using 1-(3-(4,4,5,5-tetramethyl-1,3,2-dioxaborolan-2-yl)benzyl)pyrrolidine.

108: ¹H-NMR: 300 MHz, (CDCl₃) δ: 8.56 (s, 1H), 7.19-7.95 (m, 6H), 6.65 (br s, 2H), 5.85 (s, 1H), 5.11 (m, 1H), 4.65 (m, 1H), 4.23 (m, 4H), 3.72 (s, 2H), 2.57 (m, 4H), 1.80 (m, 4H), 1.67 (m, 2H), 1.40 (m, 2H), 1.17 (br m, 3H), 0.95 (t, 3H, J=7 Hz).

LCMS-ESI⁺: calc'd for $C_{29}H_{37}N_6O_5$: 549.6 (M+H⁺). Found: 549.1 (M+H⁺).

BF

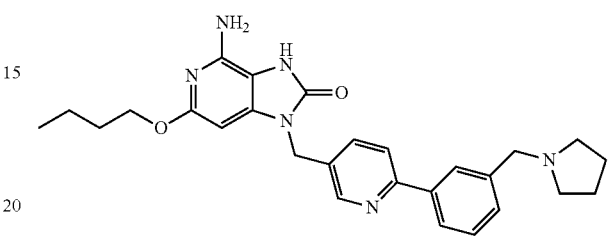

Synthesized from 108 according to the procedure for compound AW.

BF: ¹H-NMR: 300 MHz, (CD₃OD) δ: 8.99 (s, 1H), 8.61 (d, 1H, J=8 Hz), 8.42 (d, 1H, J=8 Hz), 8.29 (s, 1H), 8.07 (d, 1H, J=8 Hz), 7.86 (d, 1H, J=8 Hz), 7.78 (t, 1H, J=8 Hz), 6.76 (s, 1H), 5.42 (s, 2H), 4.56 (s, 2H), 4.31 (t, 2H, J=7 Hz), 3.60 (m, 2H), 3.28 (m, 2H), 2.22 (m, 2H), 2.07 (m, 2H), 1.86 (m, 2H), 1.56 (m, 2H), 1.01 (t, 3H, J=7 Hz).

LCMS-ESI⁺: calc'd for $C_2H_{33}N_6O_2$: 473.6 (M+H⁺). Found: 473.1 (M+H⁺).

109

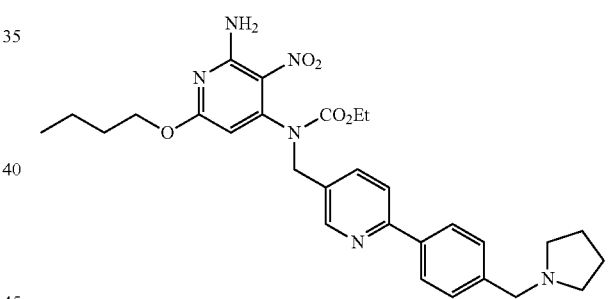

Synthesized from compound 107 according to the procedure for compound 9, using 1-(4-(4,4,5,5-tetramethyl-1,3,2-dioxaborolan-2-yl)benzyl)pyrrolidine.

109: ¹H-NMR: 300 MHz, (CDCl₃) δ: 8.55 (s, 1H), 7.18-7.96 (m, 6H), 6.65 (br s, 2H), 5.85 (s, 1H), 5.12 (m, 1H), 4.63 (m, 1H), 4.23 (m, 2H), 4.12 (q, 2H, J=7 Hz), 3.69 (s, 2H), 2.55 (m, 4H), 1.81 (m, 4H), 1.68 (m, 2H), 1.41 (m, 2H), 1.17 (br m, 3H), 0.95 (t, 3H, J=7 Hz).

LCMS-ESI⁺: calc'd for $C_{29}H_{37}N_6O_5$: 549.6 (M+H⁺). Found: 549.1 (M+H⁺).

BG

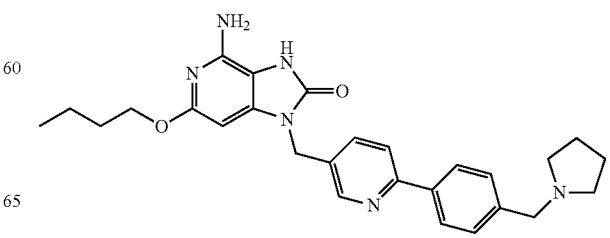

Synthesized from 109 according to the procedure for compound AW.

BG: $^1$H-NMR: 300 MHz, (CD$_3$OD) δ: 8.99 (s, 1H), 8.61 (d, 1H, J=8 Hz), 8.37 (d, 1H, J=8 Hz), 8.10 (d, 2H, J=8 Hz), 7.87 (d, 2H, J=8 Hz), 6.77 (s, 1H), 5.42 (s, 2H), 4.54 (s, 2H), 4.31 (t, 2H, J=7 Hz), 3.56 (m, 2H), 3.27 (m, 2H), 2.22 (m, 2H), 2.06 (m, 2H), 1.86 (m, 2H), 1.56 (m, 2H), 1.01 (t, 3H, J=7 Hz).

LCMS-ESI$^+$: calc'd for C$_{27}$H$_{33}$N$_6$O$_2$: 473.6 (M+H$^+$). Found: 473.1 (M+H$^+$).

BIOLOGICAL EXAMPLES

PBMC Assay Protocol

Assays were conducted to determine cytokine stimulation at 24 hours from human Peripheral Blood Mononuclear Cell (PMBC) using the compounds of the present invention. The assays were run in duplicate, with 8-point, half-log dilution curves. The compounds of the present invention were diluted from 10 mM DMSO solution. Cell supernatants are assayed directly for IFNα and 1:10 dilution for TNFα. The assays were performed in a similar fashion as described in Bioorg. Med. Chem. Lett. 16, 4559, (2006). Specifically, cryo-preserved PBMCs were thawed and seeded 96 well plates with 750,000 cells/well in 190 μL/well cell media. The PBMCs were then incubated for 1 hour at 37° C. at 5% CO2. Then, the compounds of the present invention were added in 10 μL cell media at 8 point, half-log dilution titration. The plates were incubated at 37° C. and 5% CO2 for 24 hours and then spinned at 1200 rpm for 10 min, which was followed by collecting supernatant and storing the same at −80° C. Cytokine secretion was assayed with Luminex and Upstate multiplex kits, using a Luminex analysis instrument. IFN MEC value for a compound was the minimum concentration at which IFN-α production stimulated by the compound reached three fold above background, as determined using the assay method above.

The compounds of the present invention have IFN MEC values (nM) in the range of about 0.1 to about 10,000, or about 0.1 to about 1,000, or about 0.1 to about 300, or about 0.1 to about 100, or about 0.1 to about 10, or about 0.1 to about 5, or about 0.1 to about 1, or less than about 5000, or less than about 3000, or less than about 1000, or less than about 500, or less than about 400, or less than about 300, or less than about 200, or less than about 100, or less than about 50, or less than about 20, or less than about 10, or less than about 5, or less than about 1.

In one embodiment, the compounds of the present invention have IFN ECmax values (nM) of ≤1000 nM. Table 1 shows IFN MEC values for the compounds disclosed in Examples A-I of the present application.

TABLE 1

| Example | MEC |
|---|---|
| A | d |
| B | c |
| C | b |
| D | a |
| E | a |
| F | a |
| G | a |
| H | a |
| I | a |
| J | a |
| K | a |
| L | a |
| M | a |

TABLE 1-continued

| Example | MEC |
|---|---|
| N | a |
| O | a |
| P | a |
| Q | a |
| R | a |
| S | a |
| T | a |
| U | a |
| V | a |
| W | a |
| X | a |
| Y | b |
| Z | a |
| AA | d |
| AB | d |
| AC | a |
| AD | a |
| AE | a |
| AF | a |
| AG | a |
| AH | a |
| AI | a |
| AJ | a |
| AK | a |
| AL | a |
| AM | c |
| AN | a |
| AO | a |
| AP | a |
| AQ | a |
| AR | a |
| AS | a |
| AT | a |
| AU | a |
| AV | a |
| AW | b |
| AX | b |
| AY | c |
| AZ | a |
| BA | a |
| BB | b |
| BC | a |
| BD | a |
| BE | a |
| BF | a |
| BG | a |

MEC = minimum concentration for induction of IFN-alpha ≥3-fold over background
a: ≤1 nM
b: 1 nM-9 nM
c: 10 nM-99 nM
d: 100 nM-1000 nM
e: ≥1000 nM The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

We claim:

1. A method for treating a viral infection selected from the group consisting of HBV and HCV, comprising administering a compound of Formula I:

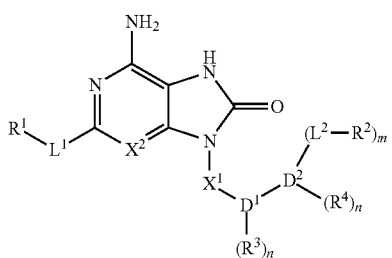

or a pharmaceutically acceptable salt thereof, wherein:
$L^1$ is —O—;
$R^1$ is H, $C_{1-6}$ alkyl, $C_{1-6}$ heteroalkyl, or $C_{4-20}$ heterocyclylalkyl, wherein each heteroalkyl group includes 1 or 2 heteroatoms selected from O, N, or S, and wherein each heterocyclyl group includes 1 to 6 heteroatoms selected from O, N, or S;
$X^2$ is N or C—$R^5$;
$R^5$ is H, halogen, or $C_{1-6}$ alkyl;
$X^1$ is $C_{1-6}$ alkylene;
$D^1$ is phenyl, pyridinyl or thiazolyl;
$D^2$ is phenyl, pyridinyl or thiazolyl;
each $L^2$ is independently $C_{1-6}$ alkylene;
each $R^2$ is independently —$NR^6R^7$;
m is 1;
each $R^3$ and $R^4$ is independently halogen, $C_{1-6}$ haloalkyl, —$OR^8$, or —CN;
each n is independently 0, 1, 2, 3, or 4, depending on the size of the depicted ring $D^1$ and $D^2$, such that sufficient attachment points are present for each $R^3$ and $R^4$;
$R^6$ and $R^7$ are each independently H, or $C_{1-6}$ alkyl; or
$R^6$ and $R^7$, taken together with the nitrogen to which they are both attached, form a substituted or unsubstituted 3 to 8 membered heterocycle, which may contain one or more additional heteroatoms selected from N, O, S, or P, wherein the substituted heterocycle is substituted with $C_{1-6}$ alkyl; or
$R^7$ taken together with $L^2$, and the N to which they are both attached, forms a substituted or unsubstituted 3 to 8 membered heterocycle which may contain one or more additional heteroatoms selected from N, O, S, or P, wherein the substituted heterocycle is substituted with $C_{1-6}$ alkyl; or
$R^7$ taken together with $D^2$, $L^2$, and the N to which both $R^7$ and $L^2$ are attached forms a substituted or unsubstituted 5 to 15 membered heterocycle or heteroaryl which may contain one or more additional heteroatoms selected from N, O, S, or P, wherein the substituted heterocycle is substituted with $C_{1-6}$ alkyl; and
$R^8$ is H, or $C_{1-6}$ alkyl.

2. The method of claim 1, wherein the viral infection is HBV.

3. The method of claim 1, wherein:
n is 0, 1, or 2.

4. The method of claim 1, wherein:
$R^6$ and $R^7$ together with the nitrogen to which they are attached form a substituted or unsubstituted 3 to 8 membered heterocyclyl, which may contain one or more additional heteroatoms selected from N, O, S, or P, wherein the substituted heterocycle is substituted with $C_{1-6}$ alkyl.

5. The method of claim 1, wherein:
$R^6$ is H, or $C_{1-6}$ alkyl; and
$R^7$ taken together with $D^2$, $L^2$, and the N to which both $R^7$ and $L^2$ are attached forms a substituted or unsubstituted 5 to 15 membered heterocycle or heteroaryl which may contain one or more additional heteroatoms selected from N, O, S, or P, wherein the substituted heterocycle is substituted with $C_{1-6}$ alkyl.

6. The method of claim 1, wherein $X^2$ is N.
7. The method of claim 1, wherein $X^2$ is C—$R^5$.
8. The method of claim 1, wherein $X^1$ is $C_{1-6}$ alkylene.
9. The method of claim 1, wherein $D^1$ is phenyl.
10. The method of claim 1, wherein $D^2$ is phenyl.
11. The method of claim 1, wherein the compound is selected from the group consisting of:

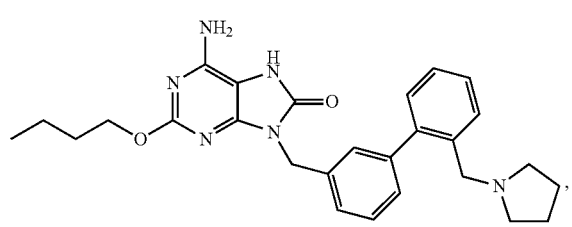

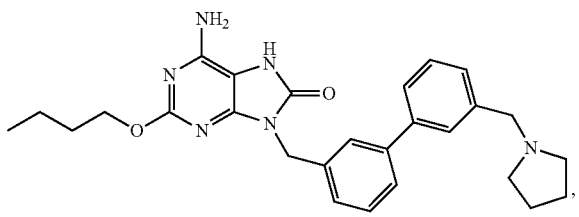

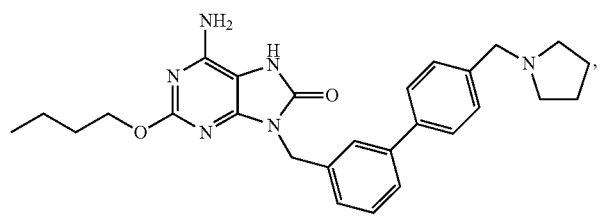

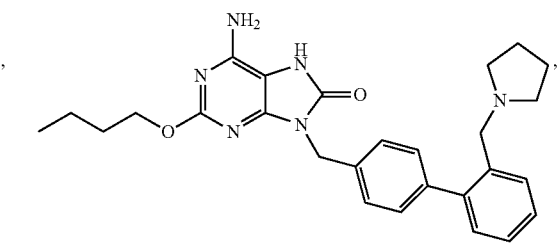

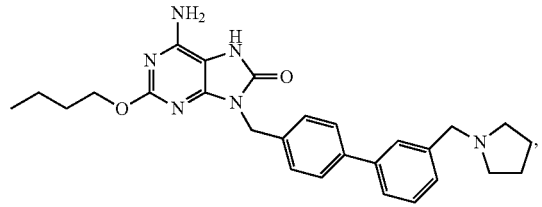

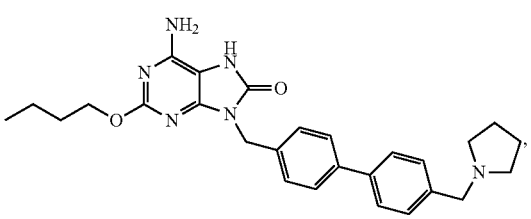

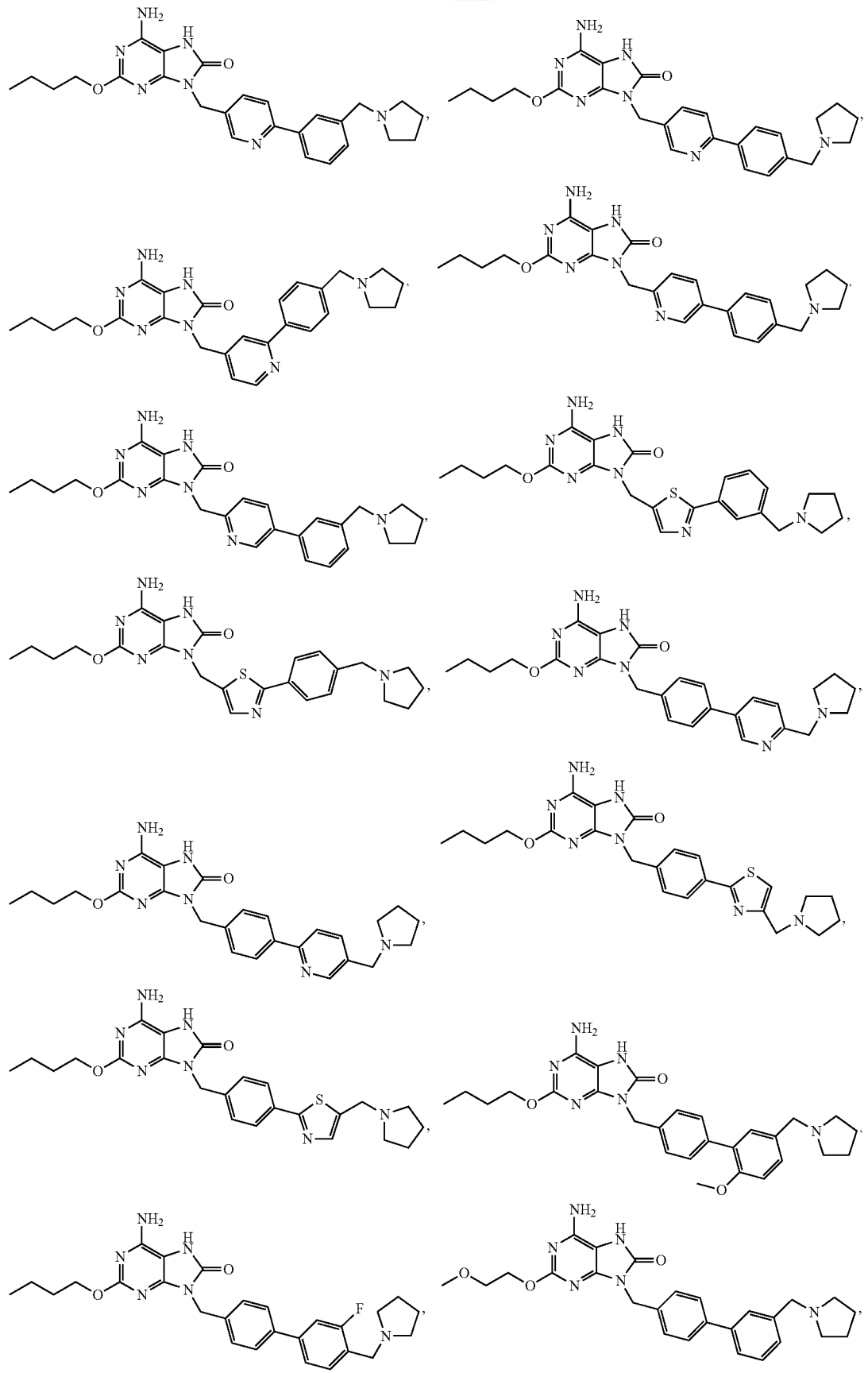

-continued
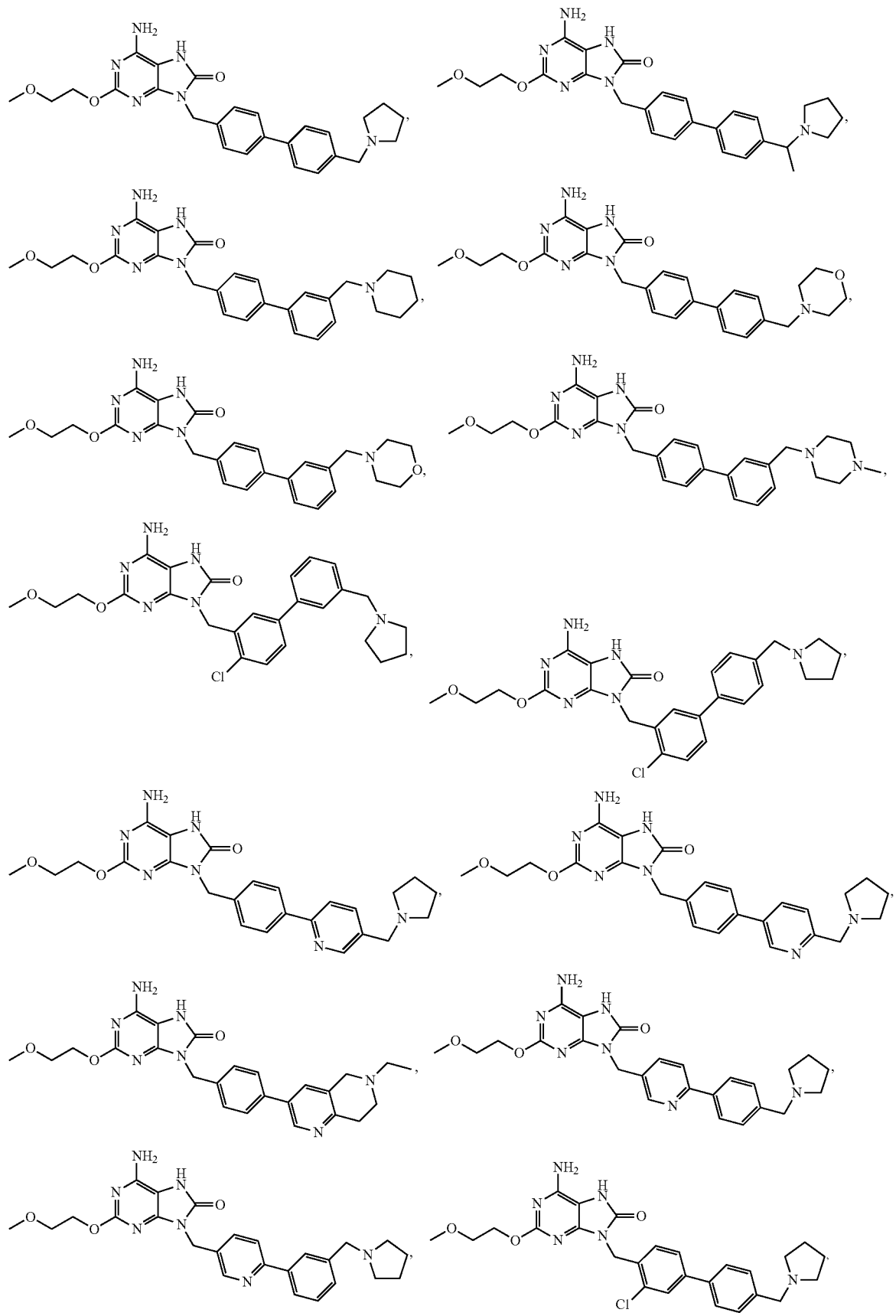

-continued
103
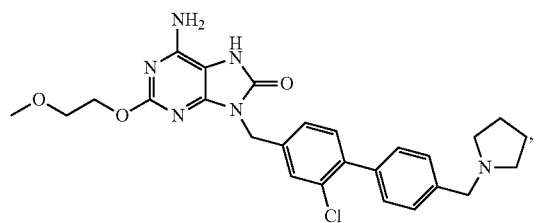
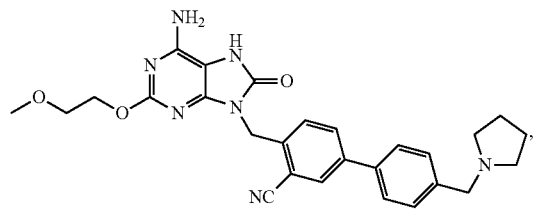
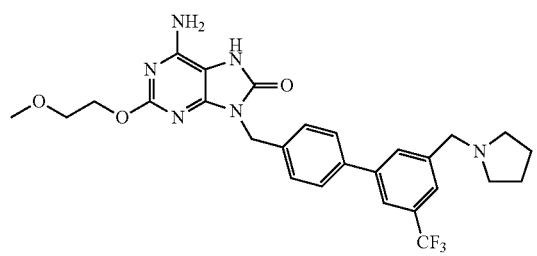
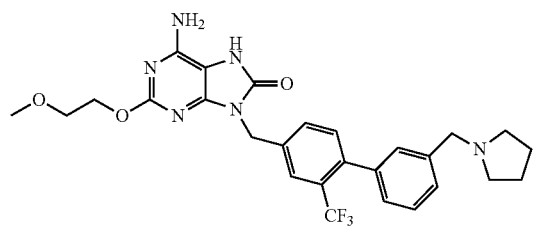
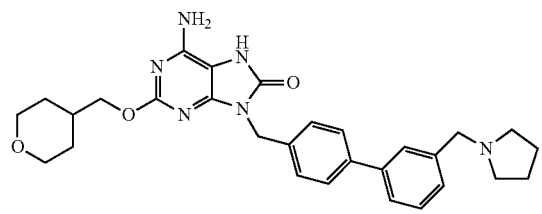
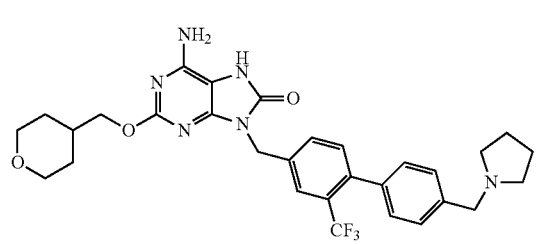
104
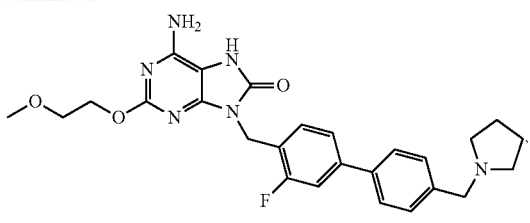
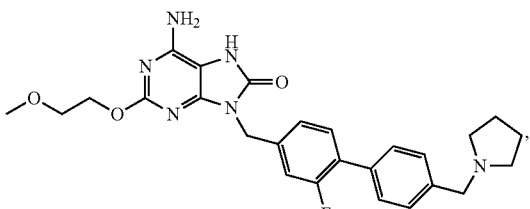
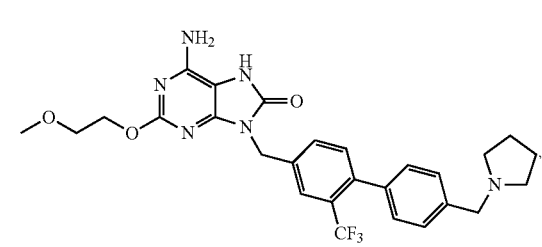
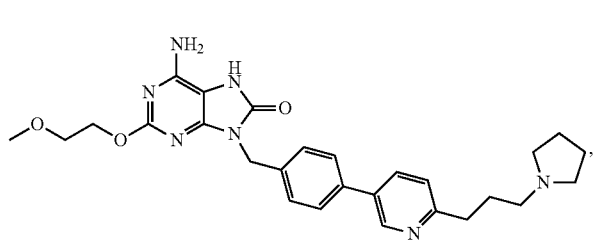
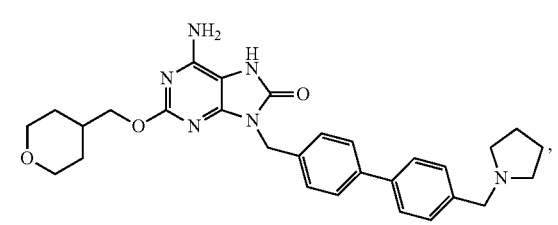
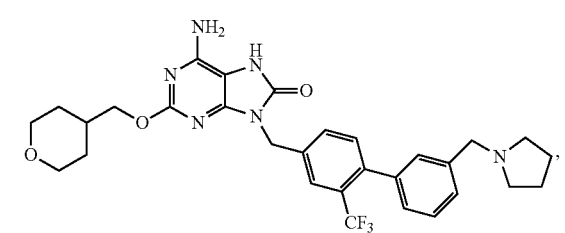

-continued
105
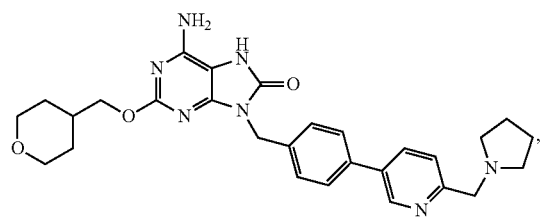
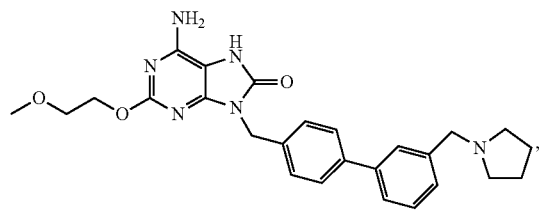
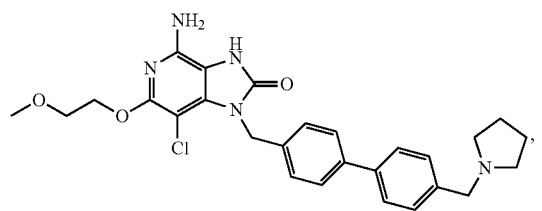
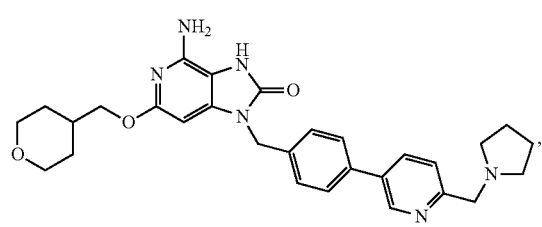
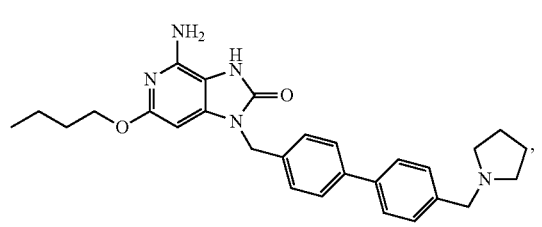
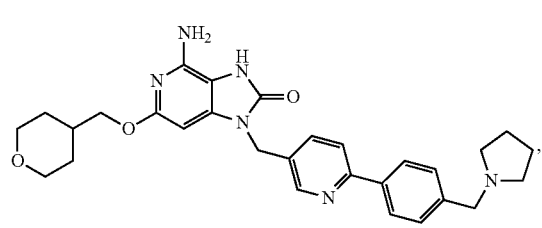
106
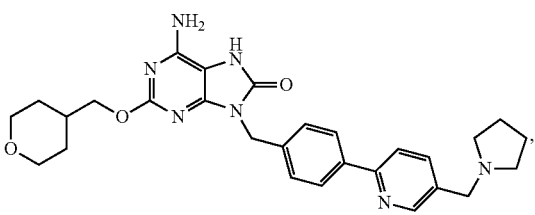
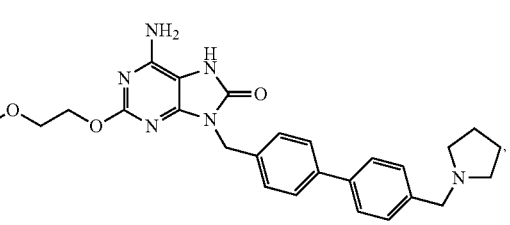
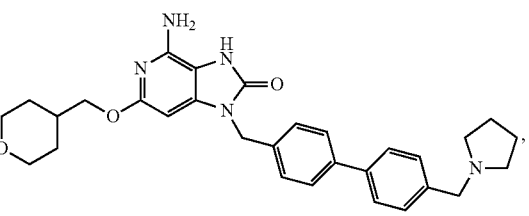
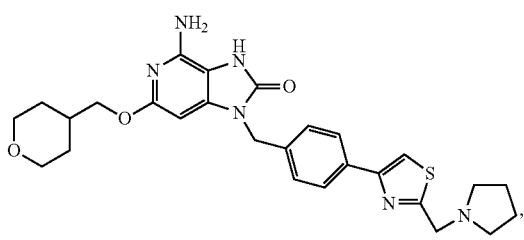
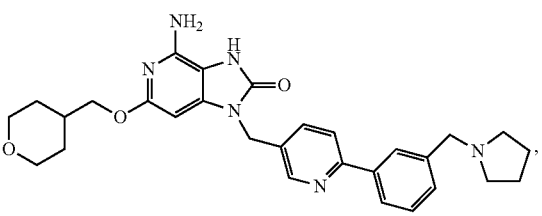
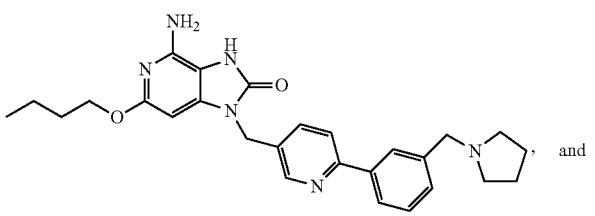, and

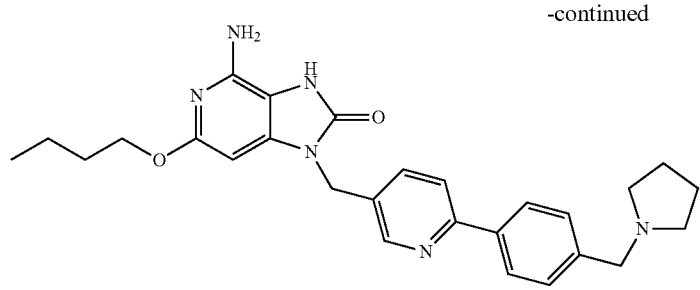
or a pharmaceutically acceptable salt thereof.
12. The method of claim 1, wherein the compound of Formula I has the formula:
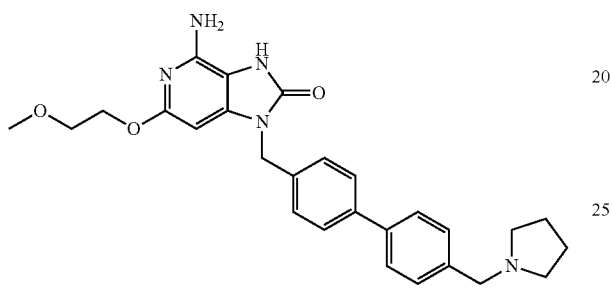
or a pharmaceutically acceptable salt thereof.
* * * * *